(12) United States Patent
Bucala et al.

(10) Patent No.: US 10,842,859 B2
(45) Date of Patent: Nov. 24, 2020

(54) USES OF PARASITE MACROPHAGE MIGRATION INHIBITORY FACTORS

(71) Applicants: Yale University, New Haven, CT (US); GlaxoSmithKline Biologicals SA, Rixensart (BE)

(72) Inventors: Richard Bucala, New Haven, CT (US); Andrew Geall, Cambridge, MA (US)

(73) Assignees: Yale University, New Haven, CT (US); GlaxoSmithKline Biologicals SA, Rixensart (BE)

( * ) Notice: Subject to any disclaimer, the term of this patent is extended or adjusted under 35 U.S.C. 154(b) by 0 days.

(21) Appl. No.: 15/128,851

(22) PCT Filed: Mar. 24, 2015

(86) PCT No.: PCT/EP2015/056310
§ 371 (c)(1),
(2) Date: Sep. 23, 2016

(87) PCT Pub. No.: WO2015/144732
PCT Pub. Date: Oct. 1, 2015

(65) Prior Publication Data
US 2017/0106070 A1  Apr. 20, 2017

(30) Foreign Application Priority Data
Mar. 25, 2014 (EP) .................... 14161614

(51) Int. Cl.
*A61K 39/015* (2006.01)
*C07K 14/44* (2006.01)
(Continued)

(52) U.S. Cl.
CPC ............ *A61K 39/015* (2013.01); *A61K 9/107* (2013.01); *A61K 9/127* (2013.01); *C07K 14/44* (2013.01);
(Continued)

(58) Field of Classification Search
CPC ........ G01N 33/53; A61K 31/00; A61K 31/70; A61K 38/00; A61K 39/002; A61P 33/00;
(Continued)

(56) References Cited

U.S. PATENT DOCUMENTS 4,373,071 A   2/1983  Itakura
4,458,066 A   7/1984  Caruthers et al.
(Continued)

FOREIGN PATENT DOCUMENTS

WO   WO-90/01496 A1   2/1990
WO   WO-97/18229 A1   5/1997
(Continued)

OTHER PUBLICATIONS

Thorat et al., (Infect. And Immun. Dec. 2010. vol. 78. No. 12:5151-5162).*
(Continued)

*Primary Examiner* — Jana A Hines
(74) *Attorney, Agent, or Firm* — Morrison and Foerster LLP

(57) ABSTRACT

This invention relates to compositions (e.g. vaccine compositions) which can be used to provide a subject with protective immunity against a parasite infection. The compositions comprise: (i) an immunologically effective amount of a nucleic acid (e.g. a nucleic acid-based vaccine) comprising a sequence which encodes a parasite macrophage migration inhibitory factor (MIF) antigen; (ii) a parasite MIF antigen; or (iii) an antibody which specifically binds to a parasite MIF antigen. The compositions may be used to treat infections and diseases caused by parasitic protozoans, such as a *Plasmodium* parasite, or parasitic helminths.

8 Claims, 14 Drawing Sheets

Specification includes a Sequence Listing.

(51) Int. Cl.
| | |
|---|---|
| *C07K 16/20* | (2006.01) |
| *C07K 16/24* | (2006.01) |
| *A61K 9/107* | (2006.01) |
| *A61K 9/127* | (2006.01) |
| *C07K 14/445* | (2006.01) |
| *A61K 39/00* | (2006.01) |

(52) U.S. Cl.
CPC .......... *C07K 14/445* (2013.01); *C07K 16/205* (2013.01); *C07K 16/24* (2013.01); *A61K 2039/505* (2013.01); *A61K 2039/53* (2013.01); *A61K 2039/54* (2013.01); *A61K 2039/545* (2013.01); *A61K 2039/55566* (2013.01); *A61K 2039/57* (2013.01); *A61K 2039/70* (2013.01); *Y02A 50/41* (2018.01); *Y02A 50/412* (2018.01)

(58) Field of Classification Search
CPC .......... A61P 33/02; A61P 33/10; C07K 14/44; C07K 14/52; C07K 16/20; C12N 7/00; C12N 15/00; C12N 15/09; C12P 21/02; H01G 9/04; H01G 9/055; C12R 1/10
See application file for complete search history.

(56) References Cited

U.S. PATENT DOCUMENTS

| | | | |
|---|---|---|---|
| 4,500,707 | A | 2/1985 | Caruthers et al. |
| 4,668,777 | A | 5/1987 | Caruthers et al. |
| 4,973,679 | A | 11/1990 | Caruthers et al. |
| 5,047,524 | A | 9/1991 | Andrus et al. |
| 5,132,418 | A | 7/1992 | Caruthers et al. |
| 5,153,319 | A | 10/1992 | Caruthers et al. |
| 5,262,530 | A | 11/1993 | Andrus et al. |
| 5,700,642 | A | 12/1997 | Monforte et al. |
| 5,707,829 | A | 1/1998 | Jacobs et al. |
| 5,928,902 | A | 7/1999 | De Wilde et al. |
| 2001/0021517 | A1 | 9/2001 | Tripp et al. |

FOREIGN PATENT DOCUMENTS

| | | | | |
|---|---|---|---|---|
| WO | WO 20010021517 | * | 9/2001 | ............ G01N 33/53 |
| WO | WO-2001/78770 A1 | | 10/2001 | |
| WO | WO-2002/070002 A2 | | 9/2002 | |
| WO | WO-2005/113782 A1 | | 12/2005 | |
| WO | WO-2011/005799 A2 | | 1/2011 | |
| WO | WO-2011/027222 A2 | | 3/2011 | |
| WO | WO 2012/006376 | * | 1/2012 | ........... A61K 39/155 |
| WO | WO-2012/006376 A2 | | 1/2012 | |
| WO | WO-2012/006380 A2 | | 1/2012 | |
| WO | WO-2012/030901 A1 | | 3/2012 | |
| WO | WO-2012/031043 A1 | | 3/2012 | |
| WO | WO-2012/031046 A2 | | 3/2012 | |
| WO | WO-2013/006825 A1 | | 1/2013 | |
| WO | WO-2013/006834 A1 | | 1/2013 | |
| WO | WO-2013/006837 A1 | | 1/2013 | |
| WO | WO-2013/033563 A1 | | 3/2013 | |

OTHER PUBLICATIONS

Awandare et al., (The American Journal of Tropical Medicine and Hygiene, vol. 76, Issue 6, Jun. 2007, p. 1033-1036) (Year: 2007).*

Bejon et al. (2008). "Efficacy of RTS,S/AS01E Vaccine against Malaria in Children 5 to 17 Months of Age." N Engl J Med, 359(24):2521-32.

Cho et al. (2011). "Drug Repositioning and Pharmacophore Identification in the Discovery of Hookworm MIF Inhibitors." Chemistry and Biology, 18:1089-101.

Dimier-Poisson et al. (2006). "Induction of protective immunity against toxoplasmosis in mice by immunization with Toxoplasma gondii RNA." Vaccine, 24:1705-9.

Dobson et al. (2009). "The crystal structures of macrophage migration inhibitory factor from Plasmodium falciparum and Plasmodium berghei." Protein Science, 18:2578-2591.

Doolan et al (2009). "Acquired Immunity to Malaria," Clinical Microbiology Reviews, 22(1):13-36.

Geall et al. (2012). "Nonviral delivery of self-amplifying RNA vaccines." PNAS, 109(36):14604-9.

Kamir et al. (2008). "A Leishmania Ortholog of Macrophage Migration Inhibitory Factor Modulates Host Macrophage Responses." PNAS, 12:8250-8261.

Kerschbaumer et al. (2012). "Neutralization of Macrophage Migration Inhibitory Factor (MIF) by Fully Human Antibodies Correlates with Their Specificity for the β-Sheet Structure of MIF." The Journal of Biological Chemistry, 287(10):7446-55.

Leng et al. (2003). "MIF Signal Transduction Initiated by Binding to CD74," J Exp Med (197)11:1467-1476.

Miller et al. (2012). "Plasmodium yoelii Macrophage Migration Inhibitory Factor Is Necessary for Efficient Liver-Stage Development." Infection and Immunity, 80:1399-1407.

Petrovsky et al. (2004). "Vaccine adjuvants: Current state and future trends." Immunology and Cell Biology, 82:488-96.

Rosado et al. (2011). "Macrophage migration inhibitory factor (MIF): a key player in protozoan infections." International Journal of Biological Sciences, 7:1239-56.

Seder et al. (2013). "Protection Against Malaria by Intravenous Immunization with a Nonreplicating Sporozoite Vaccine." Science, 341:1359.

Shao et al. (2008). "Detection of Plasmodium falciparum derived macrophage migration inhibitory factor homologue in the sera of malaria patients." Acta Tropica, 106:9-15.

Sun et al. (2012). "A Plasmodium-encoded cytokine suppresses T-cell immunity during malaria." PNAS, 109(31):12280-1, E2117-E2126, S1-5, 17 pages.

Tang et al. (2012). "Evaluation of the immune response induced by DNA vaccines expressing MIF and MCD-1 genes of Trichinella spiralis in BALB/c mice." Journal of Helminthology, 86:430-9.

Tang et al. (2013). "A DNA vaccine co-expressing Trichinella spiralis MIF and MCD-1 with murine ubiquitin induces partial protective immunity in mice." Journal of Helminthology, 87:24-33.

Vermeire et al. (2008). "Orthologs of macrophage migration inhibitory factor from parasitic nematodes." Trends Parasitol, 24:355-63.

Yazdanbakhsh et al. (2010). "Why does immunity to parasites take so long to develop?." Nat Rev Immunol, 10:80-1.

Zhang et al. (2011). "Macrophage migration inhibitory factor homolog from Plasmodium yoelii modulates monocyte recruitment and activation in spleen during infection." Parasitology Research, 110:1755-63.

Bozza et al., (2012). "Macrophage Migration Inhibitory Factor in Protozoan Infections," Journal of Parasitology Research, vol. 2012, Article ID 413052, 12 pages.

* cited by examiner

RNA vaccinations

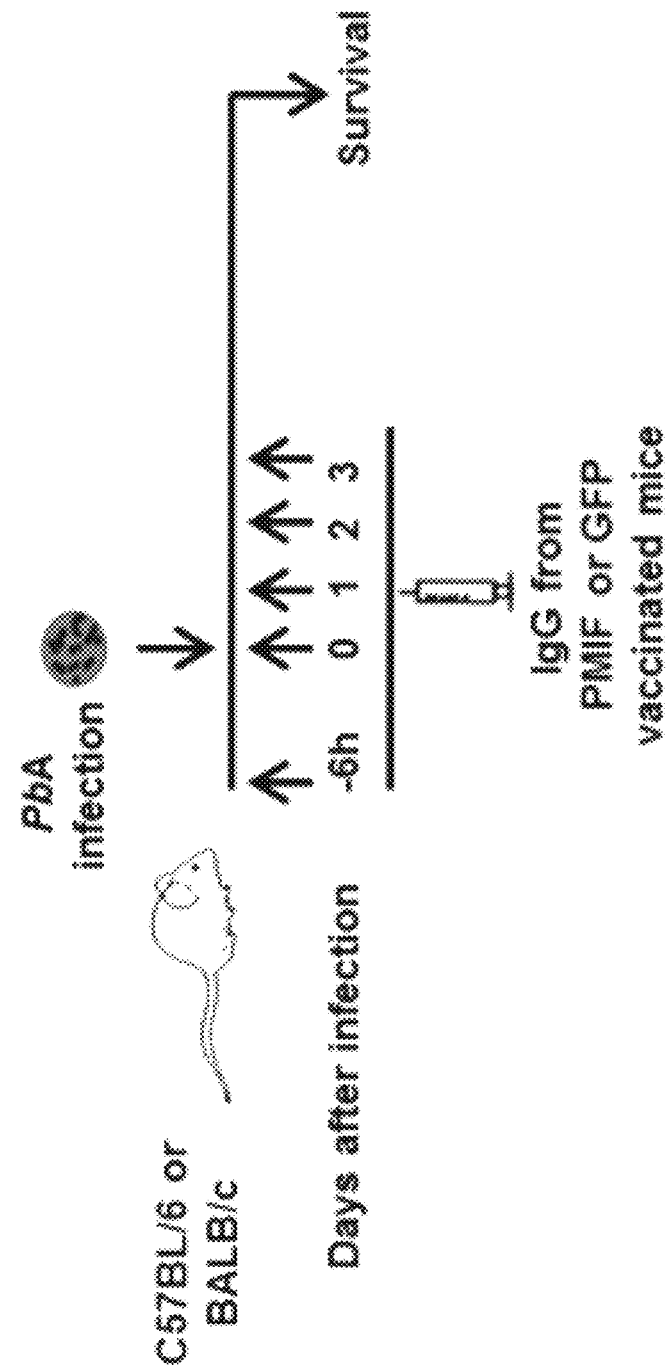

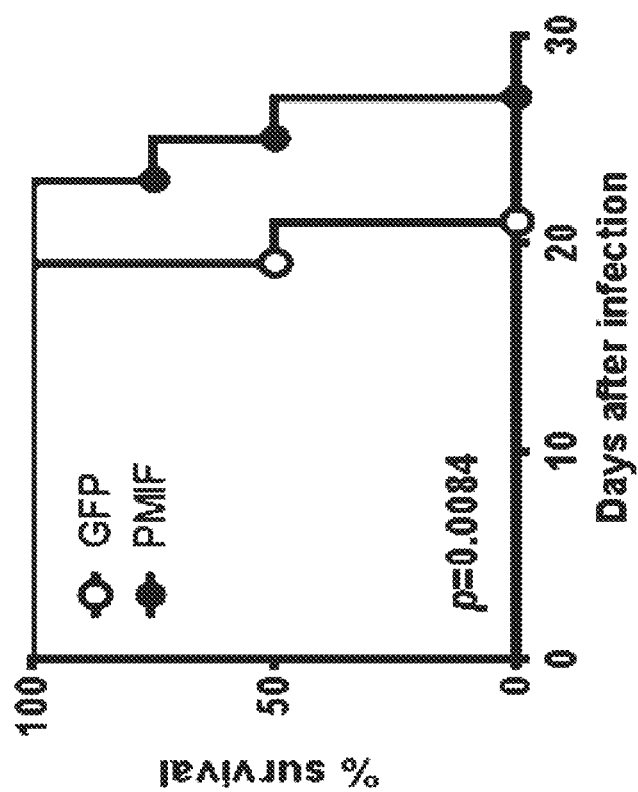
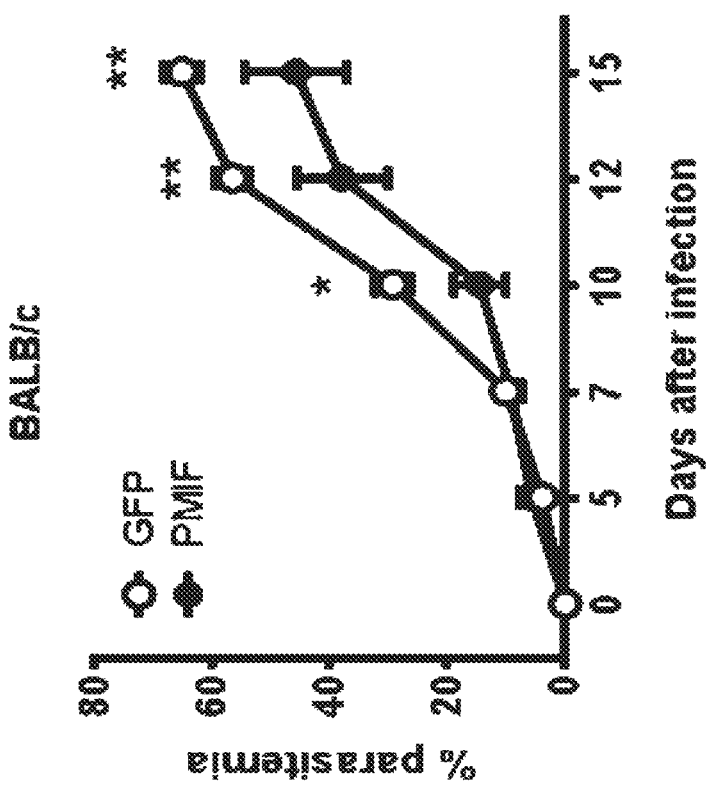
FIG. 10B
FIG. 10C

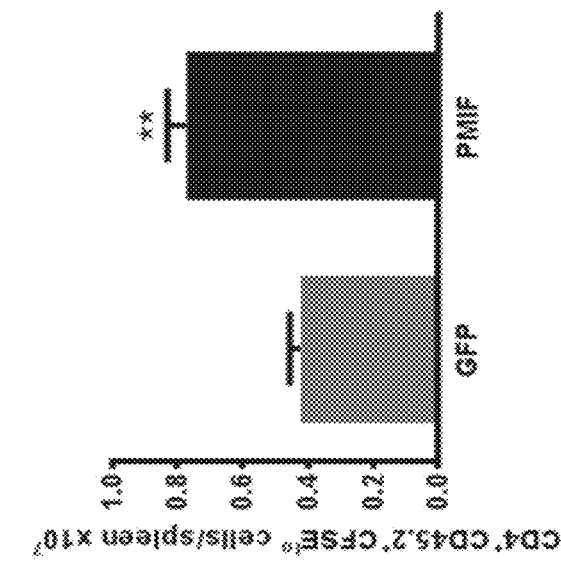
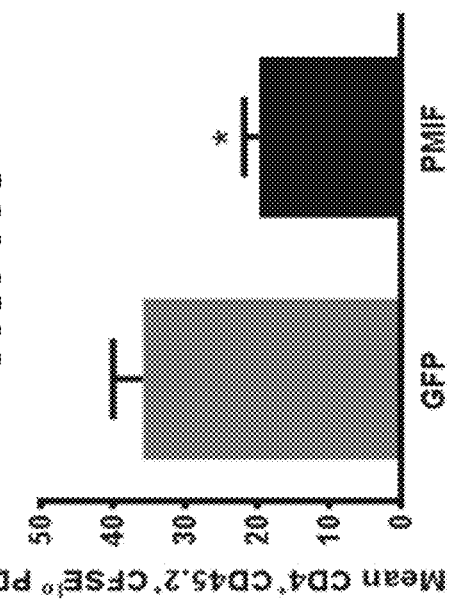
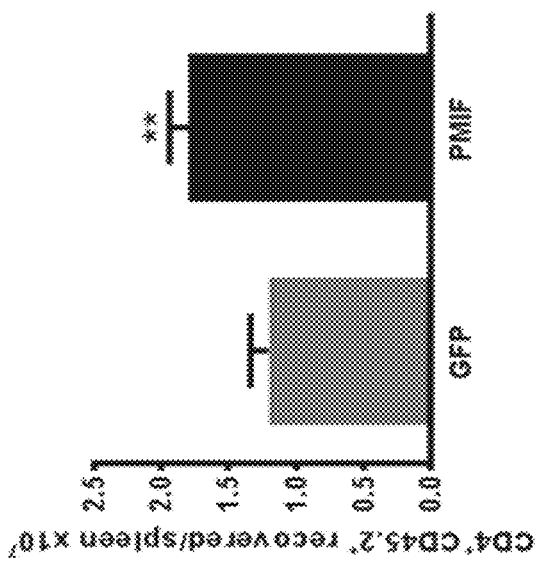
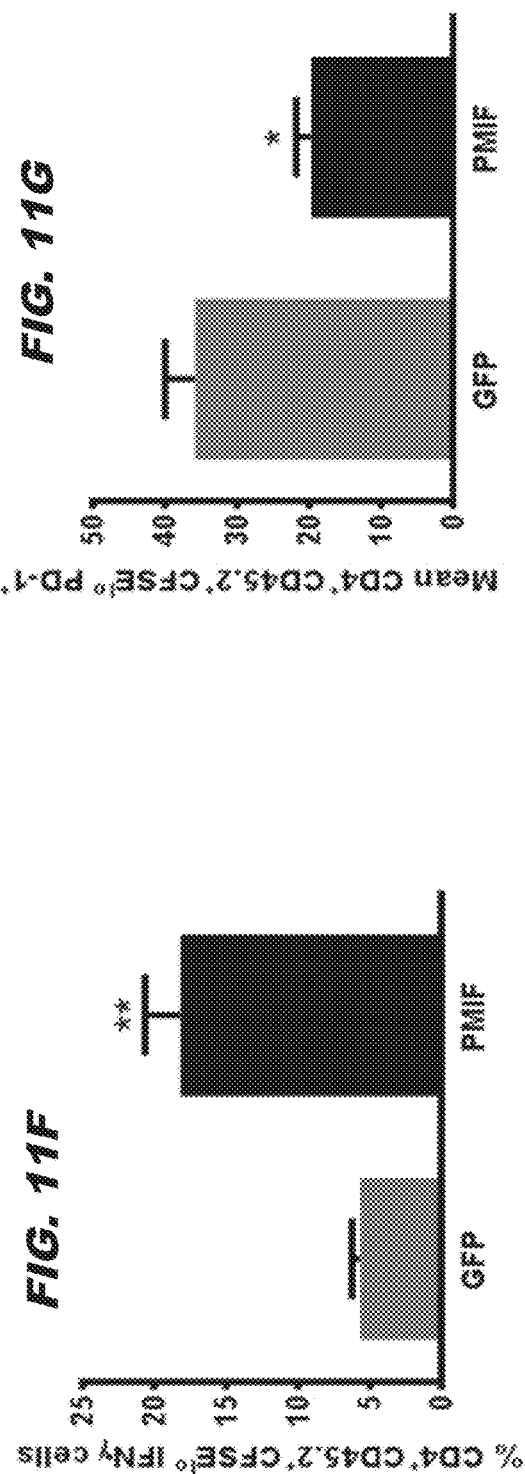
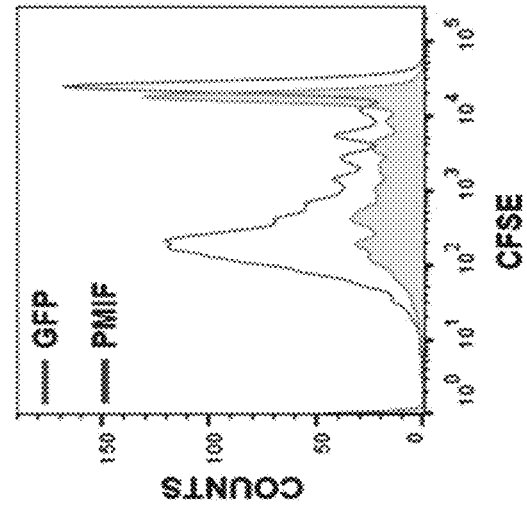

USES OF PARASITE MACROPHAGE MIGRATION INHIBITORY FACTORS

STATEMENT REGARDING FEDERALLY SPONSORED RESEARCH OR DEVELOPMENT

This invention was made with government support under AI110452 awarded by National Institutes of Health. The government has certain rights in the invention.

CROSS REFERENCE TO RELATED APPLICATIONS

This application is a U.S. national phase of PCT/EP2015/056310 (filed Mar. 24, 2015), which claims the benefit of European patent application 14161614.4 (filed Mar. 25, 2014), the disclosures of which are herein incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 303822019000SeqList.txt, date recorded: Sep. 22, 2016, size: 19 KB).

TECHNICAL FIELD

This invention is in the field of treating and preventing parasite infections. In particular, the present invention relates to the use of parasite macrophage migration inhibitory factors (MIFs) for preventing parasite infections such as malaria.

BACKGROUND ART

Parasitic diseases caused by protozoa and helminths affect billions of individuals worldwide and cause millions of human deaths annually, particularly in tropical countries. Malaria, for example, which is caused by *Plasmodium* protozoa, infects 300-500 million individuals annually and leads to more than 1 million deaths. More than a third of the global population is at risk of malaria. Disease mortality is primarily caused by complications due to severe anemia, shock and cerebral malaria, which can be associated with an excessive proinflammatory response. Malaria preferentially kills the immunologically naïve, for example, young children. Recurrent or persistent malaria infection can lead to "tolerance" to severe disease but memory CD4 T cells do not appear to be adequately maintained after malaria infection and fully protective and "sterilizing" immunity never develops [1]. This inability to develop or maintain effective "sterilizing" immunity following infection has been recognised as a characteristic of many other parasite infections in addition to malaria [2]. This makes vaccine development especially difficult.

The *Leishmania* parasite, a flagellated protozoan, is another major cause of parasitic disease. Leishmaniasis affects about 12 million individuals per year and leads to about 60,000 deaths, with about 350 million thought to be at risk. Schistosomiasis is caused by parasitic helminths of the genus *Schistosoma* and is thought to affect 200 million people worldwide and lead to about 20,000 deaths. Hookworm infection by the nematodes *Necator americanus* and *Ancylostoma duodenale* is estimated to affect over 700 million individuals. Other parasitic diseases, such as toxoplasmosis, lymphatic filariasis, onchocerciasis, and Guinea worm disease are thought to affect more than 1 billion people worldwide between them. However, researchers have struggled to develop vaccines against such parasites due to their complex multi-stage life cycles, antigenic variability and immune evasion. Thus, there is still huge demand for effective treatments which protect against parasitic infections, such as malaria.

DISCLOSURE OF THE INVENTION

The present inventors unexpectedly found that macrophage migration inhibitory factor (MIF) from a parasite can be used as an effective vaccine antigen to provide protective immunity against parasite infection.

In particular, the inventors found that immunization of mice with a self-replicating RNA vaccine encoding *Plasmodium berghei* MIF ortholog (PbMIF) led to a measurable and significant decrease in parasitemia following initial *Plasmodium* challenge and a pronounced reduction in parasitemia following cure and re-challenge. The reduced parasitemia was accompanied by an expansion of the *Plasmodium*-responsive memory T cell population in the treated mice. The inventors also showed that immunization with an adjuvanted PbMIF antigen was well tolerated and induced a robust anti-PbMIF immune response. Immunization with PbMIF therefore allows for the increased development of memory T cells and provides significant protection against malaria re-infection. In addition, the inventors showed that passive transfer of an anti-PbMIF antibody significantly reduced parasitemia following *P. berghei* infection.

In mammals, MIF is a ubiquitous and highly conserved proinflammatory cytokine which exhibits tautomerase and oxidoreductase enzymatic activities and is involved in the regulation of a broad spectrum of immune responses. The role of MIF in the mammalian immune system has been widely studied and it has been implicated in the pathogenesis of several diseases such as septic shock, asthma, rheumatoid arthritis and inflammatory bowel disease [3,4]. The precise molecular mechanisms by which MIF functions are not yet well understood, but mammalian MIF has been shown to bind and exert its inflammatory effects via the cell surface receptor CD74 (also known as the MIF receptor, MIF-R)[5,6]. However, the role of MIF was widely thought to be confined to the innate immune system.

MIF orthologs or homologs are found in many parasitic organisms that infect mammals, including unicellular protozoan parasites such as *Plasmodium*, *Leishmania* and *Toxoplasma* and parasitic helminths and nematodes such as *Brugia* and *Ancyclostoma*. Despite often sharing only low levels of sequence identity, these parasite orthologs share close structural and functional similarities with MIFs from their mammalian hosts [3,4,5]. Thus, the present invention is applicable to a wide range of parasites which express a MIF ortholog or homolog. For example, a MIF ortholog produced by *Leishmania major*, has been identified which shares significant structural and functional homology with human MIF, including tautomerase, chemotactic and anti-apoptotic activities and MIF-R binding [7]. MIF proteins produced by *Plasmodium falciparum* and *Plasmodium berghei* have been shown to be similar to one another and to mammalian and other parasite MIFs, to interact with MIF-R and to share similar enzymatic and pro-inflammatory function.

In view of their structural conservation and distribution among evolutionarily distant species, the present inventors hypothesised that parasite MIF orthologs play a role in evasion of the host immune response. Sun et al. [5] recently showed that *Plasmodium* MIF enhanced inflammatory cytokine production and induced activated CD4 T cells to develop into short-lived effector cells rather than memory precursor cells in infected mice, preventing the establishment of immunological memory. Also, CD4 T cells were more susceptible to apoptosis and CD4 T cell recall responses against challenge infections were reduced. Speculative therapeutic applications targeting MIF have been proposed. For example, Dobson et al. [4] suggested that *Plasmodium* MIF could be a potential drug target and that it would be important to selectively target parasite MIF relative to host protein. Vermeire et al. [3] suggested that drugs or vaccines specifically targeting nematode MIF orthologs could have therapeutic value. Cho et al. [8] found that immunization of hamsters with a MIF ortholog from the hookworm *Ancylostoma ceylanicum* alleviated clinical symptoms of hookworm-associated disease (weight loss and anemia) and suggested targeting the hookworm MIF with small molecule inhibitors to treat infection. However, none of these documents elucidated a precise role for MIF orthologs in parasitic infections and, prior to the present invention, no specific therapeutic applications of invertebrate parasite MIF had been provided.

In contrast, the inventors have identified for the first time that an immune response against MIF can be used to provide protective immunity against a parasite infection. In particular, the inventors have shown that parasite MIFs are viable vaccine candidates that may be used either as stand-alone antigens or in combination with other parasite antigens in order to promote long-lasting memory T cell responses and protective immunity against parasite infection. The inventors' findings also establish that an antibody-mediated immune response against parasite MIF can usefully protect a subject against parasite infection. Protective immunity against parasite infection may therefore be established in a subject by eliciting an immune response against parasite MIF and/or blocking parasite MIF function in the subject, thus enabling a subject to develop protective immunological memory against the parasite, particularly when the subject is, or has been exposed to parasite antigens other than MIF as well (e.g. due to infection or exposure to other parasite vaccines).

Accordingly, in one aspect, the invention provides a method for providing protective immunity against a parasite infection in a subject in need thereof, comprising administering an immunologically effective amount of a composition to the subject, wherein the composition comprises: (i) a nucleic acid comprising a sequence which encodes a parasite MIF antigen; (ii) a parasite MIF antigen; or (iii) an antibody which specifically binds to a parasite MIF antigen. In some embodiments, the method may comprise administering a combination of (i), (ii) and/or (iii).

In another aspect, the invention provides a composition for use in a method of providing protective immunity against a parasite infection in a subject in need thereof, which comprises an immunologically effective amount of: (i) a nucleic acid comprising a sequence which encodes a parasite MIF antigen; (ii) a parasite MIF antigen; or (iii) an antibody which specifically binds to a parasite MIF antigen. The composition may be a pharmaceutical composition. Accordingly, the composition may also comprise a pharmaceutically acceptable carrier. In certain embodiments, the composition of (i) or (ii) is a vaccine composition.

The invention also provides a method for providing protective immunity against a parasite infection in a subject in need thereof, comprising administering parasite-responsive CD4 T cells isolated from a compatible host (preferably of the same species as the subject), wherein the host has been immunized with a composition of the invention: i.e. a composition which comprises an immunologically effective amount of (i) a nucleic acid comprising a sequence which encodes a parasite MIF antigen or (ii) a parasite MIF antigen. The compatible host may have been administered a composition of the invention in accordance with a method of providing protective immunity as defined herein. The compatible host may have been administered a composition of the invention as a single dose or in multiple doses (i.e. two or more doses) as described herein. In some embodiments, the compatible host may have been immunized with the composition and subsequently either infected with the parasite (see below) or immunized with another parasite antigen (to produce the parasite-responsive CD4 T cell population). In some embodiments, the compatible host may have been cured of the parasite infection, e.g. by administration of an agent which kills or attenuates the parasite. For example, a *Plasmodium* infection may be cured by administration of an antimalarial. Examples of such agents/antimalarials include chloroquine (CQ), doxycycline, atovaquone (plus proguanil) and mefloquine. In some embodiments, the parasite-responsive CD4 T cells have been isolated from a compatible host who has been: (i) administered a composition of the invention, and (ii) subsequently either infected with the parasite or immunized with another parasite antigen (to produce the parasite-responsive CD4 T cell population). Optionally (e.g. where the host is infected with the parasite), the host may also have been cured of the parasite infection prior to isolation of the parasite-responsive CD4 T cells. The parasite-responsive CD4 T cells isolated from said host may provide the subject with sterilizing immunity (i.e. complete protective immunity), whereby the protected subject can elicit an immune response which completely eliminates the parasite infection.

The parasite may be an invertebrate parasite, for example protozoan or a helminth. In some embodiments, the parasite is a protozoan, for example an apicomplexan parasite such as *Plasmodium*. In some embodiments, the parasitic protozoan belongs to a genus selected from the group consisting of: *Plasmodium, Toxoplasma, Babesia, Eimeria, Theileria, Neospora, Sarcocystis, Leishmania*, and *Trypanosoma*. In some embodiments, the parasite is a helminth, for example a nematode. In some embodiments, the parasitic helminth belongs to a genus selected from the group consisting of: *Ancyclostoma, Necator, Brugia, Wuchereria, Loa, Mansonella, Trichinella, Trichuris, Ascaris, Anisakis, Dracunculus, Strongyloides, Haemonchus, Schistosoma* and *Fasciola*.

In a further aspect, the invention provides a composition comprising an immunologically effective amount of: (i) a nucleic acid comprising a sequence which encodes a parasite MIF antigen; or (ii) a parasite MIF antigen; wherein the MIF antigen is from a parasitic protozoan.

The invention also provides a composition comprising an immunologically effective amount of: (i) a nucleic acid comprising a sequence which encodes a parasite MIF antigen; or (ii) a parasite MIF antigen; wherein the MIF antigen is from a parasitic helminth which belongs to a genus selected from the group consisting of: *Ancyclostoma, Necator, Brugia, Wuchereria, Loa, Mansonella, Trichinella, Trichuris, Ascaris, Anisakis, Dracunculus, Strongyloides, Haemonchus, Schistosoma* and *Fasciola*.

Parasite MIF Antigens

A parasite MIF antigen for use in the present invention generates an immune response in a subject which recognises a naturally occurring parasite MIF polypeptide (e.g. a protective immune response). The parasite MIF antigen may also be referred to as a parasite MIF polypeptide antigen. "Parasite MIF antigen" includes immunogenic fragments of a parasite MIF polypeptide as well as a whole or full-length parasite MIF polypeptide. For example, a parasite MIF antigen may comprise or consist of a full-length parasite MIF polypeptide or an immunogenic fragment of a parasite MIF polypeptide. The parasite MIF polypeptide may be a naturally occurring parasite MIF polypeptide or a variant thereof (i.e. a variant having one or more amino acid substitutions and/or deletions). In certain embodiments, the parasite MIF antigen comprises a contiguous amino acid sequence and/or an epitope which is found in a naturally occurring parasite MIF polypeptide.

"Naturally occurring parasite MIF polypeptide", as used herein, refers to a MIF polypeptide which is expressed in nature by a parasite. Typically, a naturally occurring parasite MIF polypeptide is from about 110 to about 120 amino acids in length. In its mature, processed form it has an N-terminal proline residue (formed after cleavage of methionine during initial protein processing). A naturally occurring parasite MIF polypeptide may have at least one biological activity selected from tautomerase enzymatic activity and MIF-R (e.g. human CD74) binding activity. Naturally occurring MIF polypeptides are members of a unique structural superfamily characterized by forming a trimer of identical subunits. In naturally occurring MIF, each monomer may contain two antiparallel alpha-helices that pack against a four-stranded beta-sheet, with each monomer having two additional beta-strands that interact with the beta-sheets of adjacent subunits to form the interface between monomers. The three beta-sheets may be arranged to form a barrel containing a solvent-accessible channel that runs through the centre of the protein along a molecular three-fold axis.

Examples of naturally occurring MIF polypeptides include:

```
Plasmodium falciparum MIF (UniProt Accession code
Q8I5C5); SEQ ID NO: 1:
PCCEVITNVNLPDDNVQSTLSQIENAISDVMGKPLGYIMSNYDYQKNLRF
GGSNEAYCFVRITSIGGINRSNNSALADQITKLLVSNLNVKSRRIYVEFR
DCSAQNFAFSGSLFG Plasmodium berghei MIF (UniProt Accession code
Q4YQW0); SEQ ID NO: 2:
PCCELITNISIPDDKAQNTLSEIEDAISNILGKPVAYIMSNYDYQKNLRF
SGSNEGYCFVRLTSIGGINRSNNSLLADKITKILSNHLSVKPRRVYIEFR
DCSAQNFAFSGSLFG Plasmodium yoelii MIF (UniProt Accession code
Q1HEA2); SEQ ID NO: 3:
PCCELITNISIPDDKAQNALSEIEDAISNVLGKPVAYIMSNYDYQKNLRF
SGSNEGYCFVRLTSIGGINRSNNSSLADKITKILSNHLGVKPRRVYIEFR
DCSAQNFAFSGSLFG Plasmodium chabaudi MIF (UniProt Accession code
Q4Y5M8); SEQ ID NO: 4:
PCCELITNISIPDDKAQAALSEIEDAISNVLGKPTAYIMSNYDYQKNLRF
AGSNEGYCFVRLTSLGGINRSNNSSLADKITKHLANHLGVKPRRVYIEFR
DCSAQNFAFSGSLFG Plasmodium vivax MIF (UniProt Accession code
A5K0J3); SEQ ID NO: 5:
PCCQVSTNINASDDDAKKALSQIENAISQVLGKPLGYIMSNLDYQKHMRF
GGSHDGFCFVRVTSLGGINKSNNSSLADKITKILASTLNVKSERVFIEFK
DCSAQNFAFNGSLFG Plasmodium knowlesi MIF (UniProt Accession code
B3LCT3); SEQ ID NO: 6:
PCCQVSTNINVSDDDAKKALMQIENAISQVMNKPMGYIMSNLDYQKHMRF
GGSHDGFCFVRVISISGISRSNNTALADKITKILASTIKVKSDRVFIEFK
DCSAQNFAFNGSLFG Toxoplasma gondii MIF (UniProt Accession code
A1XDS9); SEQ ID NO: 7:
PKCMIFCPVAATPAQQDALLKDAEKAVADALGKPLSYVMVGYSQTGQMRF
GGSSDPCAFIRVASIGGITSSTNCKIAAALSAACERHLGVPKNRIYTTFT
NKSPSEWAMGDRTFG Leishmania major MIFi (UniProt Accession code
Q4Q413); SEQ ID NO: 8:
PVIQTFVSTPLDHHKRENLAQVYRAVTRDVLGKPEDLVMMTFHDSTPMHF
FGSTDPVACVRVEALGGYGPSEPEKVTSIVTAAITKECGIVADRIFVLYF
SPLHCGWNGTNF Leishmania major MIF2 (UniProt Accession code
Q4Q412); SEQ ID NO: 9:
PFLQTIVSVSLDDQKRANLSAAYGMICREELGKPEDFVMTAFSDKTPISF
QGSTAPAAYVRVESWGEYAPSKPKMMTPRIAAAITKECGIPAERIYVFYY
STKHCGWNGTNF Giardia intestinalis MIF (UniProt Accession code
A8BFP4); SEQ ID NO: 10:
PCAIVTTNADFTKDQADAFCLDMGQVLAKETGKPVSYCMAGVRKADMSFG
TSTDLCCFVDFYCIGVISQAKNPSISAAITGCLTQHFKVKPERVYISFNE
AKGHNWGFNGSTF Brugia malayi MIF (UniProt Accession code A8PJU3);
SEQ ID NO: 11:
PYFTIDTNIPQNSISSAFLKKASNVVAKALGKPESYVSIHVNGGQAMVFG
GSEDPCAVCVLKSIGCVGPKVNNSHAEKLYKLLADELKIPKNRCYIEFVD
IEASSMAFNGSTFG Wuchereria bancrofti MIF (UniProt Accession code
O44786); SEQ ID NO: 12:
PYFTIDTNKPQDSISSAFLKKAPNVVPKALGKPESYVSIHVNGGQPMVFG
GSEDPCPVCVLKSIGCVGPKVNNSHAEKLYKLLADELKIPKNRCYIESVD
IEASSMAFNGSTFG Ancylostoma duodenale MIF (UniProt Accession code
I3RWR9); SEQ ID NO: 13:
PMVRVATNLPDKDVPANFEERLTDILAESMNKPRNRIAIEVMAGQRITHG
ASRNPVAVIKVESIGALSADDNIRHTQKITQFCQDTLKLPKDKVIITYFD
LQPIHVGFNGTTVAAATM Ancylostoma ceylanicum MIF1 (UniProt Accession
code A4GRE3); SEQ ID NO: 14:
PMVRVATNLPDKDVPANFEERLTDLLAESMNKPRNRIAIEVLAGQRITHG
ASRNPVAVIKVESIGALSADDNIRHTQKITQFCQDTLKLPKDKVIITYFD
LQPIHVGFNGTTVAAATM Ancylostoma ceylanicum MIF2 (UniProt Accession
code B6RTC1); SEQ ID NO: 15:
PVFQLHTNVSQDKVTPDLLKQISALVARILHKPESYVAVHVVPDQKMTFA
GTDGPCGIGILKSIGGVGGSQNNSHAKALFALIKDHLGIEGSRMYIEFVD
IGASDIAHNGRTFA Trichinella spiralis MIF (UniProt Accession code
E5SFT7); SEQ ID NO: 16:
PIFTLNTNIKATDVPSDFLSSTSALVGNILSKPGSYVAVHINTDQQLSFG
GSTNPAAFGTLMSIGGIEPSRNRDHSAKLFDHLNKKLGIPKNRMYIHFVN
LNGDDVGWNGTTF Trichuris trichiura MIF (UniProt Accession code
P81748); SEQ ID NO: 17:
PIFTFSTNVPSENISVDFLKSTSKLIAGMLGKPESYVAVHINGGQKITFG
GTDAPAGFGQLLSLGGVGGEKNRSHSAKLFKHLTDGLGIPGNRMYINFVD
MRGSDVGYNGSTF Onchocerca volvulus MIF (UniProt Accession code
Q963F7); SEQ ID NO: 18:
PAFTINTNIPQSNVSDAFLKKASSTVAKALGKPESYVAIHVNGGQAMVFG
GSTDPCAVCVLKSIGCVGPNVNNSHSEKLFKLLADELKIPKNRCYIEFVN
IDASTMAFNGSTFG
```

The UniProt Accession codes referred to above refer to MIF polypeptide sequences which include an N-terminal methionine that is not present in the mature MIF polypeptide. SEQ ID NOs: 1-18 show the mature MIF polypeptide sequence, beginning with an N-terminal proline.

A parasite MIF antigen may comprise a parasite MIF polypeptide which is a variant of a naturally occurring parasite MIF polypeptide. The variant may comprise an amino acid sequence which is at least 70%, at least 75%, at least 80%, at least 85%, at least 90%, at least 95%, at least 98% or at least 99% identical to a full-length naturally occurring parasite MIF polypeptide, for example, to a polypeptide according to SEQ ID NO: 1, 2, 3, 4, 5, 6, 7, 8, 9, 10, 11, 12, 13, 14, 15, 16, 17 or 18. Alternatively, or in addition, the parasite MIF antigen may comprise an immunogenic fragment (i.e. an epitope-containing fragment) of a parasite MIF polypeptide which may comprise a contiguous amino acid sequence of at least 8, at least 9, at least 10, at least 11, at least 12, at least 13, at least 14, at least 15, at least 16, at least 17, at least 18, at least 19 amino acids which is identical to a contiguous amino acid sequence of a naturally occurring parasite MIF polypeptide, for example, a polypeptide according to SEQ ID NO: 1, 2, 3, 4, 5, 6, 7, 8, 9, 10, 11, 12, 13, 14, 15, 16, 17 or 18.

In some embodiments, the parasite MIF antigen comprises an amino acid sequence which is at least 70% identical (e.g. at least 75%, at least 80%, at least 85%, at least 90%, at least 95%, at least 98% or at least 99% identical) to SEQ ID NO:1 and/or comprises a contiguous amino acid sequence of at least 8 amino acids (e.g. at least 9, at least 10, at least 11, at least 12, at least 13, at least 14, at least 15, at least 16, at least 17, at least 18, at least 19 amino acids) which is identical to a contiguous amino acid sequence of SEQ ID NO:1. In some embodiments, the parasite MIF antigen comprises an amino acid sequence which is at least 70% identical (e.g. at least 75%, at least 80%, at least 85%, at least 90%, at least 95%, at least 98% or at least 99% identical) to SEQ ID NO:2 and/or comprises a contiguous amino acid sequence of at least 8 amino acids (e.g. at least 9, at least 10, at least 11, at least 12, at least 13, at least 14, at least 15, at least 16, at least 17, at least 18, at least 19 amino acids) which is identical to a contiguous amino acid sequence of SEQ ID NO:2.

Where the parasite MIF antigen is a variant of a naturally occurring parasite MIF polypeptide, the parasite MIF antigen may have one or more amino acid (e.g. 1, 2, 3, 4, 5, 6, 7, 8, 9, 10, 11, 12, 13, 14, 15, 16, 17, 18, 19, 20 etc.) substitutions and/or deletions relative to the naturally occurring parasite MIF polypeptide. The variant may have a maximum of 5, 10, 15 or 20 substitutions and/or deletions relative to the naturally occurring parasite MIF polypeptide. The one or more substitutions may be conservative amino acid replacements i.e. replacements of one amino acid with another which has a related side chain. Genetically-encoded amino acids are generally divided into four families: (1) acidic i.e. aspartate, glutamate; (2) basic i.e. lysine, arginine, histidine; (3) non-polar i.e. alanine, valine, leucine, isoleucine, proline, phenylalanine, methionine, tryptophan; and (4) uncharged polar i.e. glycine, asparagine, glutamine, cystine, serine, threonine, tyrosine. Phenylalanine, tryptophan, and tyrosine are sometimes classified jointly as aromatic amino acids. In general, substitution of single amino acids within these families does not have a major effect on the biological activity. The variant may also include one or more (e.g. 1, 2, 3, 4, 5, 6, 7, 8, 9, 10, 11, 12, 13, 14, 15, 16, 17, 18, 19, 20 etc.) amino acid insertions (e.g. each of 1, 2, 3, 4 or 5 amino acids) relative to the naturally occurring parasite MIF polypeptide. The variant may have a maximum of 5, 10, 15 or 20 insertions relative to the naturally occurring parasite MIF polypeptide.

The variant may be encoded by a nucleic acid sequence which can hybridize under stringent conditions to a nucleic acid sequence that encodes a naturally occurring parasite MIF polypeptide. Hybridization reactions can be performed under conditions of different "stringency". Conditions that increase stringency of a hybridization reaction are widely known and published in the art (e.g. page 7.52 of reference 9). Examples of relevant conditions include (in order of increasing stringency): incubation temperatures of 25° C., 37° C., 50° C., 55° C. and 68° C.; buffer concentrations of 10×SSC, 6×SSC, 1×SSC, 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or de-ionized water. Hybridization techniques and their optimization are well known in the art [e.g. see references 9-12, etc.]. Preferably, a nucleic acid sequence encoding a variant hybridizes under high stringency conditions (e.g. 68° C. and 0.1×SSC) to a nucleic acid sequence that encodes a naturally occurring parasite MIF polypeptide.

In certain embodiments, the parasite MIF antigen is at least 20, at least 30, at least 40, at least 50, at least 60, at least 70, at least 80, at least 90 or at least 100 amino acids in length.

As used herein, the term "antigen" refers to a molecule containing one or more epitopes (e.g., linear, conformational or both) that will stimulate a host's immune system to make a humoral and/or cellular antigen-specific immunological response (i.e. an immune response which specifically recognises a naturally occurring parasite MIF polypeptide). An "epitope" is that portion of an antigen that determines its immunological specificity.

The antigen, or a nucleic acid encoding the antigen, may be isolated or purified from a natural source (i.e. a parasite of interest), but will usually be produced by recombinant or synthetic techniques, all of which will be familiar to those skilled in the art.

A parasite MIF antigen may comprise at least one T-cell or B-cell epitope of the naturally occurring parasite MIF polypeptide. T- and B-cell epitopes can be identified empirically (e.g. using PEPSCAN [13,14] or similar methods), or they can be predicted (e.g. using the Jameson-Wolf antigenic index [15], matrix-based approaches [16], TEPITOPE [17], neural networks [18], OptiMer & EpiMer [19, 20], ADEPT [21], Tsites [22], hydrophilicity [23], antigenic index [24] or the methods disclosed in reference 25 etc.).

In certain embodiments, the parasite MIF antigen is capable of eliciting a T cell response in the subject, for example a helper (CD4) T cell response.

Multiple Parasite MIF Antigens

A composition of the invention may use, or may target, a single parasite MIF antigen, or may use or target two or more different parasite MIF antigens. Thus, in some embodiments, a composition as defined herein may comprise or encode a single parasite MIF antigen or two or more different parasite MIF antigens, and/or may comprise antibodies which specifically bind to a single parasite MIF antigen or to two or more different parasite MIF antigens.

In some embodiments, the composition may comprise a nucleic acid which encodes two or more parasite MIF antigens. In some embodiments, the composition may comprise two or more nucleic acids which each encode a parasite MIF antigen. In some embodiments, the composition may comprise two or more parasite MIF antigens. In some embodiments, the composition may comprise two or more antibodies which each respectively bind to two or more parasite MIF antigens.

In some embodiments, a composition of the invention may comprise a combination of: (i) a nucleic acid comprising a sequence which encodes a parasite MIF antigen; (ii) a parasite MIF antigen; (iii) an antibody which specifically binds to a parasite MIF antigen. For example, the composition may comprise a combination of (i) and (ii), (i) and (iii), (ii) and (iii), or (i), (ii) and (iii). In each of (i), (ii) and (iii), the parasite MIF antigen may be a different parasite MIF antigen.

The different parasite MIF antigens may be derived from different parasite species, may be different variants of a parasite MIF antigen, and/or may comprise different parasite MIF epitopes. In some embodiments, a composition may comprise or encode two, three, four, or more, parasite MIF antigens that may contain a range of epitopes. In some embodiments, a composition may comprise two, three, four, or more antibodies which each specifically bind to a different parasite MIF antigen epitope.

Additional Parasite Antigens

As discussed above, the immune response to the parasite MIF antigen may enhance the development of a protective immune response (e.g. a CD4 memory T cell response) to one or more additional parasite antigens. Thus, parasite MIFs may be used either as stand-alone antigens or in combination with additional parasite antigens in order to promote long-lasting memory T cell responses and protective immunity against parasite infection.

Thus, a composition as defined herein (i.e. a composition comprising (i) a nucleic acid comprising a sequence which encodes a parasite MIF antigen, (ii) a parasite MIF antigen, or (iii) an antibody which specifically binds to a parasite MIF antigen) may further comprise or encode one or more additional parasite antigens (i.e. parasite antigens which are not parasite MIF antigens, or "non-MIF parasite antigens"). In some embodiments, the composition may comprise a nucleic acid sequence which encodes an additional parasite antigen. For example, the composition may comprise a nucleic acid comprising both a sequence which encodes a parasite MIF antigen and a sequence which encodes an additional parasite antigen (i.e. the parasite MIF antigen and the additional parasite antigen may be encoded by the same nucleic acid molecule). Alternatively, or in addition, the composition may comprise a further nucleic acid comprising a sequence which encodes an additional parasite antigen (i.e. the parasite MIF antigen and the additional parasite antigen may be encoded by separate nucleic acid molecules).

In some embodiments, the composition may comprise both a parasite MIF antigen and an additional parasite antigen.

Alternatively, or in addition, a composition as defined herein (i.e. a composition comprising (i) a nucleic acid comprising a sequence which encodes a parasite MIF antigen, (ii) a parasite MIF antigen, or (iii) an antibody which specifically binds to a parasite MIF antigen) may be administered to a subject in combination with a further composition which comprises or encodes one or more additional parasite antigens. The further composition may be a parasite vaccine composition. For example, the one or more additional parasite antigens may be formulated as a parasite vaccine composition. In some embodiments, a composition as defined herein may be administered to a subject in combination with a further composition which comprises a nucleic acid comprising a sequence which encodes an additional parasite antigen. In some embodiments, a composition as defined herein may be administered to a subject in combination with a further composition which comprises an additional parasite antigen.

Accordingly, in some embodiments, a method for providing protective immunity against a parasite infection in a subject in need thereof according to the present invention may further comprise administering to the subject a further composition which comprises a nucleic acid comprising a sequence which encodes an additional parasite antigen. In some embodiments, a method for providing protective immunity against a parasite infection in a subject in need thereof according to the present invention may further comprise administering to the subject a further composition which comprises an additional parasite antigen.

Thus, in a method for providing protective immunity against a parasite infection in a subject in need thereof according to the present invention, the subject may be administered: (1) a composition as defined herein which comprises a nucleic acid comprising a sequence which encodes a parasite MIF antigen and a further composition which comprises a nucleic acid comprising a sequence which encodes an additional parasite antigen; (2) a composition as defined herein which comprises a nucleic acid comprising a sequence which encodes a parasite MIF antigen and a further composition which comprises an additional parasite antigen; (3) a composition as defined herein which comprises a parasite MIF antigen and a further composition which comprises a nucleic acid comprising a sequence which encodes an additional parasite antigen; (4) a composition as defined herein which comprises a parasite MIF antigen and a further composition which comprises an additional parasite antigen; (5) a composition as defined herein which comprises an antibody which specifically binds to a parasite MIF antigen and a further composition which comprises a nucleic acid comprising a sequence which encodes an additional parasite antigen; or (6) a composition as defined herein which comprises an antibody which specifically binds to a parasite MIF antigen and a further composition which comprises an additional parasite antigen.

The composition as defined herein (i.e. a composition comprising (i) a nucleic acid comprising a sequence which encodes a parasite MIF antigen, (ii) a parasite MIF antigen, or (iii) an antibody which specifically binds to a parasite MIF antigen) and the composition comprising or encoding the additional parasite antigen may be provided as separate components and/or administered separately. Alternatively, the composition as defined herein (i.e. a composition comprising (i) a nucleic acid comprising a sequence which encodes a parasite MIF antigen, (ii) a parasite MIF antigen, or (iii) an antibody which specifically binds to a parasite MIF antigen) and the composition comprising or encoding the additional parasite antigen may be mixed prior to administration.

Administration of (A) the composition as defined herein (i.e. a composition comprising (i) a nucleic acid comprising a sequence which encodes a parasite MIF antigen, (ii) a parasite MIF antigen, or (iii) an antibody which specifically binds to a parasite MIF antigen) and (B) the composition comprising or encoding the additional parasite antigen, in any combination as described herein, may be contemporaneous. For example, compositions (A) and (B) may be administered simultaneously, separately or sequentially. Compositions (A) and (B) may be administered within 12 months of each other, within six months of each other, or within one month or less of each other (e.g. within 10 days). Compositions (A) and (B) may be administered within 7 days, within 3 days, within 2 days, or within 24 hours of each other. Simultaneous administration may involve administering compositions (A) and (B) at the same time. Simultaneous administration may include administration of (A) and (B) to a patient within 12 hours of each other, within 6 hours, within 3 hours, within 2 hours or within 1 hour of each other, typically within the same visit to a clinical centre. Composition (A) may be administered before (B).

In certain embodiments, the additional parasite antigen may be derived from the same parasite species as the parasite MIF antigen. In other embodiments, the additional parasite antigen may be from a different species compared to the parasite MIF antigen.

The one or more additional parasite antigens may, for example, be *Plasmodium* antigens, or derived from *Plasmodium* antigens, such as circumsporozoite (CS) protein (optionally fused to a hepatitis B surface antigen (HBsAg)); merozoite surface protein (MSP), for example MSP-1; reticulocyte-binding protein homologue 5 (RH5), for example, PfRH5; apical membrane antigen 1 (AMA1); thrombospondin-related adhesion protein (TRAP); ME-TRAP (multiple epitope string with thrombospondin-related adhesion protein: a pre-erythrocytic fusion antigen consisting of 17 B cell, CD4+ and CD8+ T cell epitopes from six *P. falciparum* antigens fused to the T9/96 allele of TRAP); liver-stage antigen 1 (LSA-1); liver stage antigen-3 (LSA-3); exported protein 1 (Exp-1); antigen encoded by polyepitope DNA EP1300 with linker sequences from four pre-erythrocytic antigens, CS, TRAP, LSA-1 and Exp-1; polyprotein comprising LSA-3, sporozoite threonine and asparagine rich protein (STARP), Exp1, Pfs16, TRAP, and LSA-1; a *falciparum* merozoite protein (FMP) such as FMP010 or FMP001; merozoite surface protein-3 (MSP-3); erythrocyte binding antigen-175 (EBA175); EBA175 RII; serine repeat antigen (SERA5); SE36, a recombinant protein corresponding to a fragment of the SERA5 antigen; glutamate-rich protein (GLURP); ring-infected erythrocyte surface antigen (RESA); antigenic fragments of any one of the foregoing; or a combination thereof. In some embodiments, the one or more additional antigens may be in the form of non-replicating sporozoites, such as PfSPZ (which is composed of attenuated, aseptic, purified, cryopreserved *Plasmodium falciparum* sporozoites) (e.g. Seder et al. Science 341, 1359 (2013)).

In some embodiments, an additional parasite antigen for use with the invention is a CS protein, which includes *P. falciparum* antigens based on the circumsporozoite (CS) protein. This can take the form of a recombinant protein that fuses a part of the CS protein with HBsAg, known as "RTS', or TRAP. Suitable *P. falciparum* antigens for making HBsAg hybrids may be based on a subunit of the circumsporozoite surface antigen ("CSP") e.g. they may include between 3 and 20 repeats of its NANP (SEQ ID NO: 19) motif, and/or they may include the C-terminal region of CSP (but typically not including the final 12 amino acids from the C-terminus). RTS is a hybrid protein comprising substantially all the C-terminal portion of CS from the NF54 or 7G8 isolate of *P. falciparum* (amino acids 210 to 398, which includes 19 NANP (SEQ ID NO: 19) repeats and the T cell epitope region at amino acids 367 to 390), fused to the N-terminus of HBsAg by four amino acids of the preS2 portion of HBsAg [26]. The sequence of RTS can thus contain: (i) a N-terminus methionine residue; (ii) Met-Ala-Pro; (iii) 189 amino acids corresponding either to amino acids 210-398 of CS protein from *P. falciparum* 7G8 or to amino acids 207-395 of CS protein from *P. falciparum* NF54; (iv) Arg or Gly; (v) Pro-Val-Thr-Asn from hepatitis B Pre-S2 protein; and (vi) HBsAg. When expressed in yeast (particularly in *S. cerevisiae*) RTS is produced as a lipoprotein particle (including in particular phospholipids), and when it is co-expressed with the S antigen from HBV it produces a mixed particle known as RTS,S. A RTS:S ratio of about 1:4 is useful. TRAP antigens are described in reference 27. In some embodiments, an additional parasite antigen may take the form of RTS,S.

The one or more additional parasite antigens may be derived from any species of *Plasmodium*, including any of the *Plasmodium* species listed below. In some embodiments, the additional parasite antigen is a *Plasmodium falciparum* or *Plasmodium vivax* antigen. In some embodiments, the additional parasite antigen is CS protein (optionally fused to HBsAg); MSP-1; PfRH5; AMA1; and antigenic fragments thereof. For example, the parasite MIF antigen may be a *Plasmodium falciparum* MIF antigen and the additional parasite antigen may be a *Plasmodium falciparum* circumsporozoite (CS) protein fused to a hepatitis B surface antigen (HBsAg).

In further embodiments, the one or more additional parasite antigens may be *Leishmania* antigens, or derived from *Leishmania* antigens, such as thiol-specific antioxidant (TSA); stress-inducible protein 1 (LmSTI1); *Leishmania* elongation initiation factor (LeIF); recombinant surface antigen gp63; lipophosphoglycan; a 46 kD promastigote antigen derived from *L. amazonensis*; *Leishmania*-activated C kinase (LACK); parasite surface antigen (PSA); and parasite surface antigen-2 (PSA-2); *Schistosoma* antigens such as 63 kD parasite myosin; 97 kD paramyosin; 28 kD triose phosphate isomerase (TPI); 23 kD integral membrane protein (Sm23); 26 and 28 kD GST; 28 kD *S. haematobium* GST (Sh28GST); Tetraspanin-2 (SmTSP-2) and fatty acid binding protein (FABP); may be *Ancyclostoma* antigens, or derived from *Ancylostoma* antigens, such as *Ancylostoma*-secreted protein (ASP); may be *Necator* antigens, or derived from *Necator* antigens, such as Na-ASP-2, a 21 kDa protein from *Necator americanus*; antigenic fragments of any one of the foregoing, or a combination thereof.

A composition of the invention may also be used in a method of enhancing an immune response to another (i.e. non-MIF) parasite antigen (e.g. another *Plasmodium* antigen, as described herein). Thus, provided herein is a method of enhancing an immune response to a parasite antigen comprising administering a composition of the invention (i.e. a composition comprising (i) a nucleic acid comprising a sequence which encodes a parasite MIF antigen, (ii) a parasite MIF antigen, and/or (iii) an antibody which specifically binds to a parasite MIF antigen) to a subject. The parasite antigen against which the immune response is enhanced may include one or more additional parasite antigens, as defined herein. The method may further comprise administering the non-MIF parasite antigen to the subject. The MIF and non-MIF antigens can be administered simultaneously, separately, or sequentially.

The immune response may be enhanced relative to the immune response in a subject treated with only the non-MIF parasite antigen. The enhanced immune response may comprise an enhanced protective immune response against the parasite infection. Protective immune responses are defined herein. For example, the protective immune response may be characterized by protective immunological memory (e.g. a protective memory T cell response) against the parasite. Protective immunity may be sterilizing immunity.

Polypeptides

In some embodiments, a polypeptide according to the present invention is in a non-naturally occurring form (e.g. a recombinant or modified form).

For example, polypeptides (e.g. antigens) disclosed herein can be prepared by chemical synthesis (in whole or in part), by digesting longer polypeptides using proteases, by translation from RNA, by purification from cell culture (e.g. from recombinant expression), from the organism itself, etc. An exemplary method for production of peptides<40 amino acids long involves in vitro chemical synthesis [28,29]. Solid-phase peptide synthesis techniques, such as methods based on tBoc or Fmoc [30] chemistry, are known in the art. Enzymatic synthesis [31] may also be used in part or in full. As an alternative to chemical synthesis, biological synthesis may be used e.g. the polypeptides may be produced by translation. This may be carried out in vitro or in vivo. Biological methods are in general restricted to the production of polypeptides based on L-amino acids, but manipulation of translation machinery (e.g. of aminoacyl tRNA molecules) can be used to allow the introduction of D-amino acids (or of other non-natural amino acids, such as iodotyrosine or methylphenylalanine, azidohomoalanine, etc.) [32]. Where D-amino acids are included, however, it is preferred to use chemical synthesis. Polypeptides of the disclosure may have covalent modifications at the C-terminus and/or N-terminus. They can also take various forms (e.g. native, fusions, glycosylated, non-glycosylated, lipidated, non-lipidated, phosphorylated, non-phosphorylated, myristoylated, non-myristoylated, monomeric, multimeric, particulate, denatured, etc.). The polypeptides can be naturally or non-naturally glycosylated (i.e. the polypeptide may have a glycosylation pattern that differs from the glycosylation pattern found in the corresponding naturally occurring polypeptide).

Non-naturally occurring forms of polypeptides according to the invention may comprise one or more heterologous amino acid sequences (e.g. another antigen sequence or a detectable tag) in addition to a parasite MIF antigen sequence. For example, a polypeptide of the invention may be a fusion protein. Alternatively, or in addition, the amino acid sequence or chemical structure of the polypeptide may be modified (e.g. with one or more non-natural amino acids, by covalent modification, and/or or by having a different glycosylation pattern, for example, by the removal or addition of one or more glycosyl groups) compared to a naturally-occurring polypeptide sequence.

Polypeptides (e.g. antigens) disclosed herein are preferably provided in purified or substantially purified form i.e. substantially free from other polypeptides (e.g. free from naturally-occurring polypeptides), particularly from other parasite or host cell polypeptides; for example, at least about 50% pure (by weight), at least about 60% pure (by weight), at least about 70% pure (by weight), at least about 80% pure (by weight), or at least about 90% pure, etc. Alternatively, less than about 50%, less than about 40%, less than about 30%, less than about 20%, less than about 10%, or less than about 5% of a composition is made up of other expressed polypeptides.

Nucleic Acids

The invention also relates to nucleic acid comprising a sequence which encodes a parasite MIF antigen, as disclosed herein. Nucleic acid according to the invention can take various forms (e.g. single-stranded, double-stranded, vectors etc.). Nucleic acids of the invention may be circular or branched, but will generally be linear.

The nucleic acids used in the invention are preferably provided in purified or substantially purified form i.e. substantially free from other nucleic acids (e.g. free from naturally-occurring nucleic acids), particularly from other parasite or host cell nucleic acids, generally being at least about 50% pure (by weight), and usually at least about 90% pure.

Nucleic acids may be prepared in many ways e.g. by chemical synthesis (e.g. phosphoramidite synthesis of DNA) in whole or in part, by digesting longer nucleic acids using nucleases (e.g. restriction enzymes), by joining shorter nucleic acids or nucleotides (e.g. using ligases or polymerases), from genomic or cDNA libraries, etc.

The term "nucleic acid" in general means a polymeric form of nucleotides of any length, which contain deoxyribonucleotides, ribonucleotides, and/or their analogs. It includes DNA, RNA, DNA/RNA hybrids. It also includes DNA or RNA analogs, such as those containing modified backbones (e.g. peptide nucleic acids (PNAs) or phosphorothioates) or modified bases. Thus the nucleic acid of the disclosure includes mRNA, DNA, cDNA, recombinant nucleic acids, branched nucleic acids, plasmids, vectors, etc. Where the nucleic acid takes the form of RNA, it may or may not have a 5' cap.

The nucleic acids of the invention comprise a sequence which encodes at least one parasite MIF antigen. Typically, the nucleic acids of the invention will be in recombinant form, i.e. a form which does not occur in nature. For example, the nucleic acid may comprise one or more heterologous nucleic acid sequences (e.g. a sequence encoding another antigen and/or a control sequence such as a promoter or an internal ribosome entry site) in addition to the sequence encoding at least one parasite MIF antigen. The nucleic acid may be part of a vector i.e. part of a nucleic acid construct designed for transduction/transfection of one or more cell types. Vectors may be, for example, "expression vectors" which are designed for expression of a nucleotide sequence in a host cell, or "viral vectors" which are designed to result in the production of a recombinant virus or virus-like particle.

Alternatively, or in addition, the sequence or chemical structure of the nucleic acid may be modified compared to a naturally-occurring sequence which encodes a parasite MIF antigen. The sequence of the nucleic acid molecule may be modified, e.g. to increase the efficacy of expression or replication of the nucleic acid, or to provide additional stability or resistance to degradation. For example, the sequence of the nucleic acid molecule may be codon optimized for expression in a desired host, such as a mammalian (e.g. human) cell. Such modification with respect to codon usage may increase translation efficacy and half-life of the nucleic acid. A poly A tail (e.g., of about 30 adenosine residues or more) may be attached to the 3' end of the RNA to increase its half-life. The 5' end of the RNA may be capped with a modified ribonucleotide with the structure m7G (5') ppp (5') N (cap 0 structure) or a derivative thereof, which can be incorporated during RNA synthesis or can be enzymatically engineered after RNA transcription (e.g., by using Vaccinia Virus Capping Enzyme (VCE) consisting of mRNA triphosphatase, guanylyl-transferase and guanine-7-methyltransferase, which catalyzes the construction of N7-monomethylated cap 0 structures). Cap 0 structure plays an important role in maintaining the stability and translational efficacy of the RNA molecule. The 5' cap of the RNA molecule may be further modified by a 2'-O-Methyltransferase which results in the generation of a cap 1 structure (m7Gppp [m2'-O] N), which may further increases translation efficacy.

The nucleic acids may comprise one or more nucleotide analogs or modified nucleotides. As used herein, "nucleotide analog" or "modified nucleotide" refers to a nucleotide that contains one or more chemical modifications (e.g., substitutions) in or on the nitrogenous base of the nucleoside (e.g., cytosine (C), thymine (T) or uracil (U)), adenine (A) or guanine (G)). A nucleotide analog can contain further chemical modifications in or on the sugar moiety of the nucleoside (e.g., ribose, deoxyribose, modified ribose, modified deoxyribose, six-membered sugar analog, or open-chain sugar analog), or the phosphate. The preparation of nucleotides and modified nucleotides and nucleosides are well-known in the art, e.g. from U.S. Pat. Nos. 4,373,071, 4,458,066, 4,500,707, 4,668,777, 4,973,679, 5,047,524, 5,132,418, 5,153,319, 5,262,530, 5,700,642, and many modified nucleosides and modified nucleotides are commercially available.

Modified nucleobases which can be incorporated into modified nucleosides and nucleotides and be present in the RNA molecules include: m5C (5-methylcytidine), m5U (5-methyluridine), m6A (N6-methyladenosine), s2U (2-thiouridine), Um (2'-O-methyluridine), m1A (1-methyladenosine); m2A (2-methyladenosine); Am (2-1-O-methyladenosine); ms2m6A (2-methylthio-N6-methyladenosine); i6A (N6-isopentenyladenosine); ms2i6A (2-methylthio-N6isopentenyladenosine); io6A (N6-(cis-hydroxyisopentenyl)adenosine); ms2io6A (2-methylthio-N6-(cis-hydroxyisopentenyl) adenosine); g6A (N6-glycinylcarbamoyladenosine); t6A (N6-threonyl carbamoyladenosine); ms2t6A (2-methylthio-N6-threonyl carbamoyladenosine); m6t6A (N6-methyl-N6-threonylcarbamoyladenosine); hn6A(N6-hydroxynorvalylcarbamoyl adenosine); ms2hn6A (2-methylthio-N6-hydroxynorvalyl carbamoyladenosine); Ar(p) (2'-O-ribosyladenosine (phosphate)); I (inosine); m1I (1-methylinosine); m'Im (1,2'-O-dimethylinosine); m3C (3-methylcytidine); Cm (2T-O-methylcytidine); s2C (2-thiocytidine); ac4C (N4-acetylcytidine); f5C (5-fonnylcytidine); m5Cm (5,2-O-dimethyl cytidine); ac4Cm (N4acetyl2TOmethylcytidine); k2C (lysidine); m1G (1-methylguanosine); m2G (N2-methylguanosine); m7G (7-methylguanosine); Gm (2'-O-methylguanosine); m22G (N2,N2-dimethylguanosine); m2Gm (N2,2'-O-dimethylguanosine); m22Gm (N2,N2,2'-O-trimethylguanosine); Gr(p) (2'-O-ribosylguanosine (phosphate)); yW (wybutosine); o2yW (peroxywybutosine); OHyW (hydroxywybutosine); OHyW* (undermodified hydroxywybutosine); imG (wyosine); mimG (methylguanosine); Q (queuosine); oQ (epoxyqueuosine); galQ (galtactosyl-queuosine); manQ (mannosyl-queuosine); preQo (7-cyano-7-deazaguanosine); preQi (7-aminomethyl-7-deazaguanosine); G* (archaeosine); D (dihydrouridine); m5Um (5,2'-O-dimethyluridine); s4U (4-thiouridine); m5s2U (5-methyl-2-thiouridine); s2Um (2-thio-2'-O-methyluridine); acp3U (3-(3-amino-3-carboxypropyl)uridine); ho5U (5-hydroxyuridine); mo5U (5-methoxyuridine); cmo5U (uridine 5-oxyacetic acid); mcmo5U (uridine 5-oxyacetic acid methyl ester); chm5U (5-(carboxyhydroxymethyl)uridine)); mchm5U (5-(carboxyhydroxymethyl)uridine methyl ester); mcm5U (5-methoxycarbonyl methyluridine); mcm5Um (S-methoxycarbonylmethyl-2-O-methyluridine); mcm5s2U (5-methoxycarbonylmethyl-2-thiouridine); nm5s2U (5-aminomethyl-2-thiouridine); mnm5U (5-methylaminomethyluridine); mnm5s2U (5-methylaminomethyl-2-thiouridine); mnm5se2U (5-methylaminomethyl-2-selenouridine); ncm5U (5-carbamoylmethyl uridine); ncm5Um (5-carbamoylmethyl-2'-O-methyluridine); cmnm5U (5-carboxymethylaminomethyluridine); cnmm5Um (5-carboxymethylaminomethyl-2-L-Omethyluridine); cmnm5s2U (5-carboxymethylaminomethyl-2-thiouridine); m62A (N6,N6-dimethyladenosine); Tm (2'-O-methylinosine); m4C (N4-methylcytidine); m4Cm (N4,2-O-dimethylcytidine); hm5C (5-hydroxymethylcytidine); m3U (3-methyluridine); cm5U (5-carboxymethyluridine); m6Am (N6,T-O-dimethyladenosine); rn62Am (N6,N6,O-2-trimethyladenosine); m2'7G (N2,7-dimethylguanosine); m2'2'7G (N2,N2,7-trimethylguanosine); m3Um (3,2T-O-dimethyluridine); m5D (5-methyldihydrouridine); f5Cm (5-formyl-2'-O-methylcytidine); m1Gm (1,2'-O-dimethylguanosine); m'Am (1,2-O-dimethyl adenosine) irinomethyluridine); tm5s2U (S-taurinomethyl-2-thiouridine)); imG-14 (4-demethyl guanosine); imG2 (isoguanosine); ac6A (N6-acetyladenosine), hypoxanthine, inosine, 8-oxo-adenine, 7-substituted derivatives thereof, dihydrouracil, pseudouracil, 2-thiouracil, 4-thiouracil, 5-aminouracil, 5-($C_1$-$C_6$)-alkyluracil, 5-methyluracil, 5-($C_2$-$C_6$)-alkenyluracil, 5-($C_2$-$C_6$)-alkynyluracil, 5-(hydroxymethyl)uracil, 5-chlorouracil, 5-fluorouracil, 5-bromouracil, 5-hydroxycytosine, 5-($C_1$-$C_6$)-alkylcytosine, 5-methylcytosine, 5-($C_2$-$C_6$)-alkenylcytosine, 5-($C_2$-$C_6$)-alkynylcytosine, 5-chlorocytosine, 5-fluorocytosine, 5-bromocytosine, $N^2$-dimethylguanine, 7-deazaguanine, 8-azaguanine, 7-deaza-7-substituted guanine, 7-deaza-7-(C2-C6)alkynylguanine, 7-deaza-8-substituted guanine, 8-hydroxyguanine, 6-thioguanine, 8-oxoguanine, 2-aminopurine, 2-amino-6-chloropurine, 2,4-diaminopurine, 2,6-diaminopurine, 8-azapurine, substituted 7-deazapurine, 7-deaza-7-substituted purine, 7-deaza-8-substituted purine, hydrogen (abasic residue), m5C, m5U, m6A, s2U, W, or 2'-O-methyl-U. Many of these modified nucleobases and their corresponding ribonucleosides are available from commercial suppliers. See, e.g., WO 2011/005799.

Nucleic Acid-Based Vaccines

A composition as disclosed herein comprising a nucleic acid sequence which encodes a parasite MIF antigen may be a nucleic acid-based vaccine. A further composition comprising a nucleic acid sequence which encodes one or more additional parasite antigens may also be provided as a nucleic acid-based vaccine.

The nucleic acid may, for example, be RNA (i.e. an RNA-based vaccine) or DNA (i.e. a DNA-based vaccine, such as a plasmid DNA vaccine). In certain embodiments, the nucleic acid-based vaccine is an RNA-based vaccine. In certain embodiments, the RNA-based vaccine comprises a self-replicating RNA molecule. The self-replicating RNA molecule may be an alphavirus-derived RNA replicon.

Self-replicating RNA molecules are well known in the art and can be produced by using replication elements derived from, e.g., alphaviruses, and substituting the structural viral proteins with a nucleotide sequence encoding a protein of interest. A self-replicating RNA molecule is typically a +-strand molecule which can be directly translated after delivery to a cell, and this translation provides a RNA-dependent RNA polymerase which then produces both antisense and sense transcripts from the delivered RNA. Thus the delivered RNA leads to the production of multiple daughter RNAs. These daughter RNAs, as well as collinear subgenomic transcripts, may be translated themselves to provide in situ expression of an encoded antigen (i.e. a parasite MIF antigen), or may be transcribed to provide further transcripts with the same sense as the delivered RNA which are translated to provide in situ expression of the antigen. The overall result of this sequence of transcriptions is a huge amplification in the number of the introduced replicon RNAs and so the encoded antigen becomes a major polypeptide product of the cells.

One suitable system for achieving self-replication in this manner is to use an alphavirus-based replicon. These replicons are +-stranded RNAs which lead to translation of a replicase (or replicase-transcriptase) after delivery to a cell. The replicase is translated as a polyprotein which autocleaves to provide a replication complex which creates genomic −-strand copies of the +-strand delivered RNA. These −-strand transcripts can themselves be transcribed to give further copies of the +-stranded parent RNA and also to give a subgenomic transcript which encodes the antigen. Translation of the subgenomic transcript thus leads to in situ expression of the antigen by the infected cell. Suitable alphavirus replicons can use a replicase from a Sindbis virus, a Semliki forest virus, an eastern equine encephalitis virus, a Venezuelan equine encephalitis virus, etc. Mutant or wild-type virus sequences can be used e.g. the attenuated TC83 mutant of VEEV has been used in replicons [33].

In certain embodiments, the self-replicating RNA molecule described herein encodes (i) a RNA-dependent RNA polymerase which can transcribe RNA from the self-replicating RNA molecule and (ii) a parasite MIF antigen. The polymerase can be an alphavirus replicase e.g. comprising one or more of alphavirus proteins nsP1, nsP2, nsP3 and nsP4.

Whereas natural alphavirus genomes encode structural virion proteins in addition to the non-structural replicase polyprotein, in certain embodiments, the self-replicating RNA molecules do not encode alphavirus structural proteins. Thus, the self-replicating RNA can lead to the production of genomic RNA copies of itself in a cell, but not to the production of RNA-containing virions. The inability to produce these virions means that, unlike a wild-type alphavirus, the self-replicating RNA molecule cannot perpetuate itself in infectious form. The alphavirus structural proteins which are necessary for perpetuation in wild-type viruses are absent from self-replicating RNAs of the present disclosure and their place is taken by gene(s) encoding the immunogen of interest, such that the subgenomic transcript encodes the immunogen rather than the structural alphavirus virion proteins.

Thus a self-replicating RNA molecule useful with the invention may have two open reading frames. The first (5') open reading frame encodes a replicase; the second (3') open reading frame encodes an antigen. In some embodiments the RNA may have additional (e.g. downstream) open reading frames e.g. to encode further antigens or to encode accessory polypeptides.

In certain embodiments, the self-replicating RNA molecule disclosed herein has a 5' cap (e.g. a 7-methylguanosine). This cap can enhance in vivo translation of the RNA. In some embodiments the 5' sequence of the self-replicating RNA molecule must be selected to ensure compatibility with the encoded replicase.

A self-replicating RNA molecule may have a 3' poly-A tail. It may also include a poly-A polymerase recognition sequence (e.g. AAUAAA) near its 3' end.

Self-replicating RNA molecules can have various lengths but they are typically 5000-25000 nucleotides long. Self-replicating RNA molecules will typically be single-stranded. Single-stranded RNAs can generally initiate an adjuvant effect by binding to TLR7, TLR8, RNA helicases and/or PKR. RNA delivered in double-stranded form (dsRNA) can bind to TLR3, and this receptor can also be triggered by dsRNA which is formed either during replication of a single-stranded RNA or within the secondary structure of a single-stranded RNA.

The self-replicating RNA can conveniently be prepared by in vitro transcription (IVT). IVT can use a (cDNA) template created and propagated in plasmid form in bacteria, or created synthetically (for example by gene synthesis and/or polymerase chain-reaction (PCR) engineering methods). For instance, a DNA-dependent RNA polymerase (such as the bacteriophage T7, T3 or SP6 RNA polymerases) can be used to transcribe the self-replicating RNA from a DNA template. Appropriate capping and poly-A addition reactions can be used as required (although the replicon's poly-A is usually encoded within the DNA template). These RNA polymerases can have stringent requirements for the transcribed 5' nucleotide(s) and in some embodiments these requirements must be matched with the requirements of the encoded replicase, to ensure that the IVT-transcribed RNA can function efficiently as a substrate for its self-encoded replicase.

A self-replicating RNA can include (in addition to any 5' cap structure) one or more nucleotides having a modified nucleobase. A RNA used with the invention ideally includes only phosphodiester linkages between nucleosides, but in some embodiments it can contain phosphoramidate, phosphorothioate, and/or methylphosphonate linkages.

The self-replicating RNA molecule may encode a single heterologous polypeptide antigen (i.e. a parasite MIF antigen) or, optionally, two or more heterologous polypeptide antigens linked together in a way that each of the sequences retains its identity (e.g., linked in series) when expressed as an amino acid sequence. The heterologous polypeptides generated from the self-replicating RNA may then be produced as a fusion polypeptide or engineered in such a manner to result in separate polypeptide or peptide sequences.

The self-replicating RNA molecules described herein may be engineered to express multiple nucleotide sequences, from two or more open reading frames, thereby allowing co-expression of proteins, such as one, two or more parasite antigens (e.g. one, two or more parasite MIF antigens) together with cytokines or other immunomodulators, which can enhance the generation of an immune response. Such a self-replicating RNA molecule might be particularly useful, for example, in the production of various gene products (e.g., proteins) at the same time, for example, as a bivalent or multivalent vaccine.

If desired, the self-replicating RNA molecules can be screened or analyzed to confirm their therapeutic and prophylactic properties using various in vitro or in vivo testing methods that are known to those of skill in the art. For example, vaccines comprising self-replicating RNA molecule can be tested for their effect on induction of proliferation or effector function of the particular lymphocyte type of interest, e.g., B cells, T cells, T cell lines, and T cell clones. For example, spleen cells from immunized mice can be isolated and the capacity of cytotoxic T lymphocytes to lyse autologous target cells that contain a self-replicating RNA molecule that encodes a parasite MIF antigen. In addition, T helper cell differentiation can be analyzed by measuring proliferation or production of TH1 (IL-2 and IFN-γ) and/or TH2 (IL-4 and IL-5) cytokines by ELISA or directly in CD4+ T cells by cytoplasmic cytokine staining and flow cytometry.

Self-replicating RNA molecules that encode a parasite MIF antigen can also be tested for ability to induce humoral immune responses, as evidenced, for example, by induction of B cell production of antibodies specific for a parasite MIF antigen of interest. These assays can be conducted using, for example, peripheral B lymphocytes from immunized individuals. Such assay methods are known to those of skill in the art. Other assays that can be used to characterize the self-replicating RNA molecules can involve detecting expression of the encoded parasite MIF antigen by the target cells. For example, FACS can be used to detect antigen expression on the cell surface or intracellularly. Another advantage of FACS selection is that one can sort for different levels of expression; sometimes-lower expression may be desired. Other suitable method for identifying cells which express a particular antigen involve panning using monoclonal antibodies on a plate or capture using magnetic beads coated with monoclonal antibodies.

Suitable types of nucleic acid-based vaccine for use according to the present disclosure are described in references 34, 35 and 36.

The nucleic acid-based vaccine may comprise a viral or a non-viral delivery system. The delivery system (also referred to herein as a delivery vehicle) may have adjuvant effects which enhance the immunogenicity of the encoded parasite MIF antigen. For example, the nucleic acid molecule may be encapsulated in liposomes, non-toxic biodegradable polymeric microparticles or viral replicon particles (VRPs), or complexed with particles of a cationic oil-in-water emulsion. In some embodiments, the nucleic acid-based vaccine comprises a cationic nano-emulsion (CNE) delivery system or a lipid nanoparticle (LNP) delivery system. Alternatively, the nucleic acid-based vaccine may comprise viral replicon particles. In other embodiments, the nucleic acid-based vaccine may comprise a naked nucleic acid, such as naked RNA (e.g. mRNA), but delivery via LNPs is preferred.

In certain embodiments, the nucleic acid-based vaccine comprises a cationic nano-emulsion (CNE) delivery system. CNE delivery systems and methods for their preparation are described in reference 35. In a CNE delivery system, the nucleic acid molecule (e.g. RNA) which encodes the antigen is complexed with a particle of a cationic oil-in-water emulsion. Cationic oil-in-water emulsions can be used to deliver negatively charged molecules, such as an RNA molecule to cells. The emulsion particles comprise an oil core and a cationic lipid. The cationic lipid can interact with the negatively charged molecule thereby anchoring the molecule to the emulsion particles. Further details of useful CNEs can be found in references 35, 37 & 38 (the complete contents of all of which are incorporated by reference herein).

Thus, in a nucleic acid-based vaccine of the invention, an RNA molecule encoding a parasite MIF antigen may be complexed with a particle of a cationic oil-in-water emulsion. The particles typically comprise an oil core (e.g. a plant oil or squalene) that is in liquid phase at 25° C., a cationic lipid (e.g. phospholipid) and, optionally, a surfactant (e.g. sorbitan trioleate, polysorbate 80); polyethylene glycol can also be included. In some embodiments, the CNE comprises squalene and a cationic lipid, such as 1,2-dioleoyloxy-3-(trimethylammonio)propane (DOTAP). In some preferred embodiments, the delivery system is a non-viral delivery system, such as CNE, and the nucleic acid-based vaccine comprises a self-replicating RNA (mRNA). This may be particularly effective in eliciting humoral and cellular immune responses. Advantages also include the absence of a limiting anti-vector immune response and a lack of risk of genomic integration.

LNP delivery systems and non-toxic biodegradable polymeric microparticles, and methods for their preparation are described in references 34 and 36. LNPs are non-virion liposome particles in which a nucleic acid molecule (e.g. RNA) can be encapsulated. The particles can include some external RNA (e.g. on the surface of the particles), but at least half of the RNA (and ideally all of it) is encapsulated. Liposomal particles can, for example, be formed of a mixture of zwitterionic, cationic and anionic lipids which can be saturated or unsaturated, for example; DSPC (zwitterionic, saturated), DlinDMA (cationic, unsaturated), and/ or DMG (anionic, saturated). Preferred LNPs for use with the invention include an amphiphilic lipid which can form liposomes, optionally in combination with at least one cationic lipid (such as DOTAP, DSDMA, DODMA, DLinDMA, DLenDMA, etc.). A mixture of DSPC, DlinDMA, PEG-DMG and cholesterol is particularly effective. Other useful LNPs are disclosed in references 34 and 39-43 (the complete contents of all of which are incorporated by reference herein). In some embodiments, the LNPs are RV01 liposomes (references 34 and 36).

Antibodies

In one aspect, the invention relates to an antibody which specifically binds to a parasite MIF antigen, as disclosed herein. Preferably, the antibody specifically binds to a naturally occurring parasite MIF antigen.

An antibody that "specifically binds" to a parasite MIF antigen is an antibody that binds this antigen with greater affinity and/or avidity than it binds to other parasite or non-parasite antigens. For example, the antibody which specifically binds to a parasite MIF antigen may bind the parasite MIF antigen with greater affinity and/or avidity than it binds to HSA. Preferably, the antibody does not specifically bind to vertebrate MIF or a MIF antigen produced by the subject.

As used herein, the term "antibody" includes full-length or whole antibodies (i.e. antibodies in their substantially intact form), antibody fragments such as F(ab')2, F(ab) and Fab'-SH fragments, Fv fragments (non-covalent heterodimers), single-chain antibodies such as single chain Fv molecules (scFv) or those derived from camelids and sharks (e.g. heavy chain antibodies), single-domain antibodies (dAbs), diabodies, minibodies, oligobodies, etc. The term "antibody" does not imply any particular origin, and includes antibodies obtained through non-conventional processes, such as phage display. All of the antibodies will comprise the antigen binding site of a full-length or whole antibody and thus retain the ability of bind antigen. Thus, the term "antibody" includes antigen-binding fragments of full-length or whole antibodies. The antibody is ideally a monoclonal antibody, or, alternatively, may be polyclonal. The antibody may be chimeric, humanized (e.g. refs. 44 & 45), or fully human. In compositions of the invention, polyclonal antibody, comprising one or more antibodies which specifically bind to the parasite MIF antigen, may be used. In some preferred embodiments, the composition comprises polyclonal antibody, for example serum anti-parasite MIF antibody. The polyclonal antibody may comprise IgG (e.g. purified serum IgG). The antibody may comprise a neutralizing antibody (i.e. an antibody which neutralizes the biological effects of the parasite MIF in the subject).

The antibody is preferably provided in purified or substantially purified form. Typically, the antibody will be present in a composition that is substantially free of other polypeptides e.g. where less than 90% (by weight), usually less than 60% and more usually less than 50% of the composition is made up of other polypeptides.

The antibodies can be of any isotype (e.g. IgA, IgG, IgM i.e. an α, γ or μ heavy chain), but will generally be IgG. Within the IgG isotype, antibodies may be IgG1, IgG2, IgG3 or IgG4 subclass. The antibody may have a κ or a λ light chain.

Parasites

The present invention relates to treatment of parasitic infections using parasite MIF antigens. The parasite (i.e. the causative agent of the parasitic infection and the parasite from which the parasite MIF antigen is derived) may be an invertebrate parasite, for example protozoan or a helminth. The parasite may, for example, be a blood-borne parasite (i.e. a parasite having a life-cycle which involves a blood-borne stage). Parasites according to the invention necessarily express a MIF ortholog (i.e. a naturally occurring MIF polypeptide).

Parasitic protozoans include apicomplexan parasites, such as *Plasmodium* spp., *Toxoplasma* spp., *Eimeria* spp., *Babesia* spp., *Theileria* spp, *Neospora* spp and *Sarcocystis* spp. Other examples of protozoan parasites include hemoflagellates, such as *Leishmania* spp. and *Trypanosoma* spp., and other flagellated protozoans such as *Giardia* spp.

*Plasmodium* spp. include *Plasmodium falciparum, Plasmodium berghei* (e.g. strain ANKA), *Plasmodium yoelii, Plasmodium chabaudi, Plasmodium vivax, Plasmodium knowlesi, Plasmodium ovale, Plasmodium malariae*, and *Plasmodium vinckei. Toxoplasma* spp. include *Toxoplasma gondii. Eimeria* spp. include *Eimeria tenella* and *Eimeria acervulina. Babesia* spp. include *Babesia microti, Babesia divergens*, and *Babesia duncani. Theileria* spp. include *Theileria annulata, Theileria parva, Theileria equi* and *Theileria orientalis. Neospora* spp. include *Neospora caninum. Sarcosystis* spp. include *Sarcocystis neurona. Leishmania* spp. include *Leishmania major, Leishmania tropica, Leishmania aethiopica, Leishmania infantum* (or *Leishmania chagasi*), *Leishmania donovani, Leishmania amazonensis* and *Leishmania braziliensis. Trypanosoma* spp. include *Trypanosoma brucei* (subspecies gambiense, rhodesiense, or *brucei*), and *Trypanosoma cruzi. Giardia* spp. include *Giardia lamblia* (or *Giardia intestinalis*).

Parasitic helminths include nematodes (e.g. hookworm, whipworm, filariid, ascarid, strongyle and trichostrongyle nematodes), such as *Ancyclostoma* spp., *Necator* spp., *Brugia* spp., *Wuchereria* spp., *Loa* spp., *Mansonella* spp., *Trichinella* spp., *Trichuris* spp., *Ascaris* spp., *Anisakis* spp., *Dracunculus* spp., *Strongyloides* spp., *Haemonchus* spp., *Toxocara* spp., *Dictyocaulus* spp., *Ostertagia* spp., *Teladorsagia* spp, *Onchocerca* spp. and *Dirofilaria* spp. Further examples include *Acanthocheilonema* spp., *Aelurostrongylus* spp., *Angiostrongylus* spp., *Bunostomum* spp., *Dioctophyme* spp., *Dipetalonema* spp., *Lagochilascaris* spp., *Muellerius* spp., *Parafilaria* spp., *Parascaris* spp., *Protostrongylus* spp., *Setaria* spp., *Stephanofilaria* spp., *Strongylus* spp., *Thelazia* spp., *Capillaria* spp., *Chabertia* spp., *Cooperia* spp., *Enterobius* spp., *Nematodirus* spp., *Oesophagostomum* spp, and *Trichostrongylus* spp.

Other examples of helminthic parasites include trematodes, such as *Schistosoma* spp. and liver flukes such as *Fasciola* spp (e.g. *Fasciola hepatica*).

*Ancyclostoma* spp. include *Ancylostoma duodenale, Ancylostoma ceylanicum, Ancylostoma braziliense, Ancylostoma caninum, Ancylostoma pluridentatum*, and *Ancylostoma tubaeforme. Necator* spp. include *Necator americanus. Brugia* spp. include *Brugia malayi, Brugia timori* and *Brugia pahangi. Wuchereria* spp. include *Wuchereria bancrofti. Loa* spp. include *Loa* boa. *Mansonella* spp. include *Mansonella streptocerca, Mansonella perstans* and *Mansonella ozzardi. Trichinella* spp. include *Trichinella spiralis, Trichinella pseudospiralis, Trichinella nelsoni, Trichinella britovi, Trichinella murrelli*, and *Trichinella nativa. Trichuris* spp. include *Trichuris trichiura, Trichuris muris, Trichuris campanula, Trichuris suis, Trichuris ovis* and *Trichuris vulpis. Ascaris* spp. include *Ascaris lumbricoides*, and *Ascaris suum. Anisakis* spp. include *Anisakis simplex. Dracunculus* spp. include *Dracunculus medinensis*, and *Dracunculus insignis. Strongyloides* spp. include *Strongyloides stercoralis* and *Strongyloides papillosus. Onchocerca* spp. include *Onchocerca volvulus* and *Onchocerca tubingensis. Dirofilaria* spp. include *Dirofilaria immitis* and *Dirofilaria repens. Haemonchus* spp. include *Haemonchus contortus* and *Haemonchus placei. Toxocara* spp. include *Toxocara canis* and *Toxocara cati. Dictyocaulus* spp. include *Dictyocaulus viviparus* and *Dictyocaulus arnfieldi. Chabertia* spp. include *Chabertia ovina. Cooperia* spp. include *Cooperia curticei* and *Cooperia oncophora. Nematodirus* spp. include *Nematodirus spathiger* and *Nematodirus filicollis. Oesophagostomum* spp. include *Oesophagostomum columbianum* and *Oesophagostomum venulosum. Trichostrongylus* spp. include *Trichostrongylus axei, Trichostrongylus colubriformis* and *Trichostrongylus vitrinus*. Further parasitic nematodes include *Parastrongyloides trichosuri, Ostertagia ostertagi, Ostertagia trifurcata*, and *Teladorsagia circumcincta.*

*Schistosoma* spp. include *Schistosoma mansoni, Schistosoma haematobium, Schistosoma japonicum, Schistosoma mekongi, Schistosoma bovis, Schistosoma mattheei, Schistosoma margrebowiei, Schistosoma curassoni, Schistosoma rodhaini, Schistosoma indicum, Schistosoma intercalatum, Schistosoma malayensis, Schistosoma ovuncatum, Schistosoma nasale*, and *Schistosoma spindale. Fasciola* spp. include *Fasciola hepatica, Fasciola magna, Fasciola gigantica, Fasciola jacksoni.*

Reference 46 speculatively describes therapeutic compositions to protect animals from diseases caused by parasitic helminths which comprise parasitic helminth MIF protein, nucleic acids which hybridize under stringent conditions with a *Dirofilaria immitis* MIF gene or an *Onchocerca volvulus* MIF gene, and isolated antibodies that selectively bind to a parasitic helminth MIF protein. However, unlike the present disclosure, such therapeutic compositions are not substantiated with experimental evidence which establishes that such compositions would have a therapeutic effect.

Nonetheless, in some embodiments of the present invention, the parasite is not a parasitic helminth. In some embodiments, the parasite is not a parasitic nematode. In some embodiments, the parasite is not a filariid nematode worm. In some embodiments, in particular wherein the composition comprises a nucleic acid comprising a sequence which encodes a parasite MIF antigen, the parasite is not *Onchocerca volvulus* or *Dirofilaria immitis*. For example, in some embodiments the parasite MIF antigen (e.g. the parasite MIF antigen encoded by a nucleic acid of the composition) is not an *Onchocerca volvulus* MIF antigen or *Dirofilaria immitis* MIF antigen.

Reference 47 evaluated the immune response induced by DNA vaccines expressing *Trichinella spiralis* MCD-1, *T. spiralis* MIF or co-expressing *T. spiralis* MCD-1 and MIF, in BALB/c mice. Immunization with the vaccine co-expressing MCD-1 and MIF was followed by a small reduction in parasite burden but DNA vaccine expressing *T. spiralis* MIF did not protect mice against *T. spiralis* infection. In some embodiments of the present invention, the parasite is not *Trichinella spiralis*, in particular wherein the composition comprises a nucleic acid (and in particular DNA) comprising a sequence which encodes a parasite MIF antigen. In some embodiments the parasite MIF antigen (e.g. the parasite MIF antigen encoded by a nucleic acid of the composition) is not a *Trichinella spiralis* MIF antigen. In some embodiments, the composition and/or the parasite MIF antigen does not comprise a multi-cystatin-like domain protein, such as *T. spiralis* MCD-1.

Parasite infections may, for example, include malaria (e.g. cerebral malaria), toxoplasmosis, coccidiosis, babesiosis, theileriosis, trypanosomiasis, leishmaniasis, filariasis, elephantiasis, trichinosis, trichuriasis, ascariasis, dracunculiasis (guinea worm disease), equine protozoal myeloencephalitis (EPM), fasciolosis and schistosomiasis. Preferably, the methods and compositions disclosed herein are used to provide protective immunity against malaria.

The methods and compositions disclosed herein may be used to provide protective immunity against a single parasite infection, or co-infection by two or more different parasites. The two or more parasites may be two or more parasites selected from those listed herein. In some embodiments, at least one of the two or more different parasites is a *Plasmodium* parasite, such as a *Plasmodium falciparum* parasite.

Methods of Treatment and Medical Uses

The compositions disclosed herein may be used in a method for providing protective immunity against a parasite infection in a subject (e.g. a vertebrate) in need thereof, comprising the step of administering the composition (e.g. an immunologically effective amount of the composition) to the subject.

The invention also provides a composition as disclosed herein for use in providing protective immunity against a parasite infection in a subject.

In some embodiments, the composition provides protective immunity by generating a protective immune response against the parasite infection (e.g. active immunization), particularly in those embodiments where the composition comprises a nucleic acid comprising a sequence which encodes a parasite MIF antigen or comprises a parasite MIF antigen. Protective immunity may also be provided by administering to the subject an antibody which specifically binds the parasite MIF antigen (e.g. by passive immunization). Protective immunity may also be provided by administering to the subject parasite-responsive CD4 T cells isolated from a compatible host (preferably of the same species as the subject), wherein the host has been immunized with a composition of the invention: i.e. a composition which comprises an immunologically effective amount of (i) a nucleic acid comprising a sequence which encodes a parasite MIF antigen or (ii) a parasite MIF antigen (e.g. by adoptive transfer of CD4 T cells). The compatible host may have been immunized with the composition and exposed to the parasite or a parasite antigen to produce a parasite-responsive CD4 T cell population.

Administration of a composition of the invention to a subject (or compatible host) enables the subject (or host) to produce a parasite-responsive CD4 memory T cell population on exposure to the parasite or a parasite antigen. The parasite-responsive CD4 memory T cell population may confer "sterilizing" immunity (i.e. complete protective immunity) against re-infection.

Thus, also provided herein is a method of providing a subject with protective (e.g. sterilizing) immunity against parasite re-infection. The method may comprise: (i) administering a composition of the invention (e.g. a composition comprising a nucleic acid comprising a sequence which encodes a parasite MIF antigen) to the subject, and (ii) subsequently infecting the subject with the parasite or immunizing the subject with another parasite antigen (to produce a parasite-responsive CD4 T cell population). In step (ii), subsequent infection of a subject with the parasite might be deliberate in an animal study, but in humans it is preferred that this occurs via natural infection. Thus the method may be applied to a subject who is likely to be exposed to infection e.g. who lives in a malarial area, or who works with malaria patients, etc. Optionally (e.g. where the subject is infected with the parasite), these methods may further comprise curing the subject of the parasite infection, e.g. by administration of an agent which kills or attenuates the parasite, as described herein.

"Protective immunity" or a "protective immune response", as used herein, refers to immunity or eliciting an immune response against an infectious agent (e.g. a parasite), which is exhibited by a subject, that prevents or ameliorates an infection or reduces at least one symptom thereof. Specifically, induction of protective immunity or a protective immune response from administration of a composition of the invention is evident by elimination or reduction of the presence of one or more symptoms of the parasitic infection and/or an expansion of the parasite-responsive memory T cell population. As used herein, the term "immune response" refers to both the humoral immune response and the cell-mediated immune response. Preferably, the protective immunity provided by the invention is characterized by protective immunological memory (e.g. a protective memory T cell response) against the parasite. The protective immunity may be characterized by an effective parasite-responsive (e.g. *Plasmodium*-responsive) memory T cell population. In preferred embodiments, protective immunity is maintained (i.e. the protective effect does not decrease over the course of the parasite infection). Preferably, the subject can recover from the parasite infection. In preferred embodiments, treatment with a composition of the invention as described herein provides protective immunity against re-infection by the parasite. Protective immunity may be sterilizing immunity (i.e. complete protective immunity), whereby the protected subject can elicit an immune response which completely eliminates the infection.

A composition of the invention may therefore treat or prevent a parasite infection (or a disease associated therewith). In preferred embodiments, the disease is malaria. More particularly, the disease may be cerebral malaria.

The compositions disclosed herein may be used to induce a primary immune response and/or to boost an immune response.

Where a subject is treated in accordance with the present invention, the subject may have an expanded parasite-responsive (e.g. *Plasmodium*-responsive) memory T cell population relative to an untreated subject following parasite infection, particularly in those embodiments where the composition comprises a nucleic acid comprising a sequence which encodes a parasite MIF antigen or comprises a parasite MIF antigen. The parasite-responsive memory T cell population may comprise $CD4^+Ki67^+$ IL-7R$\alpha^+$ T cells. For example, the parasite-responsive memory T cells may comprise T memory cells ($CD4^+Ki67^+$ $CD62L^+$ IL-7R$\alpha^+$) and/or T effector memory cells ($CD4^+Ki67^+$ $CD62L^-$ IL-7R$\alpha^+$). The parasite-responsive memory T cell population may be expanded by at least 5%, at least 10%, at least 15%, at least 20%, at least 25%, at least 30%, at least 35%, at least 40%, at least 45%, at least 50% (e.g. relative to an untreated subject) following parasite infection.

Where a subject is treated in accordance with the present invention, the subject may have decreased IFN-γ levels relative to an untreated subject following parasite infection. For example, serum IFNγ levels may be decreased. IFN-γ production by inflammatory, terminal effector CD4 T cells may be decreased. IFN-γ levels may be assessed by specific ELISA. The decrease may be at least 10%, at least 20%, at least 30%, at least 40%, at least 50%, or at least 60% relative to an untreated subject following parasite infection.

A composition of the invention may be administered to a subject to allow the subject to develop and/or maintain sterilizing immunity to parasite infection. Protective immunity may be provided or augmented in an immunized subject following parasite infection or exposure to another parasite vaccine or antigen (e.g. an additional parasite antigen, as defined herein).

A composition of the invention may be used in a prime-boost vaccination regime. Protective immunity against a parasite infection according to the invention may be provided by administering a priming vaccine, comprising a composition of the invention, followed by a booster vaccine. The booster vaccine is different from the primer vaccine and comprises or encodes one or more additional (i.e. non-MIF) parasite antigens, as defined herein. The booster vaccine may, for example, comprise an attenuated form of the parasite to which protective immunity is to be provided. Preferably the priming and booster vaccines are administered less than about 16 weeks apart (e.g. less than about 8 weeks, 6 weeks, 4 weeks, 2 weeks or 1 week apart). As an alternative, two vaccines may be administered within 12 hours of each other, within 6 hours, within 3 hours, within 2 hours or within 1 hour of each other.

Where the composition of the invention comprises antibody which specifically binds to a parasite MIF antigen (anti-parasite MIF antibody), the composition may be used in a method of treating a parasite infection and/or a method of providing protective immunity against a parasite infection i.e. passive immunisation for therapeutic or prophylactic purposes. For example, the composition may be used in a method of treating (i.e. ameliorating) one or more symptoms of malaria (i.e. where the parasite is *Plasmodium*). The symptoms may be selected from headache, fever, shivering, joint pain, vomiting, hemolytic anemia, jaundice, hemoglobinuria, retinal damage, convulsions, encephalopathy, or one or more neurological symptoms, including abnormal posturing, nystagmus, conjugate gaze palsy (failure of the eyes to turn together in the same direction), opisthotonus, seizures, or coma. The malaria may be cerebral malaria.

In some embodiments, the anti-parasite MIF antibody is administered to an infected subject. The subject may be a recently-infected subject. For example, the antibody may be administered within 2 weeks of infection (e.g. within 10 days, 9 days, 8 days, 7 days, 6 days, 5 days, 4 days, 3 days, 2 days, 24 hrs). Alternatively, the subject may be at risk of infection. For example, the subject may be at risk of infection within 2 weeks of administration of the antibody (e.g. within 10 days, 9 days, 8 days, 7 days, 6 days, 5 days, 4 days, 3 days, 2 days, 24 hrs).

In certain embodiments, the subject is a vertebrate, e.g., a mammal, such as a human or a veterinary mammal (e.g. cat, dog, horse, cow, sheep, cattle, deer, goat, or pig) as the parasites covered herein may be problematic across a wide range of species.

The compositions of the invention can be formulated as vaccine compositions. Vaccines according to the invention may either be prophylactic (i.e. to prevent infection) or therapeutic (i.e. to treat infection), but will typically be prophylactic.

Compositions of the invention may be used to treat both children and adults. Where the vaccine is for prophylactic use, the human is preferably a child (e.g. a toddler or infant) or a teenager; where the vaccine is for therapeutic use, the human is preferably a teenager or an adult. A vaccine intended for children may also be administered to adults e.g. to assess safety, dosage, immunogenicity, etc.

Thus a human subject may be less than 1 year old, less than 5 years old, 1-5 years old, 5-15 years old, 15-55 years old, or at least 55 years old. Preferred patients for receiving the compositions are the elderly (e.g. ≥50 years old, ≥60 years old, and preferably ≥65 years), the young (e.g. ≤5 years old), hospitalised patients, healthcare workers, armed service and military personnel, pregnant women, the chronically ill, or immunodeficient patients. The compositions are not suitable solely for these groups, however, and may be used more generally in a population.

The subject may have previously been infected with and/or mounted an immune response against the parasite of interest. For example, the subject may have previously mounted an immune response against the parasite MIF antigen of interest. Alternatively, the subject may be immunologically naïve with respect to the parasite and/or the parasite MIF antigen.

By "immunologically effective amount", it is meant that the administration of that amount to a subject, either in a single dose or as part of a series, is effective for treatment or prevention of a parasite infection. This amount varies depending upon the health and physical condition of the individual to be treated, age, the taxonomic group of individual to be treated (e.g. human, non-human primate, etc.), the capacity of the individual's immune system to synthesise antibodies, the degree of protection desired, the formulation of the composition or vaccine, the treating doctor's assessment of the medical situation, the severity of the disease, the potency of the compound administered, the mode of administration, and other relevant factors. It is expected that the amount will fall in a relatively broad range that can be determined through routine trials.

A dose of a nucleic acid (e.g. a nucleic acid-based vaccine) may have ≤100 μg nucleic acid; e.g. from 10-100 μg, such as about 10 μg, 25 μg, 50 μg, 75 μg or 100 μg, but expression can be seen at much lower levels; e.g. using ≤1 μg/dose, ≤100 ng/dose, ≤10 ng/dose, ≤1 ng/dose, etc. Similarly, a dose of a protein antigen may have ≤100 μg protein; e.g. from 10-100 μg, such as about 10 μg, 25 μg, 50 μg, 75 μg or 100 μg. A dose of an antibody may have ≤1000 mg antibody or ≤500 mg antibody; e.g. from 1-1000 mg or 1-500 mg, such as about 10 mg, 20 mg, 50 mg, 100 mg, 200 mg, 300 mg, 400 mg, 500 mg, 600 mg, 700 mg, 800 mg or 900 mg. The antibody may be administered in a dose of about 0.1-10 mg/kg body weight.

Compositions of the invention will generally be administered directly to a subject. Direct delivery may be accomplished by parenteral injection (e.g. subcutaneously, intraperitoneally, intravenously, intramuscularly, intradermally, or to the interstitial space of a tissue). Alternative delivery routes include rectal, oral (e.g. tablet, spray), buccal, sublingual, vaginal, topical, transdermal or transcutaneous, intranasal, ocular, aural, pulmonary or other mucosal administration. Intradermal and intramuscular administration are two preferred routes. Injection may be via a needle (e.g. a hypodermic needle), but needle-free injection may alternatively be used. A typical intramuscular dose is 0.5 ml.

One way of checking efficacy of therapeutic treatment involves monitoring parasite infection after administration of the compositions disclosed herein. One way of checking efficacy of prophylactic treatment involves monitoring immune responses, systemically (such as monitoring the level of IgG1 and IgG2a production) and/or mucosally (such as monitoring the level of IgA production), against the antigen. Typically, antigen-specific serum antibody responses are determined post-immunization but pre-challenge whereas antigen-specific mucosal antibody responses are determined post-immunization and post-challenge.

Another way of assessing the immunogenicity of the compositions disclosed herein is to express the parasite MIF antigen recombinantly for screening patient sera or mucosal secretions by immunoblot and/or microarrays. A positive reaction between the parasite MIF antigen and the patient sample indicates that the patient has mounted an immune response to the antigen. This method may also be used to identify immunodominant antigens and/or epitopes within protein antigens.

The efficacy of the compositions can also be determined in vivo by challenging appropriate animal models of the parasite infection of interest.

Dosage can be by a single dose schedule or a multiple dose schedule (i.e. two or more doses). Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.). In one embodiment, two or more doses are administered about 3 weeks apart.

Where multiple doses (i.e. two or more doses) of a composition of the invention are administered to a subject, the composition used for each dose may be independently selected from a composition which comprises: (i) a nucleic acid comprising a sequence which encodes a parasite MIF antigen; (ii) a parasite MIF antigen; and (iii) an antibody which specifically binds to a parasite MIF antigen. The composition administered in a first dose (the first dose composition) may be a composition which comprises any of (i), (ii) and/or (iii) and the composition administered in a second dose (the second dose composition) may be a composition which comprises any of (i), (ii) and/or (iii). The composition in each of the two or more doses may be the same (e.g. a first dose of (i) followed by a second dose of (i), or a first dose of (ii) followed by a second dose of (ii)) or may be different (e.g. a first dose of (i) followed by a second dose of (ii), or a first dose of (ii) followed by a second dose of (i)). In each of (i), (ii) and (iii), in each dose, the parasite MIF antigen may be the same parasite MIF antigen.

Pharmaceutical Compositions

The invention provides compositions comprising (i) a nucleic acid comprising a sequence which encodes a parasite MIF antigen; (ii) a parasite MIF antigen; or (iii) an antibody which specifically binds to a parasite MIF antigen. The composition may be a pharmaceutical composition, for example a vaccine composition. Accordingly, the composition may also comprise a pharmaceutically acceptable carrier. Where the composition comprises a nucleic acid comprising a sequence which encodes a parasite MIF antigen (e.g. nucleic acid-based vaccine), the composition may also comprise a delivery system, as described herein.

A "pharmaceutically acceptable carrier" includes any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, sucrose, trehalose, lactose, and lipid aggregates (such as oil droplets or liposomes). Such carriers are well known to those of ordinary skill in the art. The compositions may also contain a pharmaceutically acceptable diluent, such as water, saline, glycerol, etc. Additionally, auxiliary substances, such as wetting or emulsifying agents, pH buffering substances, and the like, may be present. Sterile pyrogen-free, phosphate-buffered physiologic saline is a typical carrier. A thorough discussion of pharmaceutically acceptable excipients is available in ref. 48.

Pharmaceutical compositions may include the particles in plain water (e.g. w.f.i.) or in a buffer e.g. a phosphate buffer, a Tris buffer, a borate buffer, a succinate buffer, a histidine buffer, or a citrate buffer. Buffer salts will typically be included in the 5-20 mM range.

Pharmaceutical compositions may have a pH between 5.0 and 9.5 e.g. between 6.0 and 8.0.

Compositions may include sodium salts (e.g. sodium chloride) to give tonicity. A concentration of 10±2 mg/ml NaCl is typical e.g. about 9 mg/ml.

Compositions may include metal ion chelators. These can prolong RNA stability by removing ions which can accelerate phosphodiester hydrolysis. Thus a composition may include one or more of EDTA, EGTA, BAPTA, pentetic acid, etc. Such chelators are typically present at between 10-500 μM e.g. 0.1 mM. A citrate salt, such as sodium citrate, can also act as a chelator, while advantageously also providing buffering activity.

Pharmaceutical compositions may have an osmolality of between 200 mOsm/kg and 400 mOsm/kg, e.g. between 240-360 mOsm/kg, or between 290-310 mOsm/kg.

Pharmaceutical compositions may include one or more preservatives, such as thiomersal or 2-phenoxyethanol. Mercury-free compositions are preferred, and preservative-free vaccines can be prepared.

Pharmaceutical compositions are preferably sterile.

Pharmaceutical compositions may be non-pyrogenic e.g. containing <1 EU (endotoxin unit, a standard measure) per dose, and preferably <0.1 EU per dose.

Pharmaceutical compositions may be gluten free.

Pharmaceutical compositions may be prepared in unit dose form. In some embodiments a unit dose may have a volume of between 0.1-1.0 ml e.g. about 0.5 ml.

The compositions may be prepared as injectables, either as solutions or suspensions. The composition may be prepared for pulmonary administration e.g. by an inhaler, using a fine spray. The composition may be prepared for nasal, aural or ocular administration e.g. as spray or drops. Injectables for intramuscular administration are typical.

The invention also provides a delivery device (e.g. syringe, nebuliser, sprayer, inhaler, dermal patch, etc.) containing a pharmaceutical composition of the invention. This device can be used to administer the composition to a subject (e.g. a vertebrate subject).

A composition of the present disclosure may also comprise, or be administered in conjunction with, one or more adjuvants (e.g. vaccine adjuvants), in particular where the composition comprises an immunologically effective amount of a parasite MIF antigen.

Adjuvants which may be used in compositions of the invention include, but are not limited to:

(A) Mineral-containing compositions, for example aluminium and calcium salts, such as aluminium phosphates. (B) Oil emulsions, for example squalene-in-water emulsions, such as MF59 or AS03. Complete Freund's adjuvant (CFA) and incomplete Freund's adjuvant (IFA) may also be used. (C) Saponin formulations. (D) Virosomes and virus-like particles (VLPs). (E) Bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof. (F) Human immunomodulators, for example cytokines, such as interleukins, interferons, macrophage colony stimulating factor, and tumor necrosis factor. (G) Bioadhesives and mucoadhesives, such as esterified hyaluronic acid microspheres, cross-linked derivatives of poly(acrylic acid), polyvinyl alcohol, polyvinyl pyrollidone, polysaccharides and carboxymethylcellulose. (H) Microparticles, for example particles of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB). (I) Liposomes. (J) Polyoxyethylene ether and polyoxyethylene ester formulations. (K) Polyphosphazene (PCPP). (L) Muramyl peptides. (M) Imidazoquinolone compounds, for example Imiquamod and its homologues.

The use of an aluminium hydroxide or aluminium phosphate adjuvant is particularly preferred, and antigens are generally adsorbed to these salts. Alternatively, MF59, AS01 or AS03 may be used as the adjuvant.

Exemplary adjuvants also include human TLR7 agonists, such as a compound of formula (K). These agonists are discussed in detail in reference 49:

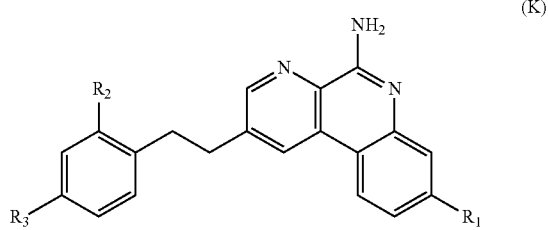

wherein:
$R^1$ is H, $C_1$-$C_6$alkyl, —$C(R^5)_2$OH, -$L^1R^5$, -$L^1R^6$, -$L^2R^5$, -$L^2R^6$, —$OL^2R^5$, or -$OL^2R^6$;
$L^1$ is —C(O)— or —O—;
$L^2$ is $C_1$-$C_6$alkylene, $C_2$-$C_6$alkenylene, arylene, heteroarylene or —$((CR^4R^4)_pO)_q(CH_2)_p$—, wherein the $C_1$-$C_6$alkylene and $C_2$-$C_6$alkenylene of $L^2$ are optionally substituted with 1 to 4 fluoro groups;
each $L^3$ is independently selected from $C_1$-$C_6$alkylene and —$((CR^4R^4)_pO)_q(CH_2)_p$—, wherein the $C_1$-$C_6$alkylene of $L^3$ is optionally substituted with 1 to 4 fluoro groups;
$L^4$ is arylene or heteroarylene;
$R^2$ is H or $C_1$-$C_6$alkyl;
$R^3$ is selected from $C_1$-$C_4$alkyl, -$L^3R^5$, -$L^1R^5$, -$L^3R^7$, -$L^3L^4L^3R^7$, -$L^3L^4R^5$, -$L^3L^4L^3R^5$, —$OL^3R^5$, —$OL^3R^7$, —$OL^3L^4R^7$, —$OL^3L^4L^3R^7$, —$OR^8$, —$OL^3L^4R^5$, —$OL^3L^4L^3R^5$ and —$C(R^5)_2$OH;
each $R^4$ is independently selected from H and fluoro;
$R^5$ is —$P(O)(OR^9)_2$,
$R^6$ is —$CF_2P(O)(OR^9)_2$ or —$C(O)OR^{10}$;
$R^7$ is —$CF_2P(O)(OR^9)_2$ or —$C(O)OR^{10}$;
$R^8$ is H or $C_1$-$C_4$alkyl;
each $R^9$ is independently selected from H and $C_1$-$C_6$alkyl;
$R^{10}$ is H or $C_1$-$C_4$alkyl;
each p is independently selected from 1, 2, 3, 4, 5 and 6, and
q is 1, 2, 3 or 4.

A TLR7 agonist, such as a TLR7 agonist of formula (K), may be adsorbed to an insoluble aluminium salt (e.g. to form an adsorbed complex for adjuvanting immunogens). Useful aluminium salts include, but are not limited to, aluminium hydroxide and aluminium phosphate adjuvants. Aluminium salts which include hydroxide ions are preferred for use with the invention as these hydroxide ions can readily undergo ligand exchange with compounds of formula (K). Thus preferred salts for adsorption of TLR agonists are aluminium hydroxide and/or aluminium hydroxyphosphate. These have surface hydroxyl moieties which can readily undergo ligand exchange with phosphorus-containing groups (e.g. phosphates, phosphonates) to provide stable adsorption. In an exemplary embodiment, an aluminium hydroxide adjuvant is used. Alternatively, a TLR7 agonist, such as a TLR7 agonist of formula (K) may not be adsorbed to an insoluble aluminium salt.

Phosphorous-containing adjuvants used with the invention may exist in a number of protonated and deprotonated forms depending on the pH of the surrounding environment, for example the pH of the solvent in which they are dissolved. Therefore, although a particular form may be illustrated, it is intended that these illustrations are merely representative and not limiting to a specific protonated or deprotonated form. For example, in the case of a phosphate group, this has been illustrated as —$OP(O)(OH)_2$ but the definition includes the protonated forms [$OP(O)(OH_2)(OH)$]$^+$ and —[$OP(O)(OH)_2$]$^{2+}$ that may exist in acidic conditions and the deprotonated forms [$OP(O)(OH)(O)$]$^-$ and [$OP(O)(O)_2$]$^{2-}$ that may exist in basic conditions.

Combinations of one or more of the adjuvants identified above may also be used with the invention.

Sequence Identity

Identity or homology with respect to a sequence is defined herein as the percentage of amino acid residues in the candidate sequence that are identical with the reference amino acid sequence after aligning the sequences and introducing gaps, if necessary, to achieve the maximum percent sequence identity, and not considering any conservative substitutions as part of the sequence identity.

Sequence identity can be determined by standard methods that are commonly used to compare the similarity in position of the amino acids of two polypeptides. Using a computer program such as BLAST or FASTA, two polypeptides are aligned for optimal matching of their respective amino acids (either along the full length of one or both sequences or along a pre-determined portion of one or both sequences). The programs provide a default opening penalty and a default gap penalty, and a scoring matrix such as PAM 250 [a standard scoring matrix; see Dayhoff et al., in Atlas of Protein Sequence and Structure, vol. 5, supp. 3 (1978)] can be used in conjunction with the computer program. For example, the percent identity can then be calculated as: the total number of identical matches multiplied by 100 and then divided by the sum of the length of the longer sequence within the matched span and the number of gaps introduced into the shorter sequences in order to align the two sequences.

General

The term "comprising" encompasses "including" as well as "consisting" e.g. a composition "comprising" X may consist exclusively of X or may include something additional e.g. X+Y.

The term "about" in relation to a numerical value x is optional and means, for example, x+10%.

Where the present disclosure refers to a sequence by reference to a UniProt or Genbank accession code, the sequence referred to is the current version at the filing date of the present application.

BRIEF DESCRIPTION OF DRAWINGS

FIG. 1A shows % CD4+ Ki67+. FIG. 1B shows B-bet MFI. FIG. 1C shows % PbA responding CD4 T cells. FIG. 1D shows IGN-γ MFI.

(FIG. 5A) a scheme for RNA/PbMIF CNE and RNA/GFP CNE vaccination, first parasite challenge, cure (CQ), and second parasite challenge; (FIG. 5B) Plasmodium parasitemia over 7 days following first parasite challenge (days 35 to 42); and (FIG. 5C) serum IFNγ levels on day 5 post-infection. *P<0.05, **P<0.01 Mann-Whitney U, n=15 per group.

FIG. 8A shows percentages of individual T cell phenotypes at 7 days after first infection. FIG. 8B shows percentages of individual T cell phenotypes at 7 days after second infection. FIG. 8C shows percentages of Tmem cells which are PD-1+ (indicating T cell exhaustion). *P<0.05, **P<0.01 Mann-Whitney U.

FIGS. 10A-E show that passive transfer of IgG from PbMIF immunized and blood-stage infected mice provides partial protection in both BALB/c and cerebral malaria-sensitive C57BL/6 Mice. (FIG. 10A) IgG isolated from GFP (control) or PbMIF immunized and PbA-infected mice was administered i.p. to naïve BALB/c or C57BL/6 mice and followed by PbA infection. (FIG. 10B) Parasitemia and (FIG. 10C) Kaplan-Meyer survival analysis of BALB/c mice administered immune IgG. p values were generated using a Long-rank test and data are from two independent experiments with 5 mice per group (*p<0.05, p<0.01). (FIG. 10D) Kaplan-Meyer survival plots and (FIG. 10E) ECM (Experimental Cerebral Malaria) score of C57BL/6 mice administered immune IgG and infected with PbA. Statistical p values were generated using a Long-rank test (p<0.01) and data are representative of two independent experiments n=10 mice per group.

FIGS. 11A-G shows that adoptively transferred CD4 T cells from PbMIF immunized mice confer protection to homologous challenge. (FIG. 11A) Immunized CD45.2 BALB/c mice were infected with $10^6$ PbA-iRBCs and treated with chloroquine on days 7-12. Four weeks later, the mice were re-infected with PbA and splenocytes isolated 7 days after infection, incubated with chloroquine to eliminate residual Plasmodium, and labeled with CFSE. Purified CD4 T cells ($2 \times 10^7$) then were transferred into naïve CD45.1 BALB/c mice and infected 3 days later with $10^6$ PbA-iRBCs. (FIG. 11B) Parasitemia in mice adoptively transferred with CD4 T cells from GFP (○) or PbMIF (●) immunized mice (*p<0.05, # p<0.001, by two-way ANOVA). The graph shows % parasitemia against days post-infection. (FIG. 11C) Representative CFSE dilution histogram of adoptively transferred (CD45.2) CD4 T cells from GFP or PbMIF immunized donors, (FIG. 11D) enumeration of recovered CD45.2 CD4 T cells, and (FIG. 11E) proliferation response of transferred CD4 T cells in CD45.1 recipients 7 days after infection. (FIG. 11F) Percent of proliferating CD45.2 CD4 T cells (CFSE$^{lo}$) producing IFNγ after stimulation ex vivo with PbA-iRBC lysates. (FIG. 11G) Mean fluorescence intensity of PD-1 in PbA-responsive CD45.2 CD4 T cells (CFSE$^{lo}$) from GFP (control) or PbMIF immunized donors. Results are from two separate experiments with 4 mice per group (*p<0.05, **p<0.01 by Mann-Whitney test.)

MODES FOR CARRYING OUT THE INVENTION

Figure 1A:
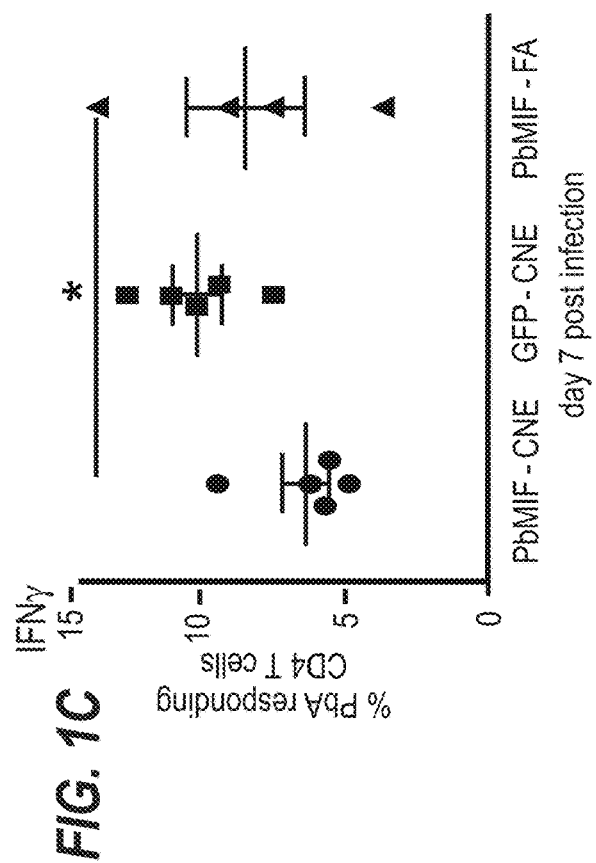
FIGS. 1A-1D show malaria-specific T cell responses in mice immunized with: RNA encoding PbMIF in a CNE delivery vehicle (PbMIF-CNE); RNA encoding GFP in a CNE delivery vehicle (GFP-CNE); or mice immunized with PbMIF protein with Freund's adjuvant (PbMIF-FA); at 7 days after Plasmodium infection on day 40 post-immunization. *P<0.05.

Example 1: Immunization Using P. berghei MIF, Followed by Parasite Challenge Groups of 5 female BALB/c mice aged 8-10 weeks were immunized with: (1) RNA encoding P. berghei MIF (Pb-MIF) in an LNP delivery vehicle (RV01, see references 34 and 36); (2) RNA encoding PbMIF in a CNE delivery vehicle (comprising squalene and DOTAP, as described in reference 35); (3) RNA encoding GFP in a CNE delivery vehicle; or (4) intraperitoneal (i.p.) injection of PbMIF protein with Freund's adjuvant, as set out in Table 1. Immunizations were carried out on day 0 and day 21.

TABLE 1

| Group | Antigen | Delivery system | Adjuvant | Dose | # animals/group |
|---|---|---|---|---|---|
| 1 | RNA/PbMIF | LNP | — | 1 µg | 5 |
| 2 | RNA/PbMIF | CNE | — | 15 µg | 5 |
| 3 | RNA/GFP | CNE | — | 15 µg | 5 |
| 4 | PbMIF Protein | i.p. | FCA/FIA | 10/5 µg | 5 |

Blood samples were taken from immunized mice on day 14 and day 35 (14 days after boosting) and total serum anti-PbMIF IgG titers were measured by anti-PbMIF ELISA assay. Immunized mice were challenged on day 38-40 by i.p.

injection of $10^6$ *P. berghei* ANKA (PbA)-infected red blood cells (RBCs). Mouse weights over time (from day 0 to day 40) and clinical appearance were also assessed for the mice in each experimental group.

Serum Anti-PbMIF IgG Titers from Immunized Mice and Tolerability to the Vaccine

IgG titers were measured 14 days after the first immunization and 14 days after the second boosting immunization. Anti-PbMIF ELISA assays were performed as follows: 96 well plates were coated overnight with 100 ng/ml of recombinant PbMIF. After blocking for 1 hr at room temperature, serial dilutions of sera were incubated for 2 hrs and total bound IgG was detected with a rabbit anti-mouse IgG coupled to horseradish peroxidase (HRP). 3,3',5,5'-Tetramethylbenzidine (TMB) was used as substrate. The reaction was stopped with acid and the OD reading performed at 450 nm.

Immunization with PbMIF self-replicating RNA vaccine or PbMIF protein (Groups 1, 2 and 4) elicited primary and secondary humoral antibody responses to PbMIF. No significant responses were observed in control mice treated with RNA/GFP CNE (Group 3). Secondary responses were observed in 80% of mice treated with RNA/PMIF CNE (Group 2) and 60% of mice treated with RNA/PMIF LNP (Group 1), with comparable titers. Primary responses in Groups 1 and 2 were ~100-fold less and secondary responses in Groups 1 and 2 were ~1000-fold less than mice treated with PMIF protein FCA/FIA (Group 4).

Mice tolerated immunization well, with no changes in clinical appearance (clinical observation q3d) and no reductions in weight among the different experimental groups from day 0 to day 40.

Impact of PbMIF Immunization on Malaria-Specific T Cell Responses

Groups 2, 3 and 4 were selected for study. Immunized mice were challenged on day 40 by i.p. injection of $10^6$ PbA-infected RBCs. On day 7 post-infection, splenocytes were isolated and stimulated ex vivo by culturing with infected red blood cell lysates in the presence of anti-CD3/CD28 beads and brefeldin A for 6 hrs. Intracellular cytokine staining was then performed. The following antibodies were used to study CD4 T cell IFN-γ production, T cell activation (CD11a) and T cell differentiation (T-bet): Ki67 FITC, CD45.2 PerCP-Cy5.5, IFN-γ PE-Cy7, CD4 Alexa 700, CD11a eFluor 405, T-bet Alexa 647 (Life Technologies). PbA-responsive CD4 T cells are defined as CD45.2+, Ki67+, CD4+. Stained cells were analysed by flow cytometry.

Figure 1B:
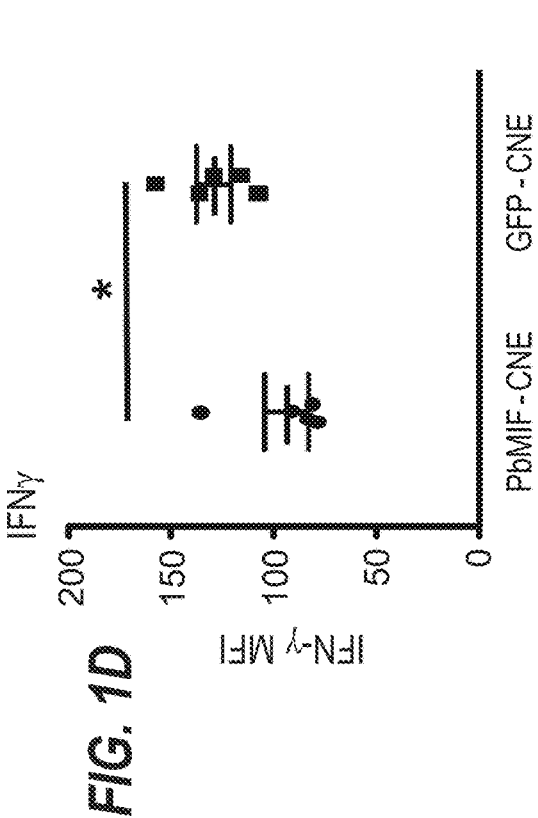
Figure 1C:
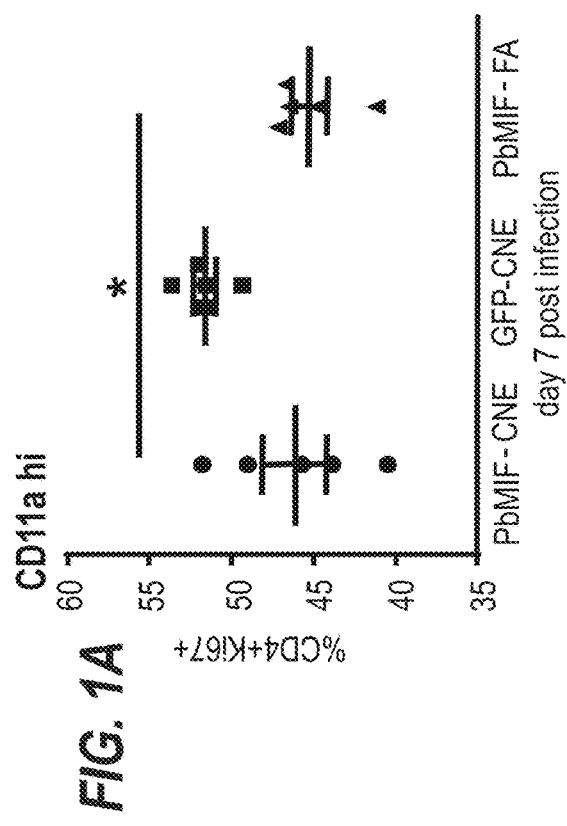
Figure 1D:
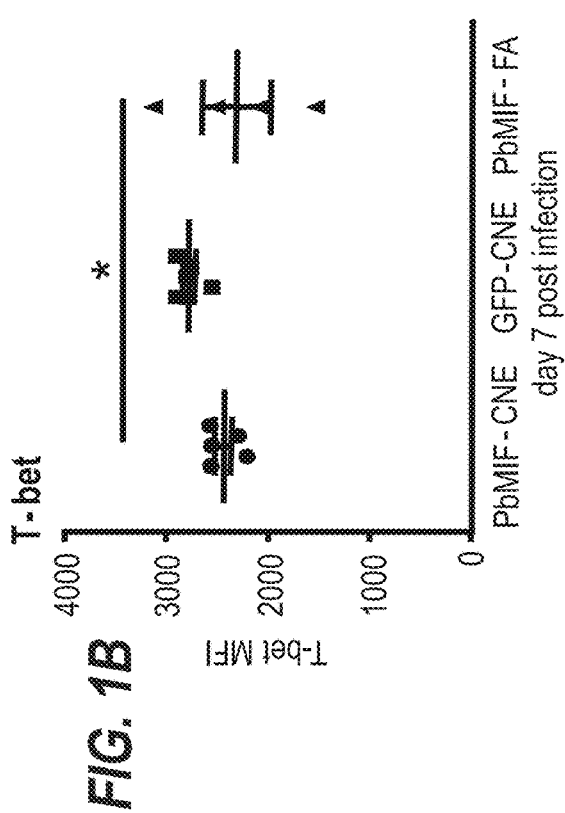

On day 7 post-infection, PbMIF immunized mice (Groups 2 and 4) showed a stronger T cell proliferative response to *P. berghei* parasites (higher CD4+Ki67+ cells) a stronger memory CD4 T cell response to parasites, as indicated by lower CD11a and lower T-bet (FIGS. 1A and 1B) and fewer inflammatory, terminal effector IFN-γ producing T cells (FIGS. 1C and 1D) than control mice (Group 3).

For example, flow cytometry showed that 5.26% of splenic CD4 T cells from RNA/PMIF CNE (Group 2) immunized mice were inflammatory, terminal effector IFN-γ-producing CD4 T cells (labelled with antiCD4 and stained for IFN-γ with an anti-IFN-γ antibody), compared to 11.1% of splenic CD4 T cells from control RNA/GFP CNE (Group 3) immunized mice (using pooled cells from 5 mice per group).

Further studies have shown a >65% increase in the number of *Plasmodium*-responsive memory CD4 T cells (CD62L+IL7Rα+) and effector memory CD4 T cell precursors (CD62L-IL7Rα+), as well as a 20% reduction in the expression of the exhaustion marker PD-1 in PbMIF-CNE immunized mice compared to GFP-CNE control mice at day 7 post-infection (n=5 per group, based on two separate experiments), suggesting a relative preservation of the memory response in the PbMIF immunized mice versus the control group. It has also been shown that, at day 7 post-infection, the number of *Plasmodium*-responsive follicular helper CD4 T cells ($T_{FH}$ cells—CD49d$^{hi}$CD11a$^{hi}$CXCR5$^{hi}$ CD4) was 50% greater in PbMIF-CNE immunized mice compared to GFP-CNE control mice. Consistent with this observed increase in the population of $T_{FH}$ cells, there was a corresponding enhancement in splenic B cell numbers, with a 30% increase in (CD19$^+$B220$^+$) B cells and a greater than doubling of the B cell plasmablast population (CD19$^{lo}$B220$^{lo}$CD138$^{hi}$IgD$^-$). Thus, PbMIF immunization is associated with an improvement in the host $T_{FH}$ and B cell responses.

Assessment of the Neutralization Activity of PbMIF RNA Vaccinations on *P. berghei* Parasitemia and Spleen Parasite Content On day 7 post-infection, parasitemia was also studied in immunized, challenged mice from Groups 2 and 3. Parasite burden was measured by quantitative PCR detection of *P. berghei* 18S rRNA copies/μL of peripheral blood, and splenic parasite burden was measured by expression of 18S rRNA relative to host GAPDH.

Figure 2A:
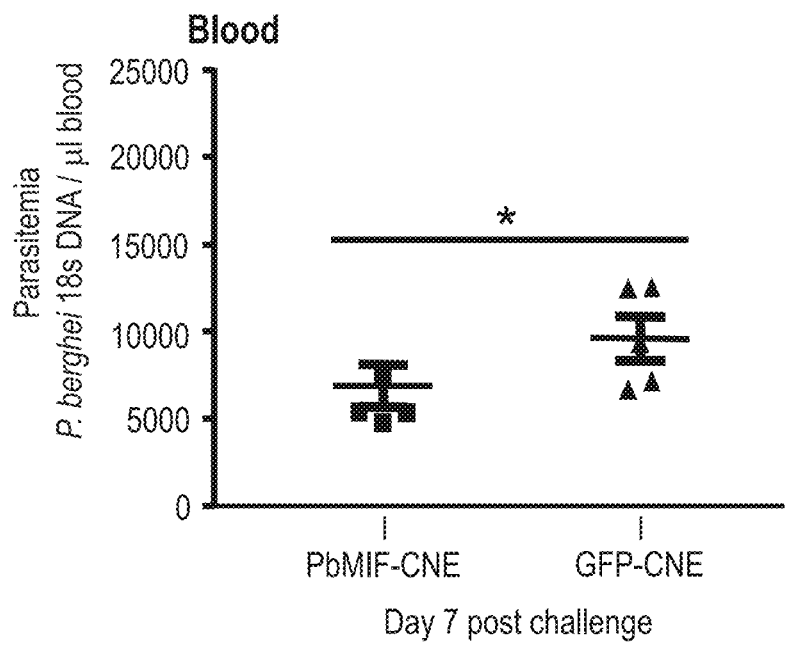
FIGS. 2A-B show neutralization activity of PbMIF immunization on (FIG. 2A) Plasmodium parasitemia and (FIG. 2B) spleen parasite content at 7 days post-infection. *P<0.05
Figure 2B:
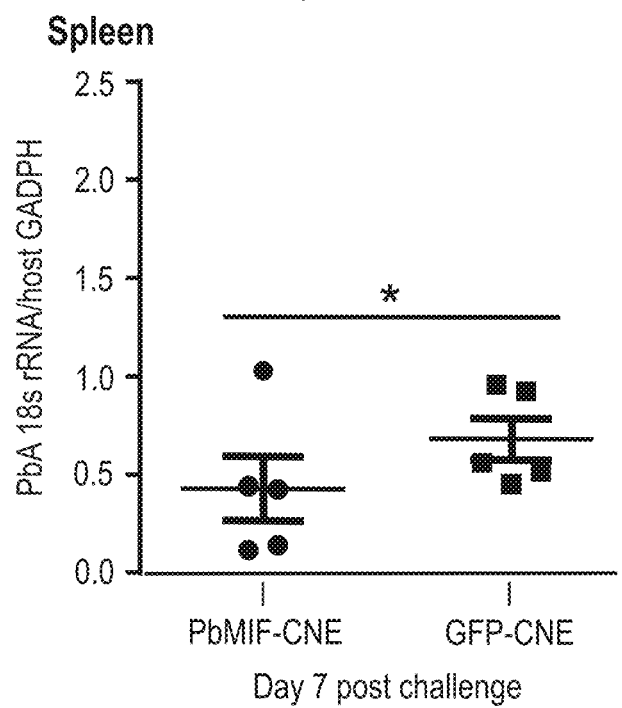

As shown in FIG. 2, PbMIF-CNE immunization was associated with a significant reduction in parasitemia (30%) and spleen parasite content upon challenge with lethal *P. berghei* infection.

Parasitemia and Survival During First Infection

In a separate experiment, BALB/c mice previously immunized with the RNA/PbMIF-CNE vaccine or GFP-CNE were infected with PbA and the parasitemia followed by FACS. Parasitemia was significantly reduced in the RNA/PbMIF-CNE-immunized mice compared to GFP-CNE-immunized control mice. While there was no initial difference in parasitemia between the two groups, there was a more rapid increase in parasitemia after day 5 in the control (GFP-CNE) group, which became moribund on day 21. By contrast, the PbMIF immunized mice showed better control of parasitemia during the first 15 days of infection. Survival was also monitored for up to 30 days post-infection and RNA/PbMIF-CNE-immunized mice showed a 37% prolongation in mean survival time compared to GFP-CNE-immunized control mice.

Conclusions (1)

PbMIF protein and self-replicating RNA vaccines are well-tolerated and produce a primary and secondary humoral antibody response in BALB/c mice.

RNA/PbMIF immunization (with CNE) neutralized *Plasmodium* PbMIF activity, and enhanced CD4 T cell memory differentiation. In addition, the neutralization of PbMIF activity significantly reduced parasitemia and parasite content of spleens and significantly improved mean survival times in infected mice. Thus, PbMIF immunization confers at least partial protection to first challenge infection.

Example 2: Immunization Using *P. Berghei* MIF in CNE RNA Delivery Vehicle, Followed by Parasite Challenge, Cure and Re-Challenge Example 2 differs from Example 1 in the addition of a first parasite challenge, followed by cure to expand the *Plasmodium*-specific memory T cell population.

Groups of 15 female BALB/c mice aged 8-10 weeks were immunized with: (1) RNA encoding PbMIF in a CNE delivery vehicle; and (2) RNA encoding GFP in a CNE delivery vehicle, as set out in Table 2. Immunizations were carried out on day 0 and day 21.

TABLE 2

| Group | Antigen | Delivery system | Adjuvant | Dose | # animals/group |
|---|---|---|---|---|---|
| 1 | RNA/PbMIF | CNE | — | 15 µg | 15 |
| 2 | RNA/GFP | CNE | — | 15 µg | 15 |

Blood samples were taken from immunized mice on days 14 and 35 and total serum anti-PbMIF IgG titers were measured by anti-PbMIF ELISA assay. Immunized mice were challenged on day 35 by i.p. injection of $10^6$ PbA-infected RBCs. This was followed by cure with chloroquine (CQ) (50 mg/kg/day) on days 7-10 post-challenge (days 42-45).

Readouts Following First Challenge:
Parasitemia; days 3, 5 and 7 post-challenge (days 38, 40, 42).
Total serum anti-PbMIF Ig and total anti-*Plasmodium* Ig after CQ cure (before $2^{nd}$ challenge, day 59).

Immunized mice were re-challenged with *P. berghei* on day 59 and infection was followed for 7 or 14 days post-re-challenge. 5 mice/group were euthanized at day 4 or 7 and the remaining mice were monitored for parasitemia.

Readouts:
Parasitemia; days 5, 8, 11 and 14 post-challenge (days 64, 67, 70, 73).
T cell phenotypes (day 66).

Serum Anti-PbMIF IgG Titers on Day 14 (2 Weeks after First Immunization) and Day 35 (2 Weeks after Second Immunization)

Serum IgG titers were measured by anti-PbMIF ELISA on day 14, following the first immunization and day 35, following the second immunization. Anti-PbMIF ELISA assays were performed as in Example 1.

Figure 3:
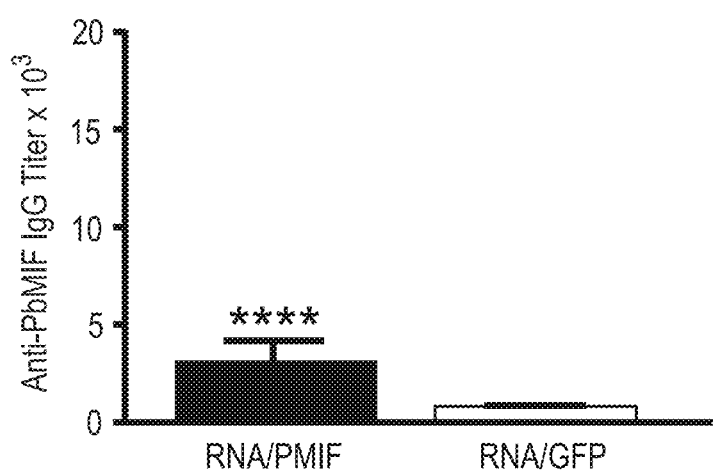
FIG. 3 shows mean serum anti-PbMIF titers ($OD_{450\ nm}$) at day 14 (2 weeks after first immunization) for mice immunized with RNA/PMIF CNE or RNA/GFP CNE. Mean titers are expressed as endpoint titers; the reciprocal dilution that yields background $OD_{450\ nm}$. ****P<0.0001 Mann-Whitney U, n=15 per group.
Figure 4:
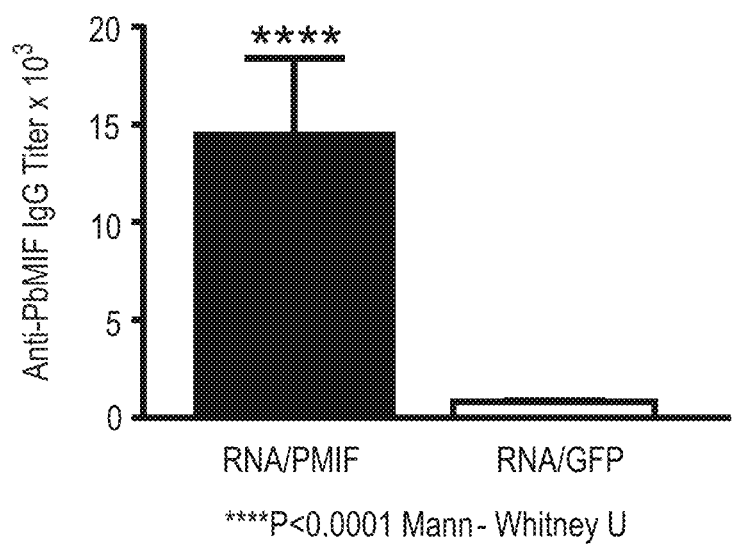
FIG. 4 shows mean serum anti-PbMIF titers ($OD_{450\ nm}$) at day 35 (2 weeks after second immunization) for mice immunized with RNA/PMIF CNE or RNA/GFP CNE. Mean titers are expressed as in FIG. 3. ****P<0.0001 Mann-Whitney U, n=15 per group.

Serum anti-PbMIF IgG titers were measured for each mouse at day 14. An anti-PbMIF IgG response (~1/2500) was observed in 50% of PbMIF-immunized mice in Group 1 after the first immunization. Mean titers at day 14 are shown in FIG. 3.

Also, serum anti-PbMIF IgG titers were measured for each mouse at day 35. An increase of the anti-PbMIF IgG titers was observed in 95% of PbMIF-immunized mice in Group 1 after the second immunization in the PbMIF-CNE group and the titers are 5-fold higher compared to those at day 14 (~1/14,500).

Challenge Infection on Days 35-42 to Expand *Plasmodium*-Specific Memory T Cells Parasitemia was assessed on days 3, 5, and 7 following first challenge (days 35-42) as described in Example 1. Serum IFN-γ was also assessed by specific ELISA on day 5 post-infection.

Figure 5A:
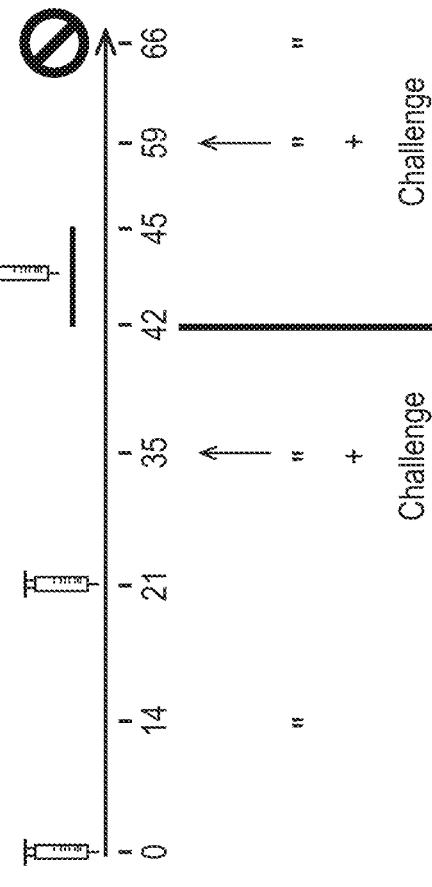
FIGS. 5A-C show.
Figure 5C:
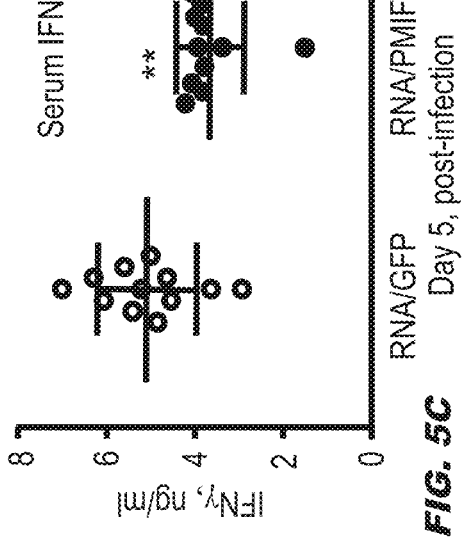
Figure 5B:
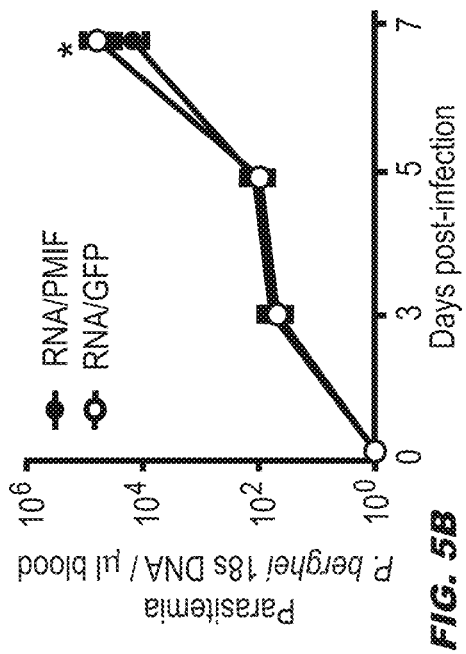

As shown in FIG. 5B, a detectable (0.5 log) difference in parasitemia was observed at 7 days following first *Plasmodium* infection. This effect is associated with reduced circulating IFN-γ that is consistent with reduced levels of a highly inflammatory, IFN-γ+ T cell response (FIG. 5C).

Figure 6A:
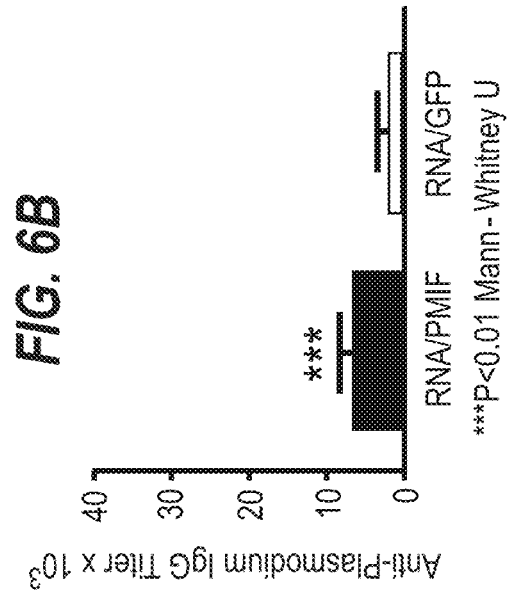
FIG. 6A shows mean serum anti-PbMIF titers ($OD_{450\ nm}$) at day 59 (2.5 weeks after first infection) for mice immunized with RNA/PMIF CNE or RNA/GFP CNE (**P<0.0001 Mann-Whitney U, n=15 per group).
Figure 6B:
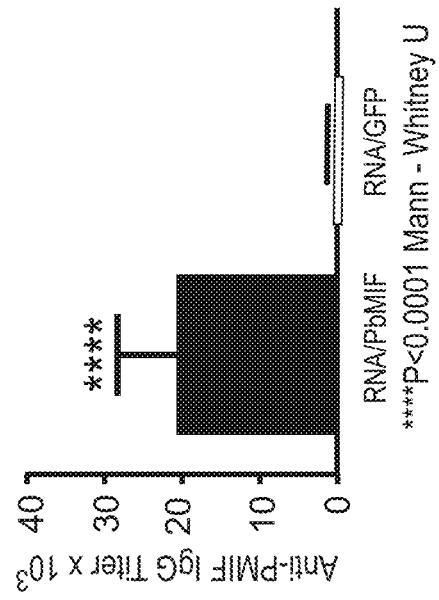
FIG. 6B shows mean anti-Plasmodium IgG responses at day 59 (*P<0.01 Mann-Whitney U, n=15 per group). Mean titers are expressed as in FIG. 3.

Serum Anti-PbMIF and Anti-*Plasmodium* IgG Titers on Day 59, 2.5 Weeks after the First Infection Serum anti-PbMIF IgG titers were measured for each mouse at day 59. *Plasmodium* infection increased the titers of anti-PbMIF Ig by 10-fold (FIG. 6A) in RNA/PbMIF versus RNA/GFP mice. Also, serum anti-*Plasmodium* IgG titers were measured at day 59 by anti-mouse IgG ELISA on parasitized red cell lysates. *Plasmodium* infection increased anti-*Plasmodium* Ig titers by 5-fold (FIG. 6B) in RNA/PbMIF versus RNA/GFP mice.

Parasitemia Following Re-Challenge with *Plasmodium* on Day 59

Parasitemia was assessed on days 5, 8, 11 and 14 following second challenge (days 59-73) as described in Example 1.

Figure 7:
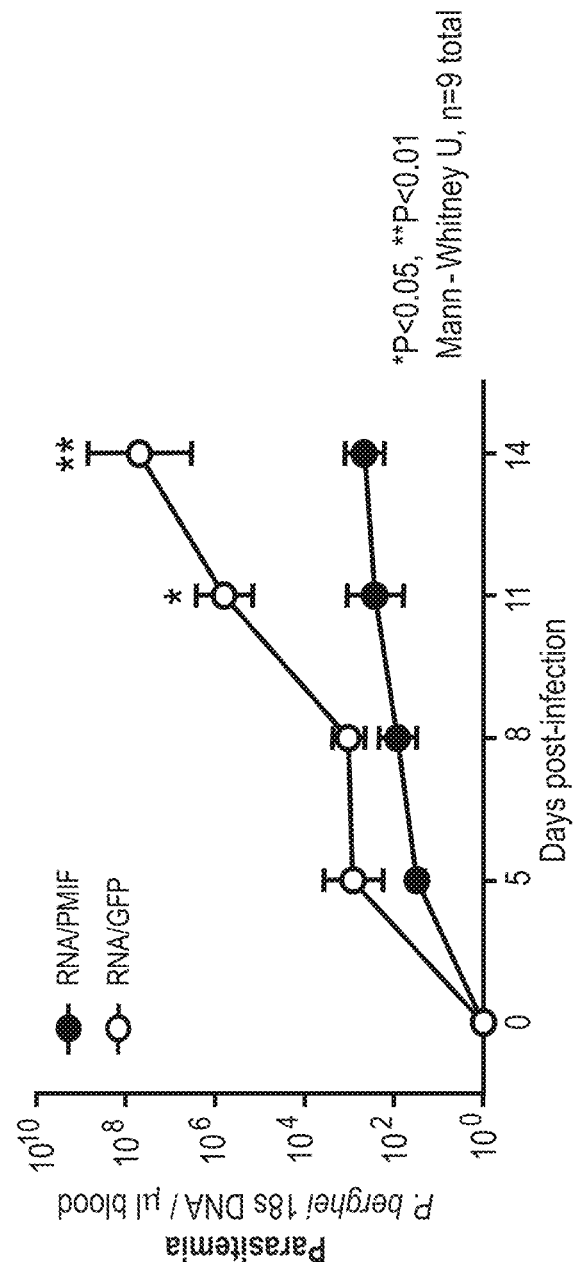
FIG. 7 shows Plasmodium parasitemia in mice immunized with RNA/PMIF CNE or RNA/GFP CNE over 14 days following second challenge (days 59-73). *P<0.05, **P<0.01 Mann-Whitney U, n=9 total (4×RNA/GFP CNE control, 5×RNA/PMIF CNE).

As shown in FIG. 7, RNA/PbMIF immunization markedly reduced parasitemia (5 log at day 14 post-infection) after *Plasmodium* re-challenge on day 59.

Assessment of RNA/PbMIF Effects on *Plasmodium*-Specific T Cell Phenotype

Mice were euthanized at day 7 after second infection and the T cell response and phenotype analysed along with the cytokine production. Splenic cells were isolated from 4-5 mice per experimental group and analysed for CD62L and IL-7Rα staining. CD62L and IL-7Rα identify different T cell subsets responding to *P. berghei* ($CD4^+Ki67^{hi}$). The results are summarized in Table 3.

TABLE 3

| Antigen | Tmem: CD4+ *P. berghei*-responding T memory cells phenotyped as CD62L+IL-7Rα+ |
|---|---|
| PbMIF-CNE (Group 1) | 29.5% |
| GFP-CNE (Group 2 - control) | 17.9% |

Thus, PbMIF neutralization increases the pool of *P. berghei*-responding CD4+ memory T cells.

Impact of RNA/PbMIF Vaccine on *Plasmodium*-Specific T Cells

Figure 8A:
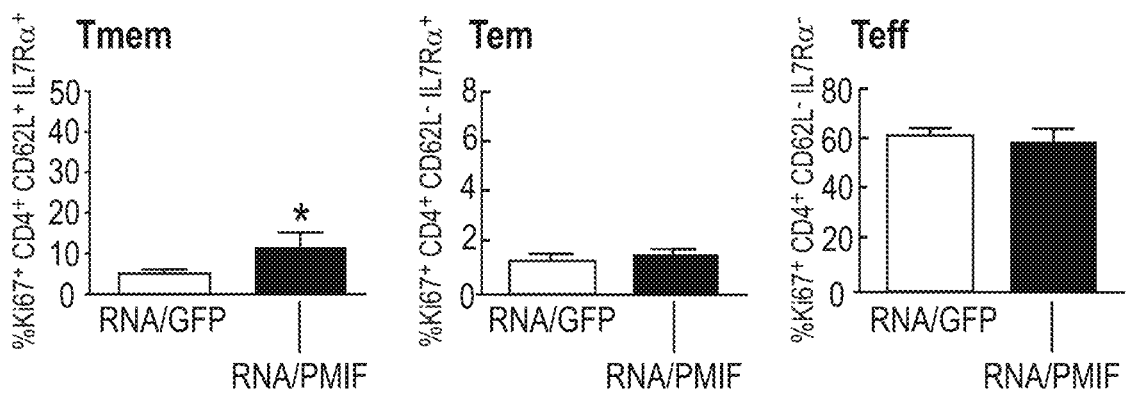
FIGS. 8A-C show the effects of RNA/PMIF CNE versus or RNA/GFP CNE immunization on T cell phenotype. T cells responding to P. berghei (CD4+Ki67$^{hi}$) were divided into subsets: Tmem (memory) CD62L+ IL-7Rα+; Tem (effector memory) CD62L− IL-7Rα+; and Teff (effector) CD62L− IL-7Rα−.
Figure 8B:
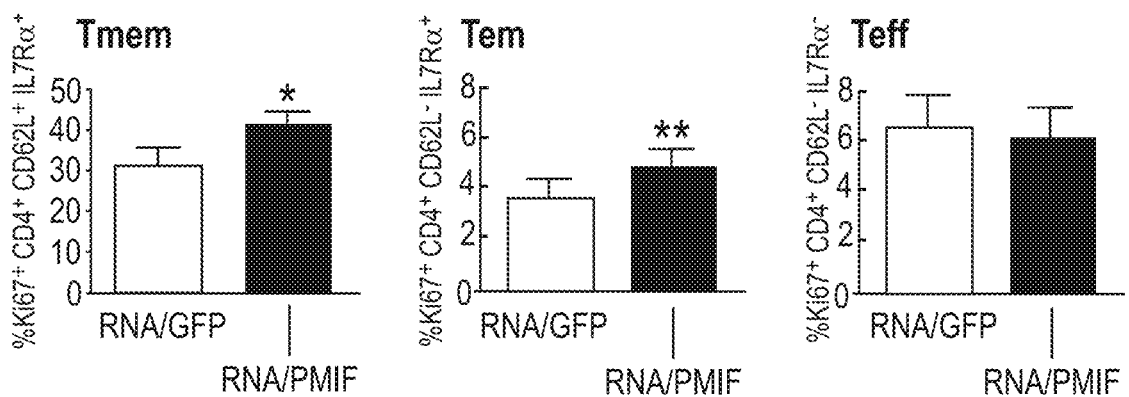

T cell phenotypes observed after first *Plasmodium* infection (day 7 post-infection, data from study in Example 1) (FIG. 8A) were compared with T cell phenotypes observed after second *Plasmodium* infection (day 7) (FIG. 8B).

As can be seen in FIGS. 8A and 8B, the RNA/PbMIF-CNE vaccine promotes the development of *Plasmodium*-specific Tmem cells ($CD62L^+$ $IL-7R\alpha^+$) during a first infection by *P. berghei* and these Tmem cells increase further during second infection.

Figure 8C:
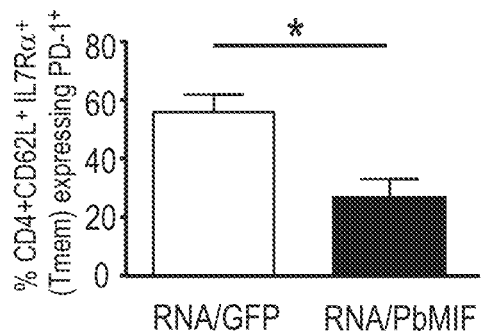

Furthermore, T cell exhaustion, as indicated by PD-1-expressing *Plasmodium*-specific Tmem cells, was reduced in RNA/PbMIF-immunized mice versus RNA/GFP immunized mice (FIG. 8C).

T Cell Cytokine Production by *Plasmodium*-Responsive T Cell Subsets

IFN-γ production by Tem (short-lived effector memory cells) is reduced in PbMIF immunized animals. This may reflect a less inflammatory (and more effective) *Plasmodium*-specific T cell response. No evident changes in TNF producing T cells were noted. (Data not shown)

Conclusions (2)

Self-replicating RNA vaccines are well-tolerated and produce strong humoral responses to *Plasmodium* MIF (PbMIF). First and second immunizations induced a response in 50% and 95% of immunized mice, respectively, with a much higher titer after the second immunization, and again after PbA infection.

RNA/PbMIF (CNE) immunization neutralized *Plasmodium* PbMIF activity, as evidenced by enhancement in CD4 T cell memory differentiation. The effects of this neutralization are:

Higher Tmem cell numbers, and a stronger humoral anti-*Plasmodium* antibody response. After primary challenge with *P. berghei*, there is a measurable and significant decrease in parasitemia (0.5 log).

Re-challenge after cure of primary infection results in a further expansion of Tmem numbers and a significant reduction in parasitemia (5 log).

Immunization with RNA/PbMIF allows for the development of memory T cells and provides significant protection to malaria re-challenge. RNA/PbMIF may be a viable vaccine candidate, either as a stand-alone or in combination with other *Plasmodium* vaccine candidates, where it would act to promote long-lasting memory T cell responses.

Example 3: Passive Transfer of a Polyclonal Anti-PbMIF Antibody

IgG was purified from a rabbit immunized with recombinant PbMIF (Anti-PbMIF IgG) or from a non-immunized rabbit (Ctrl IgG) and 200 μg injected i.p. into C57BL/6 mice at −6 hrs, 24 hrs, 48 hrs, and 72 hrs after infection with 1×10$^6$ *P. berghei* parasitized red cells. Parasitemia was enumerated by quantitative PCR of blood at day 7 post-infection.

Figure 9:
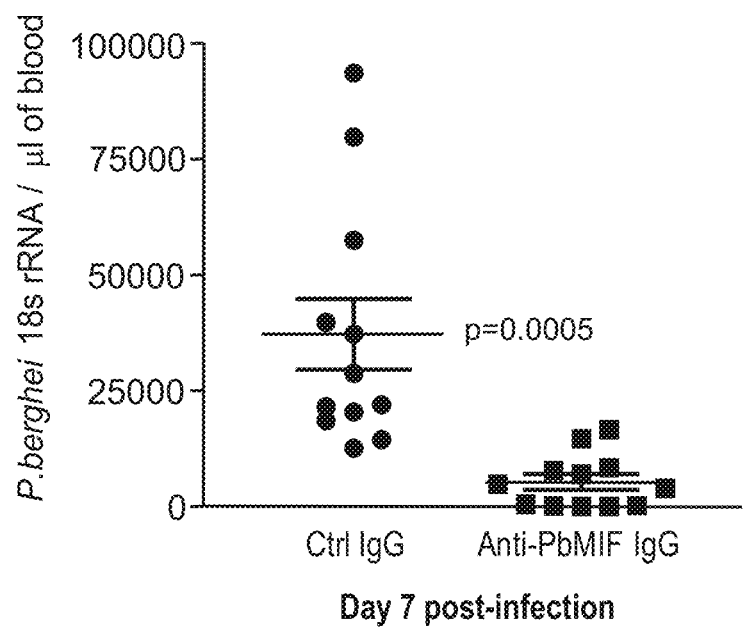
FIG. 9 shows Plasmodium parasitemia in mice receiving passive transfer of a polyclonal anti-PbMIF antibody (IgG) compared to mice receiving control IgG from a non-immunized rabbit (Ctrl IgG) at day 7 post-infection. Each data point is a single mouse. P=0.0005 by t-test.

As shown in FIG. 9, passive transfer of the anti-PbMIF antibody significantly reduces parasitemia in the *P. berghei* infection mouse model of malaria.

Figure 10E:
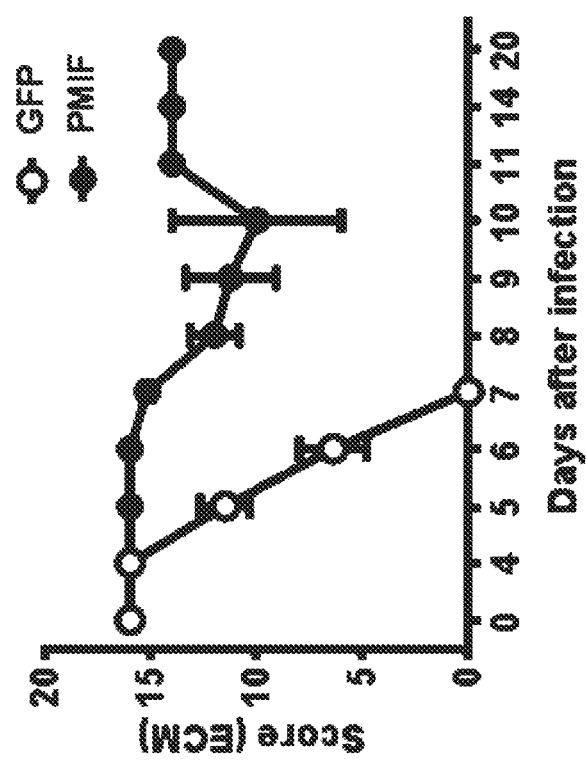

In a further study, 200 μg of IgG purified from serum by protein-G chromatography (Pierce) from GFP (control) or PbMIF immunized and PbA-infected mice was administered i.p. to naïve BALB/c or C57BL/6 (cerebral malaria-sensitive) mice and followed by PbA infection (FIG. 10A). I.p. administration was on days −1, 1, 2, and 3 post-infection. In C57BL/6 mice, cerebral malaria was monitored and symptoms classified by the Rapid Murine Coma and Behavior Scale (50), where 16=no signs, 15-11=mild symptomatic, 10-08=prodromal signs of Experimental Cerebral Malaria (ECM), 07-04=ECM. Agonal mice were immediately sacrificed.

Figure 10D:
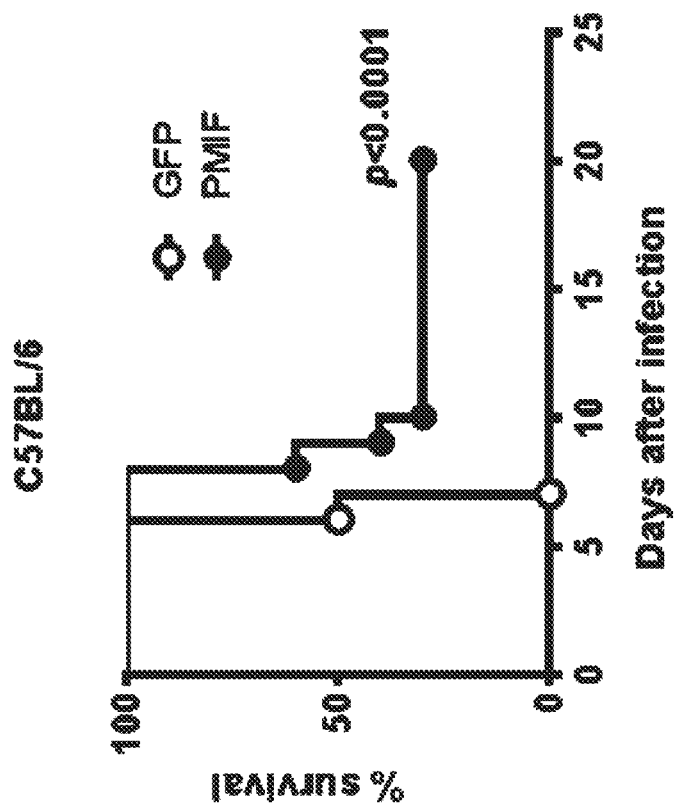

Administration of IgG from PbMIF immunized mice into naïve BALB/c mice that were infected with PbA provided partial protection, with a delayed rise in parasitemia, a 30% reduction in peak parasitemia, and a 30% prolongation in survival time (FIGS. 10B and C). When studied in the acutely lethal C57BL/6 model of cerebral malaria, IgG from the GFP (control) immunized mice showed no protection: all mice developed neurological signs and became moribund between days 6-7 post-infection (FIGS. 10D and E). By contrast, in C57BL/6 mice that received IgG from PbMIF immunized mice and then were infected with PbA, there was a marked delay in the time to develop neurologic disease, less severe disease, and a survival rate of 30%, with complete protection from neurologic manifestations. Cerebral malaria is a uniformly fatal complication of PbA infection in C57BL/6 mice and the protective effect of immunoglobulin occurred despite equivalent parasitemia between groups until the time of lethality (day 6), after which surviving mice eliminated their parasites (data not shown).

Example 4: Protective Effect of CD4 T Cells from Vaccinated Mice

Figure 11A:
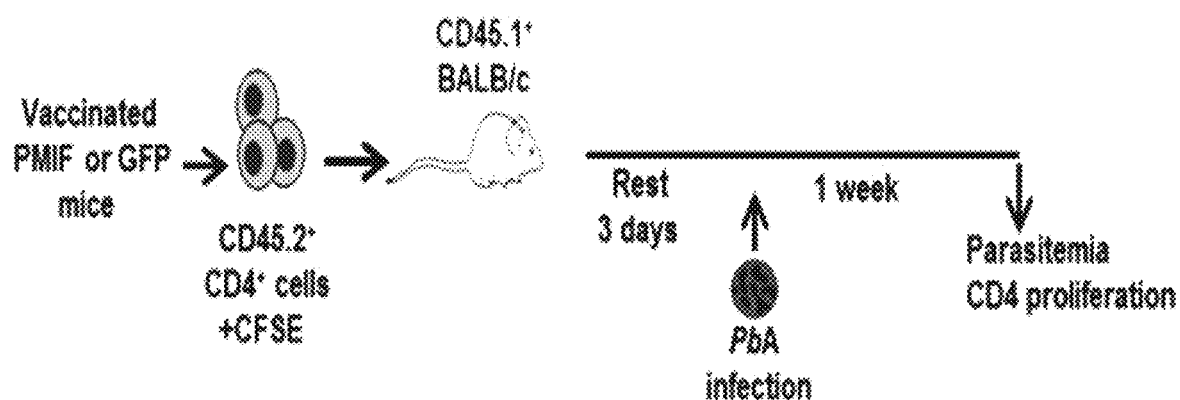

BALB/c mice (CD45.2$^+$) immunized with the RNA/PbMIF-CNE or RNA/GFP-CNE vaccine were infected by i.p. injection of 10$^6$ PbA-infected RBCs on day 0 and treated with chloroquine on days 7 to 10. At 4 weeks previously infected mice were reinfected and on day 7 post-infection, the splenocytes were isolated and the CD4 T cells were incubated with 10 mM chloroquine for 2 h at 37° C. and CFSE labeled. 5×10$^6$ CD4 T cells (CD45.2) then were transferred i.v into naïve CD45.1 BALB/c mice. All CD45.1 mice were infected with PbA (1×10$^6$ iRBCs) at day 3 post-transfer (FIG. 11A). The course of the infection in mice transferred with CD4 T cells from RNA/GFP-CNE or RNA/PMIF-CNE donors was monitored by determining parasitemia by FACS. At day 7 post-infection, mice were sacrificed and CD4$^+$ CD45.2$^+$ donor cells recovered, quantified, and proliferation assessed by CFSE dilution.

Figure 11B:
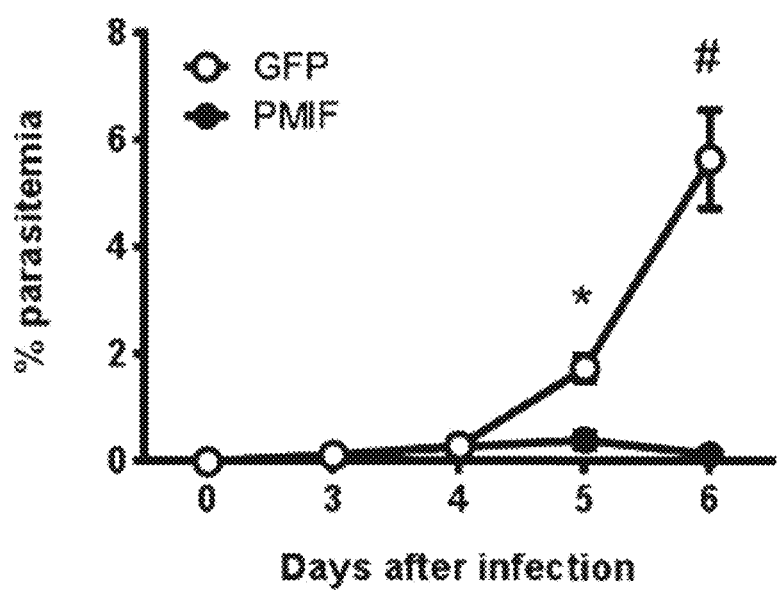

Infection was established in recipient mice that received CD4 T cells from the GFP (control) group, as evidenced by increasing parasitemia, but not in mice that received CD4 T cells from the PbMIF immunized donors (FIG. 11B).

Parasitemia was significantly reduced in the mice transferred with CD4 T cells from RNA/PMIF-CNE-immunized donors compared to control mice transferred with CD4 T cells from GFP-CNE-immunized donors. Thus, adoptive transfer of CD4 T cells from PMIF-vaccinated mice also conferred protection to parasite re-challenge. In fact, CD4 T cells from PbMIF immunized mice confer complete protection against blood-stage *P. berghei* infection.

The protection conferred by the adoptive transfer of CD4 T cells from the PbMIF immunized donors was associated with a higher number of proliferating CD4 T cells (CFSE$^{lo}$) (FIGS. 11C-E), higher levels of IFN-γ production (FIG. 11F), and reduced expression of the exhaustion marker PD-1 (FIG. 11G) when compared to CD4 T cells adoptively transferred from the control group.

These data indicate that the augmented CD4 T cell response that develops after PbMIF immunization in infected mice offers complete protection against infection and is sufficient to prevent the establishment of blood-stage infection.

It will be understood that the invention has been described by way of example only and modifications may be made whilst remaining within the scope and spirit of the invention.

REFERENCES

[1] Doolan et al., *Clin Microbiol Rev,* 2009; 22(1): 13-36
[2] Yazdanbakhsh & Sacks 2010 *Nat Rev Immunol,* 10(2): 80-81
[3] Vermeire et al. 2008 *Trends Parasitol.;* 24(8):355-63
[4] Dobson et al. 2009 *Protein Sci.* 18(12):2578-91
[5] Sun et al. 2012 *PNAS* 31; 109(31):E2117-26
[6] Leng et al. 2003 *J Exp Med* 197:1467-1476
[7] Kamir et al. 2008 *J Immunol.;* 180(12):8250-61
[8] Cho et al. (2011) *Chem Biol.;* 18(9): 1089-1101.
[9] Sambrook et al. (1989) *Molecular Cloning: A Laboratory Manual.*
[10] *Short protocols in molecular biology* (4th ed, 1999) Ausubel et al. eds. ISBN 0-471-32938-X.
[11] U.S. Pat. No. 5,707,829
[12] *Current Protocols in Molecular Biology* (F. M. Ausubel et al. eds., 1987) Supplement 30.
[13] Geysen et al. (1984) *PNAS USA* 81:3998-4002.
[14] Carter (1994) *Methods Mol Biol* 36:207-23.
[15] Jameson, B A et al. 1988, *CABIOS* 4(1):181-186.
[16] Raddrizzani & Hammer (2000) *Brief Bioinform* 1(2): 179-89.
[17] De Lalla et al. (1999) *J. Immunol.* 163:1725-29.
[18] Brusic et al. (1998) *Bioinformatics* 14(2):121-30
[19] Meister et al. (1995) *Vaccine* 13(6):581-91.
[20] Roberts et al. (1996) *AIDS Res Hum Retroviruses* 12(7):593-610.

[21] Maksyutov & Zagrebelnaya (1993) *Comput Appl Biosci* 9(3):291-7.
[22] Feller & de la Cruz (1991) *Nature* 349(6311):720-1.
[23] Hopp (1993) *Peptide Research* 6:183-190.
[24] Welling et al. (1985) *FEBS Lett.* 188:215-218.
[25] Davenport et al. (1995) *Immunogenetics* 42:392-297.
[26] U.S. Pat. No. 5,928,902.
[27] WO 90/01496.
[28] Bodanszky (1993) *Principles of Peptide Synthesis* (ISBN: 0387564314).
[29] Fields et al. (1997) *Meth Enzymol* 289: *Solid-Phase Peptide Synthesis*. ISBN: 0121821900.
[30] Chan & White (2000) *Fmoc Solid Phase Peptide Synthesis*. ISBN: 0199637245.
[31] Kullmann (1987) *Enzymatic Peptide Synthesis*. ISBN: 0849368413.
[32] Ibba (1996) *Biotechnol Genet Eng Rev* 13:197-216.
[33] WO2005/113782.
[34] WO2012/006376
[35] WO2012/006380
[36] Geall et al. (2012) *PNAS USA*. September 4; 109(36): 14604-9
[37] WO2013/006834.
[38] WO2013/006837.
[39] WO2012/030901.
[40] WO2012/031046.
[41] WO2012/031043.
[42] WO2013/033563.
[43] WO2013/006825.
[44] Breedveld (2000) *Lancet* 355(9205):735-740.
[45] Gorman & Clark (1990) *Semin. Immunol.* 2:457-466.
[46] WO97/18229
[47] Tang et al. (2012) *J Helminthol.;* 86(4):430-9.
[48] Gennaro (2000) *Remington: The Science and Practice of Pharmacy*. 20th edition, ISBN: 0683306472.
[49] WO2011/027222.
[50] Carroll et al., (2010) *PLoS ONE* 5, e13124.

The invention includes at least the following numbered embodiments:

1. A method for providing protective immunity against a parasite infection in a subject in need thereof, comprising administering an immunologically effective amount of a composition to the subject, wherein the composition comprises:
   (i) a nucleic acid comprising a sequence which encodes a parasite macrophage migration inhibitory factor (MIF) antigen;
   (ii) a parasite MIF antigen; or
   (iii) an antibody which specifically binds to a parasite MIF antigen.
2. The method of embodiment 1 wherein the composition comprises an RNA-based vaccine.
3. The method of embodiment 1 or 2 wherein the protective immunity is characterized by protective immunological memory against the parasite and/or an effective parasite-responsive memory T cell population.
4. The method of any preceding embodiment wherein the parasite MIF antigen comprises a full-length MIF polypeptide or an immunogenic fragment thereof.
5. The method of any one of embodiments 1 and 3 wherein the composition comprises a nucleic acid-based vaccine comprising the nucleic acid sequence which encodes a parasite MIF antigen.
6. The method of embodiment 5 wherein the nucleic acid-based vaccine is an RNA-based vaccine.
7. The method of embodiment 6 wherein the nucleic acid-based vaccine comprises a self-replicating RNA molecule.
8. The method of embodiment 7 wherein the self-replicating RNA is an alphavirus-derived RNA replicon.
9. The method of any preceding embodiment wherein the composition comprises a cationic nano-emulsion (CNE) delivery system.
10. The method of any one of embodiments 1 to 8 wherein the composition comprises a lipid nanoparticle (LNP) delivery system.
11. The method of any preceding embodiment wherein the composition comprises one or more adjuvants.
12. The method of embodiment 1, 3 or 4 wherein the antibody which specifically binds to a parasite MIF antigen comprises polyclonal antibody.
13. The method of embodiment 1, 3 or 4 wherein the antibody which specifically binds to a parasite MIF antigen is a humanized or chimeric antibody.
14. The method of any preceding embodiment wherein the parasite is a parasitic protozoan.
15. The method of embodiment 14 wherein the protozoan is an apicomplexan parasite.
16. The method of embodiment 15 wherein the protozoan belongs to the genus *Plasmodium*.
17. The method of embodiment 14 wherein the protozoan belongs to a genus selected from the group consisting of: *Plasmodium, Toxoplasma, Babesia, Eimeria, Theileria, Neospora, Sarcocystis, Leishmania*, and *Trypanosoma*.
18. The method of any one of embodiments 1 to 13 wherein the parasite is a parasitic helminth.
19. The method of embodiment 18 wherein the parasitic helminth is a nematode.
20. The method of embodiment 18 or embodiment 19 wherein the parasitic helminth belongs to a genus selected from the group consisting of: *Ancyclostoma, Necator, Brugia, Wuchereria, Loa, Mansonella, Trichinella, Trichuris, Ascaris, Anisakis, Dracunculus, Strongyloides, Haemonchus, Schistosoma* and *Fasciola*.
21. The method of any preceding embodiment wherein two or more doses of the composition are administered to the subject.
22. The method of embodiment 21 wherein the two or more doses are administered at least 1 week apart, about 2 weeks, about 3 weeks, about 4 weeks, about 6 weeks, about 8 weeks, about 10 weeks, about 12 weeks, or about 16 weeks apart.
23. The method of any preceding embodiment wherein the subject is a vertebrate.
24. The method of embodiment 23 wherein the subject is a mammal.
25. The method of embodiment 24 wherein the subject is a human.
26. The method of embodiment 24 wherein the subject is a veterinary mammal.
27. The method of embodiment 26 wherein the veterinary mammal is a cat, dog, horse, cow, sheep, deer, goat, or pig.
28. The method of any preceding embodiment wherein the composition further comprises a nucleic acid sequence which encodes an additional parasite antigen.
29. The method of any preceding embodiment wherein the composition further comprises an additional parasite antigen.
30. The method of any preceding embodiment wherein the composition is administered to the subject in combination with a further composition which comprises a nucleic acid comprising a sequence which encodes an additional parasite antigen.

31. The method of any preceding embodiment wherein the composition is administered to the subject in combination with a further composition which comprises an additional parasite antigen.
32. A composition for use in a method of providing protective immunity against a parasite infection in a subject in need thereof, which comprises an immunologically effective amount of:
   (i) a nucleic acid comprising a sequence which encodes a parasite MIF antigen;
   (ii) a parasite MIF antigen; or
   (iii) an antibody which specifically binds to a parasite MIF antigen.
33. The composition of embodiment 32 for use in a method according to any one of embodiments 1 to 31.
34. A composition comprising an immunologically effective amount of:
   (i) a nucleic acid comprising a sequence which encodes a parasite MIF antigen; or
   (ii) a parasite MIF antigen;
   wherein the MIF antigen is from a parasitic protozoan.
35. The composition of embodiment 34 wherein the protozoan is an apicomplexan parasite, such as *Plasmodium*.
36. The composition of embodiment 34 or 35 wherein the protozoan belongs to a genus selected from the group consisting of: *Plasmodium, Toxoplasma, Babesia, Eimeria, Theileria, Neospora, Sarcocystis, Leishmania*, and *Trypanosoma*.
37. A composition comprising an immunologically effective amount of:
   (i) a nucleic acid comprising a sequence which encodes a parasite MIF antigen; or
   (ii) a parasite MIF antigen;
   wherein the MIF antigen is from a parasitic helminth which belongs to a genus selected from the group consisting of: *Ancyclostoma, Necator, Brugia, Wuchereria, Loa, Mansonella, Trichinella, Trichuris, Ascaris, Anisakis, Dracunculus, Strongyloides, Haemonchus, Schistosoma* and *Fasciola*.
38. The composition of any one of embodiments 34 to 37 wherein the parasite MIF antigen comprises a full-length MIF polypeptide or an immunogenic fragment thereof.
39. The composition of any one of embodiments 34 to 38 which comprises a nucleic acid-based vaccine comprising the nucleic acid sequence which encodes a parasite MIF antigen.
40. The composition of embodiment 39 wherein the nucleic acid-based vaccine is an RNA-based vaccine.
41. The composition of embodiment 40 wherein the nucleic acid-based vaccine comprises a self-replicating RNA molecule.
42. The composition of embodiment 41 wherein the self-replicating RNA is an alphavirus-derived RNA replicon.
43. The composition of any one of embodiments 34 to 42 which comprises a cationic nano-emulsion (CNE) delivery system.
44. The composition of any one of embodiments 34 to 42 which comprises a lipid nanoparticle (LNP) delivery system.
45. The composition of any one of embodiments 34 to 44 which comprises one or more adjuvants.
46. The composition of any one or embodiments 34 to 45 wherein the composition further comprises a nucleic acid sequence which encodes an additional parasite antigen.
47. The composition of any one or embodiments 34 to 46 wherein the composition further comprises an additional parasite antigen.
48. A method of enhancing an immune response to a non-MIF parasite antigen in a subject, comprising administering an immunologically effective amount of a composition to the subject, wherein the composition comprises:
   (i) a nucleic acid comprising a sequence which encodes a parasite MIF antigen;
   (ii) a parasite MIF antigen; or
   (iii) an antibody which specifically binds to a parasite MIF antigen.
49. The method of embodiment 48 which further comprises administering the non-MIF parasite antigen to the subject.
50. The method of embodiment 48 which is a method according to any one of embodiments 1-31.
51. A method for providing protective immunity against a parasite infection in a subject in need thereof, comprising administering parasite-responsive CD4 T cells isolated from a compatible host, wherein the host has been immunized with a composition comprising:
   (i) a nucleic acid comprising a sequence which encodes a parasite MIF antigen; or
   (ii) a parasite MIF antigen.
52. The method of embodiment 51 wherein the compatible host has been administered a composition according to a method of any one of embodiments 1-31.

The invention claimed is:

1. A method for providing protective immunity against a *Plasmodium* infection in a subject in need thereof, comprising administering an immunologically effective amount of a composition to the subject, wherein the composition is an RNA immunogen comprising an RNA comprising a sequence which encodes a *Plasmodium* macrophage migration inhibitory factor (MIF) antigen, wherein the RNA immunogen induces protective immunity in the subject that is characterized by protective immunological memory against the *Plasmodium* and/or an effective *Plasmodium* parasite-responsive memory T cell population.

2. The method of claim 1, wherein the RNA-based immunogen comprises a self-replicating RNA molecule.

3. The method of claim 2, wherein the self-replicating RNA is an alphavirus-derived RNA replicon.

4. The method of claim 1, wherein the composition further comprises a delivery system selected from the group consisting of a cationic nano-emulsion (CNE) delivery system and a lipid nanoparticle (LNP) delivery system.

5. The method of claim 1 wherein the subject is a vertebrate.

6. The method of claim 1 wherein:
(a) the composition further comprises a nucleic acid sequence which encodes an additional *Plasmodium* antigen, and/or
(b) the composition further comprises an additional *Plasmodium* antigen, and/or
(c) the composition is administered to the subject in combination with a further composition which comprises a nucleic acid comprising a sequence which encodes an additional *Plasmodium* antigen; and/or
(d) the composition is administered to the subject in combination with a further composition which comprises an additional *Plasmodium* antigen.

7. A method of enhancing an immune response to a non-MIF *Plasmodium* antigen in a subject, comprising administering a composition to the subject, wherein the composition is an RNA immunogen comprising an RNA comprising a sequence which encodes a *Plasmodium* macrophage migration inhibitory factor (MIF) antigen, wherein the RNA immunogen induces protective immunity that is characterized by protective immunological memory against the *Plasmodium* and/or an effective *Plasmodium* parasite-responsive memory T cell population, and wherein the composition further comprises an effective amount of the non-MIF *Plasmodium* antigen.

8. The method of claim 1, wherein the composition is administered to the subject as a prophylactic.

* * * * *

SEQUENCE LISTING

```
<160> NUMBER OF SEQ ID NOS: 19

<210> SEQ ID NO 1
<211> LENGTH: 115
<212> TYPE: PRT
<213> ORGANISM: Plasmodium falciparum

<400> SEQUENCE: 1

Pro Cys Cys Glu Val Ile Thr Asn Val Asn Leu Pro Asp Asp Asn Val
1               5                   10                  15

Gln Ser Thr Leu Ser Gln Ile Glu Asn Ala Ile Ser Asp Val Met Gly
            20                  25                  30

Lys Pro Leu Gly Tyr Ile Met Ser Asn Tyr Asp Tyr Gln Lys Asn Leu
        35                  40                  45

Arg Phe Gly Gly Ser Asn Glu Ala Tyr Cys Phe Val Arg Ile Thr Ser
    50                  55                  60
```

Ile Gly Gly Ile Asn Arg Ser Asn Asn Ser Ala Leu Ala Asp Gln Ile
65                  70                  75                  80

Thr Lys Leu Leu Val Ser Asn Leu Asn Val Lys Ser Arg Arg Ile Tyr
                85                  90                  95

Val Glu Phe Arg Asp Cys Ser Ala Gln Asn Phe Ala Phe Ser Gly Ser
            100                 105                 110

Leu Phe Gly
        115

<210> SEQ ID NO 2
<211> LENGTH: 115
<212> TYPE: PRT
<213> ORGANISM: Plasmodium berghei

<400> SEQUENCE: 2

Pro Cys Cys Glu Leu Ile Thr Asn Ile Ser Ile Pro Asp Asp Lys Ala
1               5                   10                  15

Gln Asn Thr Leu Ser Glu Ile Glu Asp Ala Ile Ser Asn Ile Leu Gly
                20                  25                  30

Lys Pro Val Ala Tyr Ile Met Ser Asn Tyr Asp Tyr Gln Lys Asn Leu
            35                  40                  45

Arg Phe Ser Gly Ser Asn Glu Gly Tyr Cys Phe Val Arg Leu Thr Ser
        50                  55                  60

Ile Gly Gly Ile Asn Arg Ser Asn Asn Ser Leu Leu Ala Asp Lys Ile
65                  70                  75                  80

Thr Lys Ile Leu Ser Asn His Leu Ser Val Lys Pro Arg Arg Val Tyr
                85                  90                  95

Ile Glu Phe Arg Asp Cys Ser Ala Gln Asn Phe Ala Phe Ser Gly Ser
            100                 105                 110

Leu Phe Gly
        115

<210> SEQ ID NO 3
<211> LENGTH: 115
<212> TYPE: PRT
<213> ORGANISM: Plasmodium yoelii

<400> SEQUENCE: 3

Pro Cys Cys Glu Leu Ile Thr Asn Ile Ser Ile Pro Asp Asp Lys Ala
1               5                   10                  15

Gln Asn Ala Leu Ser Glu Ile Glu Asp Ala Ile Ser Asn Val Leu Gly
                20                  25                  30

Lys Pro Val Ala Tyr Ile Met Ser Asn Tyr Asp Tyr Gln Lys Asn Leu
            35                  40                  45

Arg Phe Ser Gly Ser Asn Glu Gly Tyr Cys Phe Val Arg Leu Thr Ser
        50                  55                  60

Ile Gly Gly Ile Asn Arg Ser Asn Asn Ser Ser Leu Ala Asp Lys Ile
65                  70                  75                  80

Thr Lys Ile Leu Ser Asn His Leu Gly Val Lys Pro Arg Arg Val Tyr
                85                  90                  95

Ile Glu Phe Arg Asp Cys Ser Ala Gln Asn Phe Ala Phe Ser Gly Ser
            100                 105                 110

Leu Phe Gly
        115

<210> SEQ ID NO 4

```
<211> LENGTH: 115
<212> TYPE: PRT
<213> ORGANISM: Plasmodium chabaudi

<400> SEQUENCE: 4

Pro Cys Cys Glu Leu Ile Thr Asn Ile Ser Ile Pro Asp Asp Lys Ala
1               5                   10                  15

Gln Ala Ala Leu Ser Glu Ile Glu Asp Ala Ile Ser Asn Val Leu Gly
            20                  25                  30

Lys Pro Thr Ala Tyr Ile Met Ser Asn Tyr Asp Tyr Gln Lys Asn Leu
        35                  40                  45

Arg Phe Ala Gly Ser Asn Glu Gly Tyr Cys Phe Val Arg Leu Thr Ser
    50                  55                  60

Leu Gly Gly Ile Asn Arg Ser Asn Asn Ser Ser Leu Ala Asp Lys Ile
65                  70                  75                  80

Thr Lys His Leu Ala Asn His Leu Gly Val Lys Pro Arg Arg Val Tyr
                85                  90                  95

Ile Glu Phe Arg Asp Cys Ser Ala Gln Asn Phe Ala Phe Ser Gly Ser
            100                 105                 110

Leu Phe Gly
        115

<210> SEQ ID NO 5
<211> LENGTH: 115
<212> TYPE: PRT
<213> ORGANISM: Plasmodium vivax

<400> SEQUENCE: 5

Pro Cys Cys Gln Val Ser Thr Asn Ile Asn Ala Ser Asp Asp Ala
1               5                   10                  15

Lys Lys Ala Leu Ser Gln Ile Glu Asn Ala Ile Ser Gln Val Leu Gly
            20                  25                  30

Lys Pro Leu Gly Tyr Ile Met Ser Asn Leu Asp Tyr Gln Lys His Met
        35                  40                  45

Arg Phe Gly Gly Ser His Asp Gly Phe Cys Phe Val Arg Val Thr Ser
    50                  55                  60

Leu Gly Gly Ile Asn Lys Ser Asn Asn Ser Ser Leu Ala Asp Lys Ile
65                  70                  75                  80

Thr Lys Ile Leu Ala Ser Thr Leu Asn Val Lys Ser Glu Arg Val Phe
                85                  90                  95

Ile Glu Phe Lys Asp Cys Ser Ala Gln Asn Phe Ala Phe Asn Gly Ser
            100                 105                 110

Leu Phe Gly
        115

<210> SEQ ID NO 6
<211> LENGTH: 115
<212> TYPE: PRT
<213> ORGANISM: Plasmodium knowlesi

<400> SEQUENCE: 6

Pro Cys Cys Gln Val Ser Thr Asn Ile Asn Val Ser Asp Asp Ala
1               5                   10                  15

Lys Lys Ala Leu Met Gln Ile Glu Asn Ala Ile Ser Gln Val Met Asn
            20                  25                  30

Lys Pro Met Gly Tyr Ile Met Ser Asn Leu Asp Tyr Gln Lys His Met
        35                  40                  45
```

```
Arg Phe Gly Gly Ser His Asp Gly Phe Cys Phe Val Arg Val Thr Ser
         50                  55                  60

Ile Ser Gly Ile Ser Arg Ser Asn Asn Thr Ala Leu Ala Asp Lys Ile
 65                  70                  75                  80

Thr Lys Ile Leu Ala Ser Thr Ile Lys Val Lys Ser Asp Arg Val Phe
                 85                  90                  95

Ile Glu Phe Lys Asp Cys Ser Ala Gln Asn Phe Ala Phe Asn Gly Ser
                100                 105                 110

Leu Phe Gly
        115

<210> SEQ ID NO 7
<211> LENGTH: 115
<212> TYPE: PRT
<213> ORGANISM: Toxoplasma gondii

<400> SEQUENCE: 7

Pro Lys Cys Met Ile Phe Cys Pro Val Ala Ala Thr Pro Ala Gln Gln
 1               5                  10                  15

Asp Ala Leu Leu Lys Asp Ala Glu Lys Ala Val Ala Asp Ala Leu Gly
                 20                  25                  30

Lys Pro Leu Ser Tyr Val Met Val Gly Tyr Ser Gln Thr Gly Gln Met
                 35                  40                  45

Arg Phe Gly Gly Ser Ser Asp Pro Cys Ala Phe Ile Arg Val Ala Ser
         50                  55                  60

Ile Gly Gly Ile Thr Ser Ser Thr Asn Cys Lys Ile Ala Ala Ala Leu
 65                  70                  75                  80

Ser Ala Ala Cys Glu Arg His Leu Gly Val Pro Lys Asn Arg Ile Tyr
                 85                  90                  95

Thr Thr Phe Thr Asn Lys Ser Pro Ser Glu Trp Ala Met Gly Asp Arg
                100                 105                 110

Thr Phe Gly
        115

<210> SEQ ID NO 8
<211> LENGTH: 112
<212> TYPE: PRT
<213> ORGANISM: Leishmania major

<400> SEQUENCE: 8

Pro Val Ile Gln Thr Phe Val Ser Thr Pro Leu Asp His His Lys Arg
 1               5                  10                  15

Glu Asn Leu Ala Gln Val Tyr Arg Ala Val Thr Arg Asp Val Leu Gly
                 20                  25                  30

Lys Pro Glu Asp Leu Val Met Met Thr Phe His Asp Ser Thr Pro Met
                 35                  40                  45

His Phe Phe Gly Ser Thr Asp Pro Val Ala Cys Val Arg Val Glu Ala
         50                  55                  60

Leu Gly Gly Tyr Gly Pro Ser Glu Pro Glu Lys Val Thr Ser Ile Val
 65                  70                  75                  80

Thr Ala Ala Ile Thr Lys Glu Cys Gly Ile Val Ala Asp Arg Ile Phe
                 85                  90                  95

Val Leu Tyr Phe Ser Pro Leu His Cys Gly Trp Asn Gly Thr Asn Phe
                100                 105                 110

<210> SEQ ID NO 9
<211> LENGTH: 112
```

```
<212> TYPE: PRT
<213> ORGANISM: Leishmania major

<400> SEQUENCE: 9

Pro Phe Leu Gln Thr Ile Val Ser Val Ser Leu Asp Asp Gln Lys Arg
1               5                   10                  15

Ala Asn Leu Ser Ala Ala Tyr Gly Met Ile Cys Arg Glu Glu Leu Gly
            20                  25                  30

Lys Pro Glu Asp Phe Val Met Thr Ala Phe Ser Asp Lys Thr Pro Ile
        35                  40                  45

Ser Phe Gln Gly Ser Thr Ala Pro Ala Ala Tyr Val Arg Val Glu Ser
    50                  55                  60

Trp Gly Glu Tyr Ala Pro Ser Lys Pro Lys Met Met Thr Pro Arg Ile
65                  70                  75                  80

Ala Ala Ala Ile Thr Lys Glu Cys Gly Ile Pro Ala Glu Arg Ile Tyr
                85                  90                  95

Val Phe Tyr Tyr Ser Thr Lys His Cys Gly Trp Asn Gly Thr Asn Phe
            100                 105                 110

<210> SEQ ID NO 10
<211> LENGTH: 113
<212> TYPE: PRT
<213> ORGANISM: Giardia intestinalis

<400> SEQUENCE: 10

Pro Cys Ala Ile Val Thr Thr Asn Ala Asp Phe Thr Lys Asp Gln Ala
1               5                   10                  15

Asp Ala Phe Cys Leu Asp Met Gly Gln Val Leu Ala Lys Glu Thr Gly
            20                  25                  30

Lys Pro Val Ser Tyr Cys Met Ala Gly Val Arg Lys Ala Asp Met Ser
        35                  40                  45

Phe Gly Thr Ser Thr Asp Leu Cys Cys Phe Val Asp Phe Tyr Cys Ile
    50                  55                  60

Gly Val Ile Ser Gln Ala Lys Asn Pro Ser Ile Ser Ala Ala Ile Thr
65                  70                  75                  80

Gly Cys Leu Thr Gln His Phe Lys Val Lys Pro Glu Arg Val Tyr Ile
                85                  90                  95

Ser Phe Asn Glu Ala Lys Gly His Asn Trp Gly Phe Asn Gly Ser Thr
            100                 105                 110

Phe

<210> SEQ ID NO 11
<211> LENGTH: 114
<212> TYPE: PRT
<213> ORGANISM: Brugia malayi

<400> SEQUENCE: 11

Pro Tyr Phe Thr Ile Asp Thr Asn Ile Pro Gln Asn Ser Ile Ser Ser
1               5                   10                  15

Ala Phe Leu Lys Lys Ala Ser Asn Val Val Ala Lys Ala Leu Gly Lys
            20                  25                  30

Pro Glu Ser Tyr Val Ser Ile His Val Asn Gly Gly Gln Ala Met Val
        35                  40                  45

Phe Gly Gly Ser Glu Asp Pro Cys Ala Val Cys Val Leu Lys Ser Ile
    50                  55                  60

Gly Cys Val Gly Pro Lys Val Asn Asn Ser His Ala Glu Lys Leu Tyr
65                  70                  75                  80
```

```
Lys Leu Leu Ala Asp Glu Leu Lys Ile Pro Lys Asn Arg Cys Tyr Ile
                85                  90                  95
Glu Phe Val Asp Ile Glu Ala Ser Ser Met Ala Phe Asn Gly Ser Thr
            100                 105                 110
Phe Gly

<210> SEQ ID NO 12
<211> LENGTH: 114
<212> TYPE: PRT
<213> ORGANISM: Wuchereria bancrofti

<400> SEQUENCE: 12

Pro Tyr Phe Thr Ile Asp Thr Asn Lys Pro Gln Asp Ser Ile Ser Ser
1               5                   10                  15
Ala Phe Leu Lys Lys Ala Pro Asn Val Val Pro Lys Ala Leu Gly Lys
            20                  25                  30
Pro Glu Ser Tyr Val Ser Ile His Val Asn Gly Gly Gln Pro Met Val
        35                  40                  45
Phe Gly Gly Ser Glu Asp Pro Cys Pro Val Cys Val Leu Lys Ser Ile
    50                  55                  60
Gly Cys Val Gly Pro Lys Val Asn Asn Ser His Ala Glu Lys Leu Tyr
65                  70                  75                  80
Lys Leu Leu Ala Asp Glu Leu Lys Ile Pro Lys Asn Arg Cys Tyr Ile
                85                  90                  95
Glu Ser Val Asp Ile Glu Ala Ser Ser Met Ala Phe Asn Gly Ser Thr
            100                 105                 110
Phe Gly

<210> SEQ ID NO 13
<211> LENGTH: 118
<212> TYPE: PRT
<213> ORGANISM: Ancylostoma duodenale

<400> SEQUENCE: 13

Pro Met Val Arg Val Ala Thr Asn Leu Pro Asp Lys Asp Val Pro Ala
1               5                   10                  15
Asn Phe Glu Glu Arg Leu Thr Asp Ile Leu Ala Glu Ser Met Asn Lys
            20                  25                  30
Pro Arg Asn Arg Ile Ala Ile Glu Val Met Ala Gly Gln Arg Ile Thr
        35                  40                  45
His Gly Ala Ser Arg Asn Pro Val Ala Val Ile Lys Val Glu Ser Ile
    50                  55                  60
Gly Ala Leu Ser Ala Asp Asp Asn Ile Arg His Thr Gln Lys Ile Thr
65                  70                  75                  80
Gln Phe Cys Gln Asp Thr Leu Lys Leu Pro Lys Asp Lys Val Ile Ile
                85                  90                  95
Thr Tyr Phe Asp Leu Gln Pro Ile His Val Gly Phe Asn Gly Thr Thr
            100                 105                 110
Val Ala Ala Ala Thr Met
        115

<210> SEQ ID NO 14
<211> LENGTH: 118
<212> TYPE: PRT
<213> ORGANISM: Ancylostoma ceylanicum

<400> SEQUENCE: 14
```

```
Pro Met Val Arg Val Ala Thr Asn Leu Pro Asp Lys Asp Val Pro Ala
1               5                   10                  15

Asn Phe Glu Glu Arg Leu Thr Asp Leu Leu Ala Glu Ser Met Asn Lys
            20                  25                  30

Pro Arg Asn Arg Ile Ala Ile Glu Val Leu Ala Gly Gln Arg Ile Thr
        35                  40                  45

His Gly Ala Ser Arg Asn Pro Val Ala Val Ile Lys Val Glu Ser Ile
    50                  55                  60

Gly Ala Leu Ser Ala Asp Asp Asn Ile Arg His Thr Gln Lys Ile Thr
65                  70                  75                  80

Gln Phe Cys Gln Asp Thr Leu Lys Leu Pro Lys Asp Lys Val Ile Ile
                85                  90                  95

Thr Tyr Phe Asp Leu Gln Pro Ile His Val Gly Phe Asn Gly Thr Thr
            100                 105                 110

Val Ala Ala Ala Thr Met
        115

<210> SEQ ID NO 15
<211> LENGTH: 114
<212> TYPE: PRT
<213> ORGANISM: Ancylostoma ceylanicum

<400> SEQUENCE: 15

Pro Val Phe Gln Leu His Thr Asn Val Ser Gln Asp Lys Val Thr Pro
1               5                   10                  15

Asp Leu Leu Lys Gln Ile Ser Ala Leu Val Ala Arg Ile Leu His Lys
            20                  25                  30

Pro Glu Ser Tyr Val Ala Val His Val Val Pro Asp Gln Lys Met Thr
        35                  40                  45

Phe Ala Gly Thr Asp Gly Pro Cys Gly Ile Gly Ile Leu Lys Ser Ile
    50                  55                  60

Gly Gly Val Gly Gly Ser Gln Asn Asn Ser His Ala Lys Ala Leu Phe
65                  70                  75                  80

Ala Leu Ile Lys Asp His Leu Gly Ile Glu Gly Ser Arg Met Tyr Ile
                85                  90                  95

Glu Phe Val Asp Ile Gly Ala Ser Asp Ile Ala His Asn Gly Arg Thr
            100                 105                 110

Phe Ala

<210> SEQ ID NO 16
<211> LENGTH: 113
<212> TYPE: PRT
<213> ORGANISM: Trichinella spiralis

<400> SEQUENCE: 16

Pro Ile Phe Thr Leu Asn Thr Asn Ile Lys Ala Thr Asp Val Pro Ser
1               5                   10                  15

Asp Phe Leu Ser Ser Thr Ser Ala Leu Val Gly Asn Ile Leu Ser Lys
            20                  25                  30

Pro Gly Ser Tyr Val Ala Val His Ile Asn Thr Asp Gln Gln Leu Ser
        35                  40                  45

Phe Gly Gly Ser Thr Asn Pro Ala Ala Phe Gly Thr Leu Met Ser Ile
    50                  55                  60

Gly Gly Ile Glu Pro Ser Arg Asn Arg Asp His Ser Ala Lys Leu Phe
65                  70                  75                  80

```
Asp His Leu Asn Lys Lys Leu Gly Ile Pro Lys Asn Arg Met Tyr Ile
                 85                  90                  95

His Phe Val Asn Leu Asn Gly Asp Val Gly Trp Asn Gly Thr Thr
                100                 105                 110

Phe

<210> SEQ ID NO 17
<211> LENGTH: 113
<212> TYPE: PRT
<213> ORGANISM: Trichuris trichiura

<400> SEQUENCE: 17

Pro Ile Phe Thr Phe Ser Thr Asn Val Pro Ser Glu Asn Ile Ser Val
1               5                   10                  15

Asp Phe Leu Lys Ser Thr Ser Lys Leu Ile Ala Gly Met Leu Gly Lys
                20                  25                  30

Pro Glu Ser Tyr Val Ala Val His Ile Asn Gly Gly Gln Lys Ile Thr
                35                  40                  45

Phe Gly Gly Thr Asp Ala Pro Ala Gly Phe Gln Leu Leu Ser Leu
    50                  55                  60

Gly Gly Val Gly Gly Glu Lys Asn Arg Ser His Ser Ala Lys Leu Phe
65                  70                  75                  80

Lys His Leu Thr Asp Gly Leu Gly Ile Pro Gly Asn Arg Met Tyr Ile
                85                  90                  95

Asn Phe Val Asp Met Arg Gly Ser Asp Val Gly Tyr Asn Gly Ser Thr
                100                 105                 110

Phe

<210> SEQ ID NO 18
<211> LENGTH: 114
<212> TYPE: PRT
<213> ORGANISM: Onchocerca volvulus

<400> SEQUENCE: 18

Pro Ala Phe Thr Ile Asn Thr Asn Ile Pro Gln Ser Asn Val Ser Asp
1               5                   10                  15

Ala Phe Leu Lys Lys Ala

```
<210> SEQ ID NO 19
<211> LENGTH: 4
<212> TYPE: PRT
<213> ORGANISM: P.falciparum

<400> SEQUENCE: 19

Asn Ala Asn Pro
1
```